United States Patent
Kuriger et al.

(10) Patent No.: US 11,813,400 B2
(45) Date of Patent: Nov. 14, 2023

(54) APPARATUS FOR PROVIDING A FLOW OF AIR TO A USER

(71) Applicant: Fisher & Paykel Healthcare Limited, Auckland (NZ)

(72) Inventors: Donald Roy Kuriger, Auckland (NZ); Paul Mathew Freestone, Auckland (NZ); Melissa Catherine Bornholdt, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 9 days.

(21) Appl. No.: 15/769,707

(22) PCT Filed: Oct. 21, 2016

(86) PCT No.: PCT/IB2016/056321
§ 371 (c)(1),
(2) Date: Apr. 19, 2018

(87) PCT Pub. No.: WO2017/068530
PCT Pub. Date: Apr. 27, 2017

(65) Prior Publication Data
US 2020/0155778 A1    May 21, 2020

Related U.S. Application Data

(60) Provisional application No. 62/367,879, filed on Jul. 28, 2016, provisional application No. 62/245,463, filed on Oct. 23, 2015.

(51) Int. Cl.
*A61M 16/00* (2006.01)
*A61M 16/06* (2006.01)
(Continued)

(52) U.S. Cl.
CPC .... *A61M 16/0066* (2013.01); *A61M 16/0622* (2014.02); *A61M 16/0633* (2014.02);
(Continued)

(58) Field of Classification Search
CPC .... A61M 16/00; A61M 16/0003–0012; A61M 16/06; A61M 16/0622;
(Continued)

(56) References Cited

U.S. PATENT DOCUMENTS 5,372,130 A    12/1994  Stern et al.
2003/0172930 A1  9/2003  Kullik et al.
(Continued)

FOREIGN PATENT DOCUMENTS

CN    102740914 A    10/2012
CN    104069577      10/2014
(Continued)

OTHER PUBLICATIONS

Extended European Search Report, Application No. PCT/IB2016/056321, dated May 16, 2019, in 10 pages.
(Continued)

*Primary Examiner* — Samchuan C Yao
*Assistant Examiner* — Yurie Hong
(74) *Attorney, Agent, or Firm* — Knobbe Martens Olson and Bear, LLP

(57) ABSTRACT

A patient interface comprises a blower, a cushion for contacting a user's face, and a mask body and/or a frame for supporting the cushion on a user's face. The cushion and/or the mask body or frame define an interior space for receiving a flow of gases from the blower. The blower is mounted to the mask body or frame so that the blower is at least partially within the mask body or frame. The blower substantially separates a high pressure side of the mask body or frame from a low pressure side of the mask body or frame and/or
(Continued)

the mask body or frame is substantially without a wall between the blower and the interior space.

28 Claims, 44 Drawing Sheets

(51) Int. Cl.
    *A61M 16/10*         (2006.01)
    *A61M 16/16*         (2006.01)

(52) U.S. Cl.
    CPC ...... *A61M 16/0683* (2013.01); *A61M 16/109* (2014.02); *A61M 16/16* (2013.01); *A61M 2205/8206* (2013.01); *A61M 2205/8243* (2013.01); *A61M 2209/086* (2013.01)

(58) Field of Classification Search
    CPC ....... A61M 16/0633; A61M 2016/0015–0042; A61M 2016/0661; A61M 16/0066; A61M 2202/0208; A62B 7/00; A62B 7/14; A62B 9/00; A62B 9/02–027; B63B 11/12; B63B 11/18
See application file for complete search history.

(56) References Cited

U.S. PATENT DOCUMENTS

| | | | |
|---|---|---|---|
| 2007/0000493 | A1 | 1/2007 | Cox |
| 2010/0170513 | A1 | 7/2010 | Bowditch et al. |
| 2010/0313891 | A1* | 12/2010 | Veliss ............... A61M 16/0622 128/206.26 |
| 2012/0138058 | A1* | 6/2012 | Fu ......................... F04D 25/084 128/204.23 |
| 2012/0152255 | A1* | 6/2012 | Barlow ............. A61M 16/0683 128/205.25 |
| 2012/0157794 | A1 | 6/2012 | Goodwin et al. |
| 2012/0199129 | A1 | 8/2012 | Kenyon et al. |
| 2012/0266873 | A1* | 10/2012 | Lalonde ............ A61M 16/0063 128/205.24 |
| 2012/0304985 | A1 | 12/2012 | Lalonde |
| 2014/0360504 | A1 | 12/2014 | Kwok |
| 2015/0217073 | A1 | 8/2015 | Nitta et al. |

FOREIGN PATENT DOCUMENTS

| | | |
|---|---|---|
| EP | 0558147 | 9/1993 |
| EP | 1655052 | 5/2006 |
| EP | 2085106 | 8/2009 |
| FR | 2853838 | 10/2004 |
| GB | 2215217 | 9/1989 |
| JP | H07-10770 Y2 | 3/1995 |
| JP | 2007-506482 | 3/2007 |
| JP | 2012-527908 | 11/2012 |
| JP | 2014-223099 | 12/2014 |
| WO | WO 2008/028247 | 3/2008 |
| WO | WO 2011/017763 | 2/2011 |
| WO | WO 2011/022779 | 3/2011 |
| WO | WO 2011/060479 | 5/2011 |
| WO | WO 2012/113027 | 8/2012 |
| WO | WO 2012/145358 | 10/2012 |
| WO | WO 2014/007655 | 1/2014 |
| WO | WO 2015/099011 | 7/2015 |
| WO | WO 2015/115489 | 8/2015 |
| WO | WO 2015/168340 | 11/2015 |
| WO | WO 2002/092170 | 11/2022 |

OTHER PUBLICATIONS

The State Intellectual Property Office of People's Republic of China, First Office Action; Application No. 2016800695915, dated Apr. 7, 2020; 16 pages.
International Search Report; PCT/IB2016/056321; dated May 18, 2017; 6 pages.
Written Opinion; PCT/IB2016/056321; dated May 18, 2017; 8 pages.
European Examination Report for EP Application No. 16857024.0, dated Oct. 9, 2020 in 5 pages.
Japanese Office Action for Japanese Application No. 2018-521077, dated Oct. 27, 2020, in 6 pages.
Search Report for Japanese Application No. 2018-521077, dated Oct. 21, 2020, in 31 pages.

\* cited by examiner

APPARATUS FOR PROVIDING A FLOW OF AIR TO A USER

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of Invention

The present disclosure generally relates to apparatuses for providing a flow of air to a user.

Description of Related Art

Respiratory disorders deal with the inability of a sufferer to effect a sufficient exchange of gases with the environment, leading to an imbalance of gases in the sufferer. These disorders can arise as a pathological consequence of an obstruction of the airway, insufficiency of the lungs in generating negative pressure, an irregularity in the nervous function of the brain stem, or some other physiological complication. Treatment of such disorders is diverse and depends on the particular respiratory disorder being targeted. In the first instance, a constriction of the airway, otherwise known as an obstructive apnea or a hypopnea (collectively referred to as obstructive sleep apnea or OSA), can occur when the muscles that normally keep the airway open in a patient relax during slumber to the extent that the airway is constrained or completely closed off, a phenomenon often manifesting itself in the form of snoring. When this occurs for a significant period of time, the patient's brain typically recognizes the threat of hypoxia and partially wakes the patient in order to open the airway so that normal breathing may resume. The patient may be unaware of these occurrences, which may occur as many as several hundred times per session of sleep. This partial awakening may significantly reduce the quality of the patient's sleep, over time potentially leading to a variety of symptoms, including chronic fatigue, elevated heart rate, elevated blood pressure, weight gain, headaches, irritability, depression and anxiety.

Obstructive sleep apnea is commonly treated with the application of positive airway pressure (PAP) therapy. PAP therapy involves delivering a flow of gas to a patient at a therapeutic pressure above atmospheric pressure that may reduce the frequency and/or duration of apneas, hypopneas, and/or flow limitations. This therapy may be delivered by using a positive airway pressure device (PAP device or blower) to propel a pressurized stream of air through a conduit to a patient through an interface or mask located on the face of the patient.

The stream of air may be heated to near body temperature. The stream of air may be humidified. The humidification may be performed by forcing the stream of air to travel through a respiratory humidifier containing water and a heater for heating the water. In such a system the heater encourages the evaporation of the water, which in turn partially or fully imbues the stream of air with moisture and/or heat. This moisture and/or heat may help to ameliorate discomfort that may arise from the use of unhumidified PAP therapy.

A typical Continuous Positive Airway Pressure (CPAP) system 100 is illustrated in FIG. 1. In the illustrated configuration, the respiratory system 1 comprises a flow generator 2. The flow generator 2 comprises a gas inlet 3 and a gas outlet 4. The flow generator comprises a blower 6. The blower 6 comprises a motor. In use, the motor drives an impeller of the blower to rotate to draw in gas from the gas inlet 3. The flow generator 2 may comprise a user interface 8 which may comprise one or more buttons, knobs, dials, switches, levers, touch screens, and/or displays so that a user might input operation parameters into the flow generator 2 to control its operation or operation of other aspects of the respiratory therapy system 1.

The flow generator 2 passes gas through the gas outlet 4 to a first conduit 10. The first conduit 10 may pass the gas to a humidifier 12 that may entrain moisture in the gas to provide a humidified gas stream. The humidifier 12 comprises a humidifier inlet 16, a humidifier outlet 18 and a reservoir 14 that may be filled with water or some other humidifying agent. The humidifier 12 also comprises a heating element 13. The heating element 13 may be used to heat the humidifying agent in the reservoir 14 to encourage agent vaporization and/or entrainment in the gas flow and/or increase the temperature of gases passing through the humidifier 12. The humidifier 12 may have a user interface 20 comprising one or more buttons, knobs, dials, switches, levers, touch screens, and/or displays so that a user might input operation parameters into the humidifier 12 to control the operation of the heating element 13, operation of other aspects of the humidifier 12, and or other aspects of the respiratory therapy system 1.

Gas may then pass from the humidifier outlet 18 to a second conduit 22. The second conduit 22 may comprise a heater. The heater may be used to add heat to gases passing through the second conduit 22 in order to prevent the condensation of moisture entrained in the gas stream along the walls of the second conduit 22. Gas passing through the second conduit 22 enters a patient interface 24 that pneumatically links the respiratory therapy system 1 to the patient's airway. The patient interface 24 may comprise for example a nasal mask, an oral mask, an oro-nasal mask, a full face mask, a nasal pillows mask, a nasal cannula, an endotracheal tube, or a combination of these. The flow generator 2, humidifier 12, and/or other parts of the respiratory therapy system 1 may comprise a controller (not shown). The controller may be a microprocessor. The controller may help to control the operation of the flow generator 2, humidifier 12, and/or other aspects or operation parameters of the respiratory therapy system 1.

One disadvantage of a typical CPAP system is that the patient must wear a patient interface that is connected to the system via a conduit 22. The conduit extending from the patient interface worn on the patient's face can interfere with the patient's sleep. The conduit may hang from the patient interface and/or may apply a force to the interface that can cause the interface to move on the patient's face or apply pressure to the patient's face. WO2014/168489 provides further explanation of the forces that can be exerted on a patient interface from an attached conduit. Movement or increased pressure due to movement of the interface on a user's face can cause a patient to be woken during sleep and/or prevent effective treatment by the system. In some instances, tension on the conduit, for example as a patient's turns over in bed, may dislodge the patient interface from the patient's face. Or a patient may become annoyed by the conduit and remove and discard the interface even while asleep.

Respiratory interfaces or masks are used to provide respiratory gas or gases, such as air in CPAP therapy, including in for example VPAP and BiPAP systems, or NW, or high flow rate therapy, for example.

Commonly a respiratory interface comprises a mask frame or body to which for example headgear attaches which holds the interface in position on the user's head when worn, and a seal or cushion to interface to a user's mouth and/or nose to deliver respiratory gases to the user. A respiratory interface may comprise a nasal, oral, or oro-nasal (also referred to as full face) seal module. In turn an interface may be an indirect interface which covers the nose, mouth, or both, or a direct interface such as an interface comprising nasal nozzles or pillows or similar which enter into and seal against or within the nares of the wearer or cannula which non-sealingly enter the nares. The seal module can be formed entirely or almost entirely of a soft material which is comfortable against the wearer's face, such as commonly a silicone material, or the seal module may comprise a rigid or semi-rigid frame interfacing part formed of a rigid or semi-rigid material and which couples to the mask frame and a seal part formed of a relatively soft material.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

SUMMARY

It is therefore an object of certain embodiments disclosed herein to provide an apparatus which will go at least some way towards addressing the foregoing problems or which will at least provide the industry with a useful choice.

In accordance with a first aspect of at least one of the embodiments disclosed herein, a patient interface comprises:
- a blower comprising an impeller, a motor for driving rotation of the impeller, a blower housing providing an impeller space for housing the impeller, a blower inlet and a blower outlet,
- a cushion for contacting a user's face,
- a mask body and/or a frame for supporting the cushion on a user's face, the cushion and/or the mask body or frame defining an interior space for receiving a flow of gases from the blower,
- wherein the blower is mounted to the mask body or frame so that the blower is at least partially within the mask body or frame, and
- wherein the blower substantially separates a high pressure side of the mask body or frame from a low pressure side of the mask body or frame and/or wherein the mask body or frame is substantially without a wall between the blower and the interior space.

In some embodiments, the blower is mounted to the mask body or frame by a portion of the blower housing that is radially outside of and/or surrounding the impeller and impeller space.

In some embodiments, the blower is mounted to the mask body or frame by an outer periphery or circumferential portion of the blower housing.

In some embodiments, the blower is located substantially wholly within the mask body and/or the frame.

In some embodiments, the blower is bounded by a perimeter of the mask body around an open front or rear of the mask body.

In some embodiments, the mask body or frame comprises an inlet to the interior space, and wherein the blower is received within the inlet.

In some embodiments, the patient interface comprises the mask body and the frame, wherein the frame is a cushion frame integrated in a cushion module with the cushion, the cushion frame and/or cushion defining the interior space, and the mask body configured to attach headgear to and support the cushion module on a user's face.

In some embodiments, the blower is mounted to the mask body or the cushion frame to be at least partly received within the cushion module.

In some embodiments, the mask body or frame comprises an inlet to the interior space, and wherein the blower is received within the inlet, and wherein the inlet surrounds the impeller and impeller space of the blower and/or the impeller and impeller space are radially within the inlet (at least when viewed from a front of the patient interface).

In some embodiments, the inlet surrounds the motor and/or the motor is located radially within the inlet (at least when viewed from a front of the patient interface).

In some embodiments, the blower is located substantially wholly within the inlet (at least when viewed from a front of the patient interface).

In some embodiments, the mask body comprises the inlet, and wherein the inlet extends into the cushion module so that the blower is at least partly within the cushion module.

In some embodiments, the cushion frame comprises an aperture for gases entry into the interior space, and wherein the aperture receives the inlet to attach the cushion module to the mask body.

In some embodiments, the inlet comprises a ring for receiving the blower.

In some embodiments, the patient interface comprises a cover attached to the mask body or the frame or to the blower housing to cover the blower, the cover comprising a cover inlet to allow a flow of gases to the blower inlet.

In some embodiments, the only substantial pneumatic connection between the low and high pressure sides of the interface is via a flow path through the blower from the blower inlet to the blower outlet.

In some embodiments, the patient interface comprises a seal between the blower housing and the mask body or the cushion frame.

In some embodiments, the seal comprises a resilient and/or compliant sealing material provided to the blower housing or the mask body or the cushion frame.

In some embodiments, the sealing material is over moulded to the blower housing or to the mask body or to the cushion frame.

In some embodiments, the resilient material is over moulded to the cushion frame and is of the same material as the cushion.

In some embodiments, the seal material and the cushion are integrally formed as a unitary member over moulded to the mask body or the cushion frame.

In some embodiments, a rotational axis of the impeller is approximately perpendicular to a user's face or coronal plane or extends towards the user's face.

In some embodiments, the diameter or an overall lateral dimension of the blower is substantially larger than an axial length of the blower.

In some embodiments, the blower comprises an axial outlet, or an axial inlet and an axial outlet.

In some embodiments, the blower comprises a radial outlet, or an axial inlet and a radial outlet.

In some embodiments, the radial outlet is positioned inwards from a side wall of the mask body or frame or cushion so that there is a gap between the outlet and the side wall. In some embodiments, the blower is attached to the mask body or frame by a screw or rotational engagement or a translational engagement such as a snap-fit or push-fit engagement. In some embodiments the blower is permanently attached to the mask body or frame, such that the blower cannot be removed from the mask body or frame by a user, without destroying the interface.

In some embodiments, the blower comprises a volute housing providing a volute space for receiving air from the impeller space via a passage between the impeller space and the volute, the blower delivering a flow of air from the volute space via the outlet of the blower, and wherein the impeller space and the volute space are separated by a dividing wall, and the passage is a gap between an edge of the dividing wall and a side wall of the volute housing.

In some embodiments, the passage is crescent shaped.

In some embodiments, a widest point of the crescent shaped passage is diametrically opposite the outlet of the blower.

In some embodiments, the blower housing comprises the volute housing.

In some embodiments, the volute space is annular and surrounds the motor, the motor located radially within the annular volute space.

In some embodiments, the blower housing comprises a housing and a cap, and wherein the volute space is formed in the housing and the cap attaches to an end of the housing to form the impeller space together with the housing, the blower inlet formed in the cap.

In some embodiments, the housing comprises a motor space for housing the motor.

In some embodiments, wherein the outlet is located radially outwards of the blower inlet.

In some embodiments, the outlet is positioned at an upper or '12 o'clock' position, or at a lower or '6 o'clock' position.

In some embodiments, the interface comprises an HME material located at the blower outlet or between the blower outlet and the cushion.

In some embodiments of the interface the cushion is detachable from the mask body.

In some embodiments of the interface the mask body has a depth in a front-back direction such that the mask body wraps around the front of the cushion or cushion module. In some embodiments, the cushion frame of the cushion module has a depth in a front-back direction such that it defines a hollow interior. In some embodiments the cushion frame has an aperture for gasses entry into the cushion module, by which the cushion module is attached to the mask body. In some embodiments the mask body comprises a center portion and left and right side portions which extend rearwardly and/or over the left and right sides of the user's mouth or cheeks when the interface is worn, and couple to or are integral with head gear. In some embodiments, the mask body also has a height, such that the mask body covers in part or shrouds a front of the cushion or cushion module.

In some embodiments the interface comprises a battery connected to the mask via a cable.

In some embodiments the interface is provided together with a recharging base or cradle configured to receive the battery for recharging.

In some embodiments the interface comprises a battery incorporated in a headgear assembly of the interface. In some embodiments of the interface comprises a battery incorporated in a top headgear strap of the interface.

In some embodiments the interface comprises a recharging port provided on the interface or headgear.

In some embodiments the interface is provided together with a recharging cradle configured to carry the interface when not in use.

In some embodiments the interface comprises a blower on-off switch on the interface. In some embodiments of the interface comprises a button or touch pad blower on-off switch on a front of the mask body.

In some embodiments the interface comprises headgear or a headgear assembly composed at least in part of a textile covered plastic material.

In some embodiments the interface is a nasal interface. The cushion may cover the user's nose or otherwise interface with the nares of the user, for example the cushion may comprises nasal prongs or pillows to interface with or seal against the nares. In some embodiments the interface is a full face interface. The interface cushion may cover both the nose and mouth. The interface may comprise a cushion which covers the mouth and has a nasal outlet or outlets beneath the nose. This cushion may comprise left and right paddle or wing portions in the upper nasal part of the cushion which contact lateral sides of the nose but not a tip of the nose.

In accordance with a second aspect of at least one of the embodiments disclosed herein, a patient interface comprises:

a blower comprising an impeller, a motor for driving rotation of the impeller, a blower housing providing an impeller space for housing the impeller, a blower inlet and a blower outlet, a cushion for contacting a user's face, a mask body and/or frame for supporting the cushion on a user's face, the cushion and/or the mask body or frame defining an interior space for receiving a flow of gases from the blower, an inlet to the interior space, and wherein the blower is received within the inlet.

Embodiments of a patient interface according to the second aspect may include any one or more features stated above in relation to embodiments of a patient interface according to the first aspect. For example, in some embodiments, the inlet surrounds the impeller and impeller space of the blower and/or the impeller and impeller space are radially within the inlet (at least when viewed from a front of the patient interface). In some embodiments, the inlet surrounds the motor and/or the motor is located radially within the inlet (at least when viewed from a front of the patient interface). In some embodiments, the blower is located substantially wholly within the inlet.

In some embodiments, the patient interface comprises the mask body and the frame, wherein the frame is a cushion frame integrated in a cushion module with the cushion, the cushion frame and/or cushion defining the interior space, and the mask body configured to attach headgear to and support the cushion module on a user's face.

In some embodiments, the mask body comprises the inlet, and wherein the inlet extends into the cushion module so that the blower is at least partly within the cushion module.

In some embodiments, the cushion frame comprises an aperture for gases entry into the interior space, and wherein the aperture receives the inlet to attach the cushion module to the mask body.

In some embodiments, the cushion frame comprises the inlet for receiving the blower.

In some embodiments, the inlet comprises a ring for receiving the blower.

In some embodiments, the blower is mounted to the mask body or frame so that the blower is at least partially within the mask body or frame and substantially separates a high pressure side of the mask body or frame from a low pressure side of the mask body or frame In some embodiments, the mask body or frame is without a wall between the blower and the interior space.

In some embodiments, the only substantial pneumatic connection between the low and high pressure sides of the interface is via a flow path through the blower from the blower inlet to the blower outlet.

In some embodiments, the patient interface comprises a seal between the blower housing and the mask body or the cushion frame.

In accordance with a third aspect of at least one of the embodiments disclosed herein, a patient interface comprises:
  a blower,
  a cushion for contacting a user's face,
  a mask body and/or frame for supporting the cushion on a user's face, the cushion and/or the mask body or frame defining an interior space for receiving a flow of gases from the blower, and
  wherein the blower comprises an impeller, a motor for driving rotation of the impeller, the motor comprising a stator and a rotor coupled to the impeller, a blower housing comprising an impeller space for housing the impeller, a blower inlet and a blower outlet, and at least one vibration isolation member between the impeller and the stator and/or between the stator and the blower housing, and
  wherein the blower is mounted to the mask body or the frame without a vibration isolation member between the blower and the mask body or the frame.

Embodiments of a patient interface according to the third aspect may include any one or more features stated above in relation to embodiments of a patient interface according to the first aspect or the second aspect.

In accordance with a fourth aspect of at least one of the embodiments disclosed herein, a patient interface comprises:
  a blower comprising an impeller, a motor for driving rotation of the impeller, a blower housing providing an impeller space for housing the impeller, a blower inlet and a blower outlet,
  a cushion for contacting a user's face,
  a mask body and/or a frame for supporting the cushion on a user's face, the cushion and/or the mask body or the frame defining an interior space for receiving a flow of gases from the blower, and
  wherein the blower is mounted to the mask body or the frame, and wherein the mask body and/or frame is without a vent such as a vent aperture or apertures, the only pneumatic flow path to and from the interior space being via the blower outlet.

Embodiments of a patient interface according to the fourth aspect may include any one or more features stated above in relation to embodiments of a patient interface according to the first, second or third aspects.

Interfaces of the invention may be used in continuous positive airway pressure (CPAP) systems for providing a heated and optionally also humidified air stream to a user (U) through the interface worn by the user, or alternatively in other forms of respiratory systems, such as for example VPAP (Variable Positive Airway Pressure) systems, BiPAP (Bi level Positive Airway Pressure) systems, or in non-invasive ventilation (NW), or high flow rate (not necessarily also above ambient pressure) therapy, for example, and are described herein generally with reference to CPAP therapy by way of example only. The interfaces may be useful particularly for CPAP therapy at air pressures in the range about 0.5 to about 40 cm H2O. However the interfaces may also be used in be used in systems or therapy in which the air or other gases are not heated and/or humidified.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

As used herein the term "and/or" means "and" or "or", or both.

As used herein "(s)" following a noun means the plural and/or singular forms of the noun To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The invention consists in the foregoing and also envisages constructions of which the following gives examples only.

BRIEF DESCRIPTION OF THE DRAWINGS

Embodiments will be described by way of example only and with reference to the drawings and without intending to be limiting, in which:

FIG. 14A is from the front of the interface and FIG. 14B is from the rear.

DETAILED DESCRIPTION OF SPECIFIC EMBODIMENTS

The present invention relates to a wearable PAP system. A wearable PAP system may also be referred to as a patient interface with integrated PAP system, or a patient interface with integrated flow generator or blower, or a patient interface that comprises a flow generator. In this specification and claims, a patient interface with integrated PAP system, flow generator or blower may simply be referred to as a patient interface. In some embodiments, the interfaces may integrate a continuous positive pressure ("CPAP") system, a variable positive airway pressure ("VPAP") system and/or a bi-level positive airway pressure ("BiPAP") system, or an NIV or high flow rate therapy system, for example. A patient interface according to some embodiments is illustrated in FIGS. 2A to 2I. The illustrated patient interface is an indirect nasal mask to pneumatically connect with a patient's nose by covering the patient's nose at least in part, however As stated, in the embodiment of FIGS. 2A to 2I the nasal mask comprises a seal or cushion to seal around the user's nose and against the user's face. In other embodiments the mask may alternatively be a full face (nasal and oral) interface, an oral only interface, or may comprise a direct nasal interface such as nasal nozzles or pillows or similar which enter into and seal against or within the nares of the wearer or cannula which non-sealingly enter the nares. In turn a full face interface may be a fully indirect interface which covers both the nose and mouth, or hybrid full face interface which covers the mouth and comprises nasal nozzles or pillows or similar which enter into the nares or which comprises a seal with a nasal part which contacts the underside of the nose having an outlet which is positioned beneath the nares. In some embodiments the face seal or cushion may not pneumatically seal against the user's face or nose, but may direct a flow of air to the user's airway without forming a seal. In this specification and claims, the term 'cushion', unless the context suggests otherwise, is intended to refer to both sealing and non-sealing face seals or cushions that contact the user's face to pneumatically couple the patient interface to the user's airway.

Figure 2A:
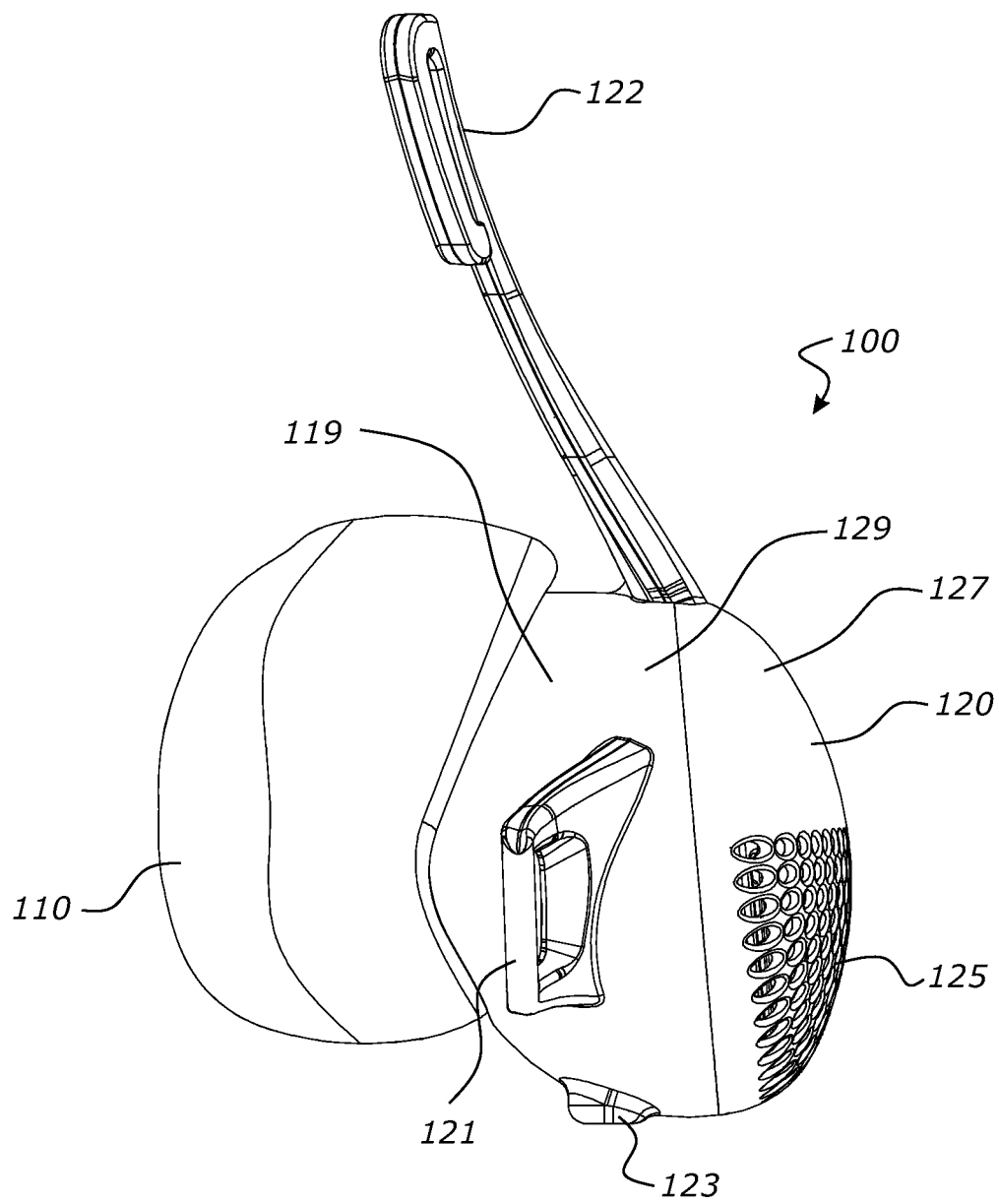
FIG. 2A is a side view of a patient interface.
Figure 2B:
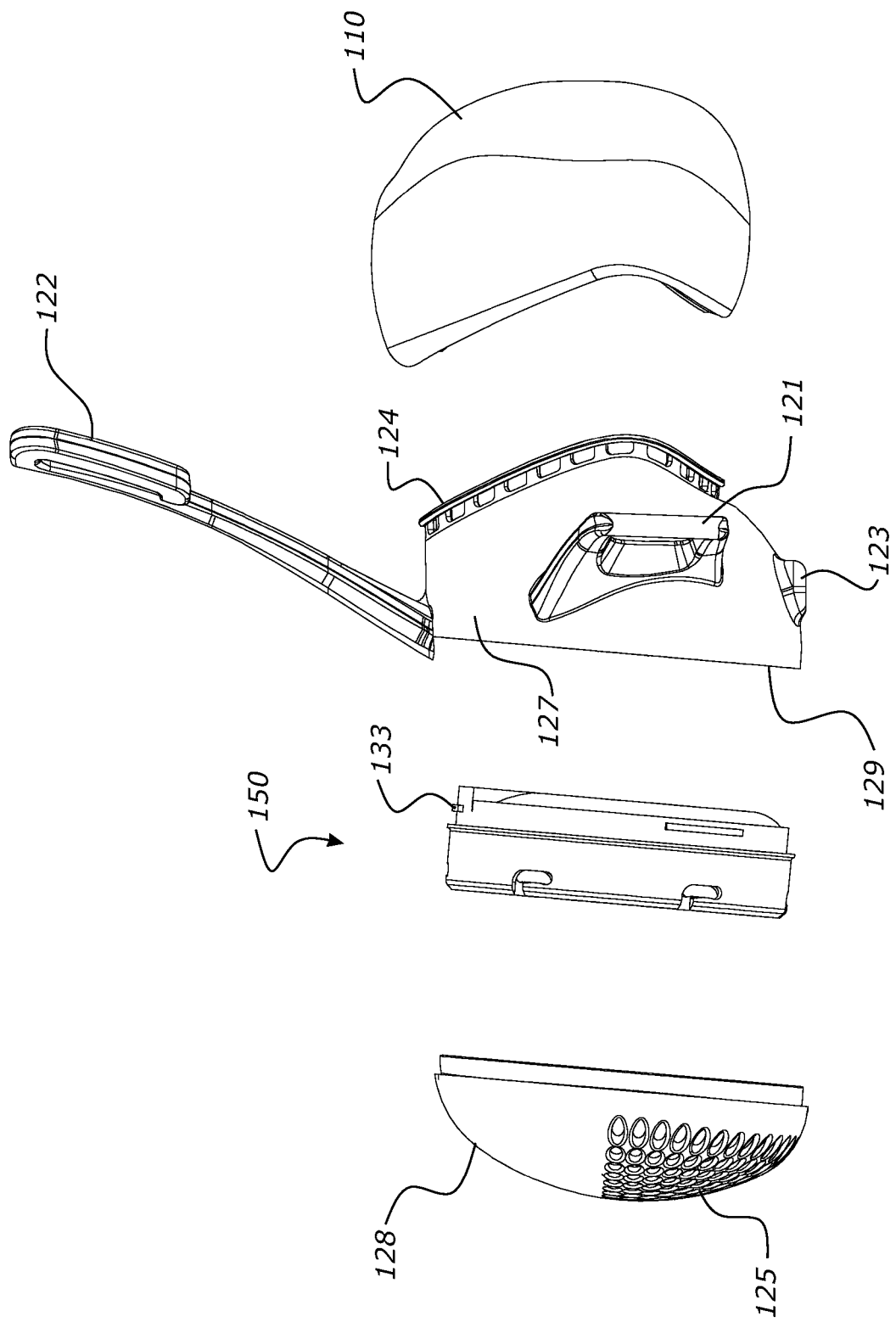
FIG. 2B is an exploded side view of the patient interface of FIG. 2A.

The patient interface 100 shown in FIGS. 2A to 2I comprises a mask frame or body 120. The patient interface 100 is to be positioned around the nose of a user with headgear (not shown) secured to the mask body 120. A mask cushion 110 is attached to or formed with the mask body. The patient interface includes headgear or is attached to headgear in use. The headgear may be attached to the mask body via at least one attachment point 121 or attachment detail on the mask body. A restraining force provided by the headgear on the hollow body 120 ensures a sufficient compressive force on the mask cushion 110 against a patient's face, to provide an effective seal against the patient's face. In FIG. 2A the interface is shown with a forehead support 122, to which the headgear may also attach. In other embodiments the interface is without a forehead support. The interface is shown positioned on a user's face in FIG. 2I.

In some embodiments the body 120 is constructed of a relatively inflexible material. For example, the hollow body 120 may be formed from polycarbonate plastic, or other suitable plastics material. Such a material would provide the requisite rigidity for supporting the cushion 110. The mask body may be transparent, and may be a relatively good insulator. Expiratory gases expelled by a user into the mask body may be expelled or vented through a valve or a vent path or paths through the mask body and/or cushion. For example, there may be a vent aperture or apertures in the mask body (not shown). In some embodiments, as illustrated, the mask body is without a vent path, such that the user must exhale through the blower 150. In the illustrated embodiment there is an aperture 123 for providing access for a power and/or signal cable to provide power and/or signals to a motor of the blower. For example, a cable 60 is illustrated in FIGS. 2I and 7A to 8B.

Figure 8A:
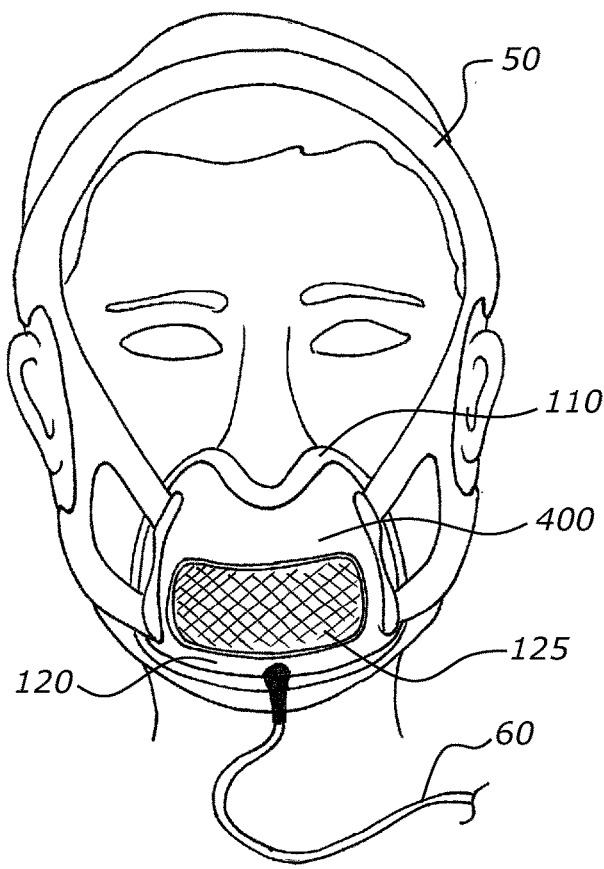
FIGS. 8A and 8B are front and side views of a user wearing a patient interface comprising a blower.
Figure 8B:
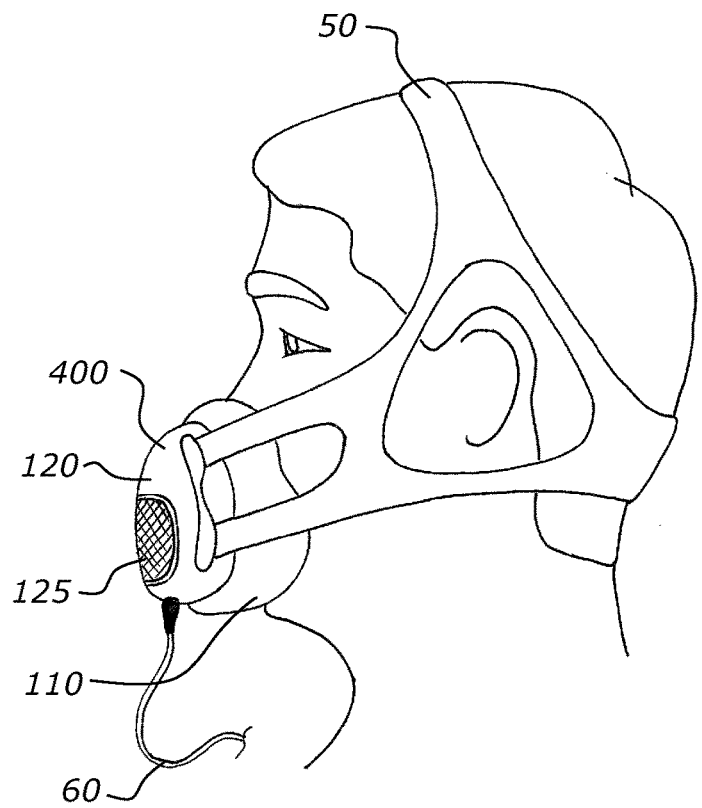
Figure 9A:
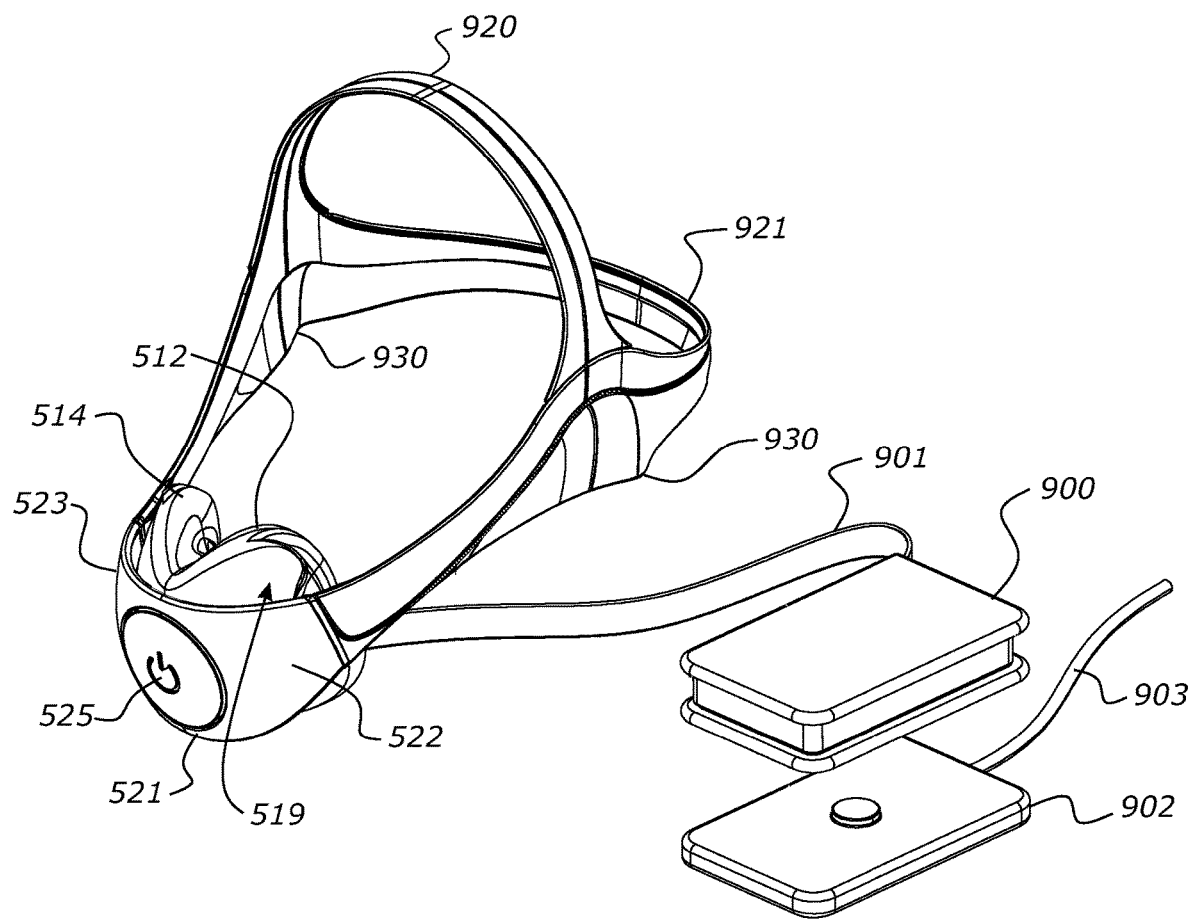
FIG. 9A is a perspective view of another embodiment of a patient interface.
Figure 9B:
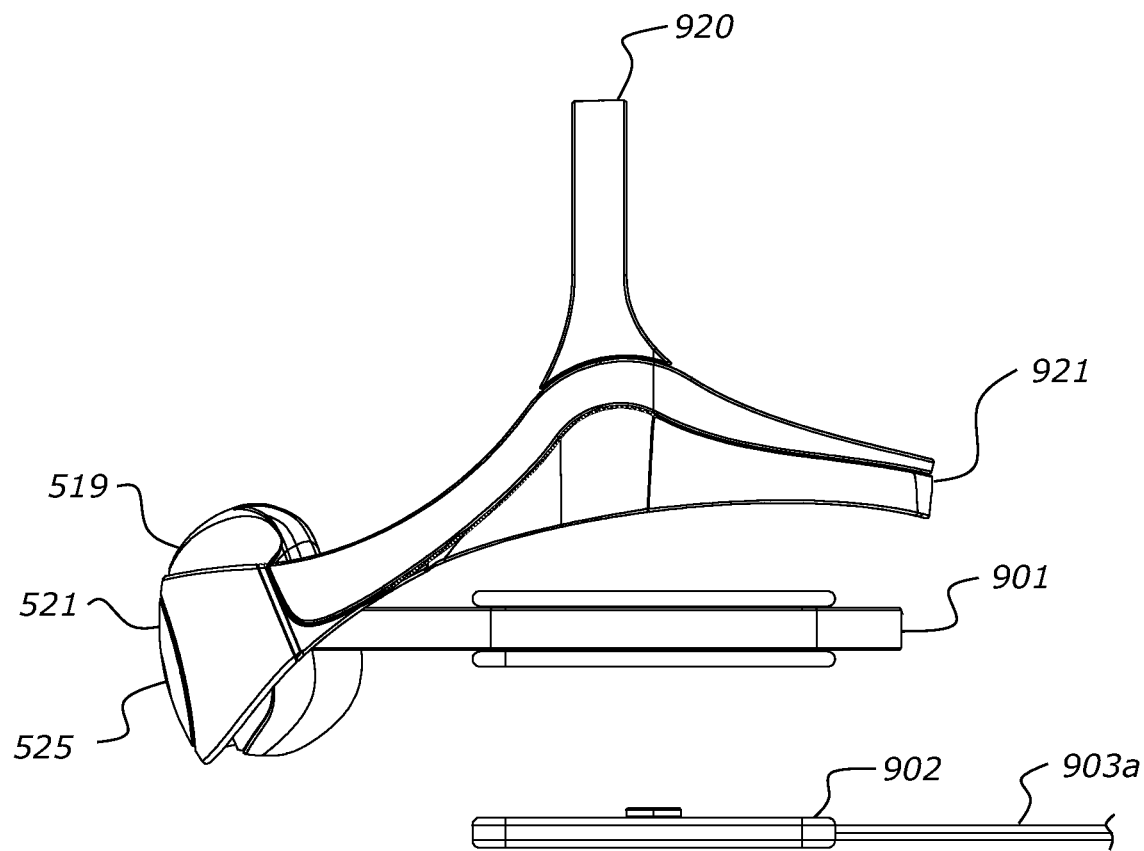
FIG. 9B is a side view of the patient interface of FIG. 9A.
Figure 9C:
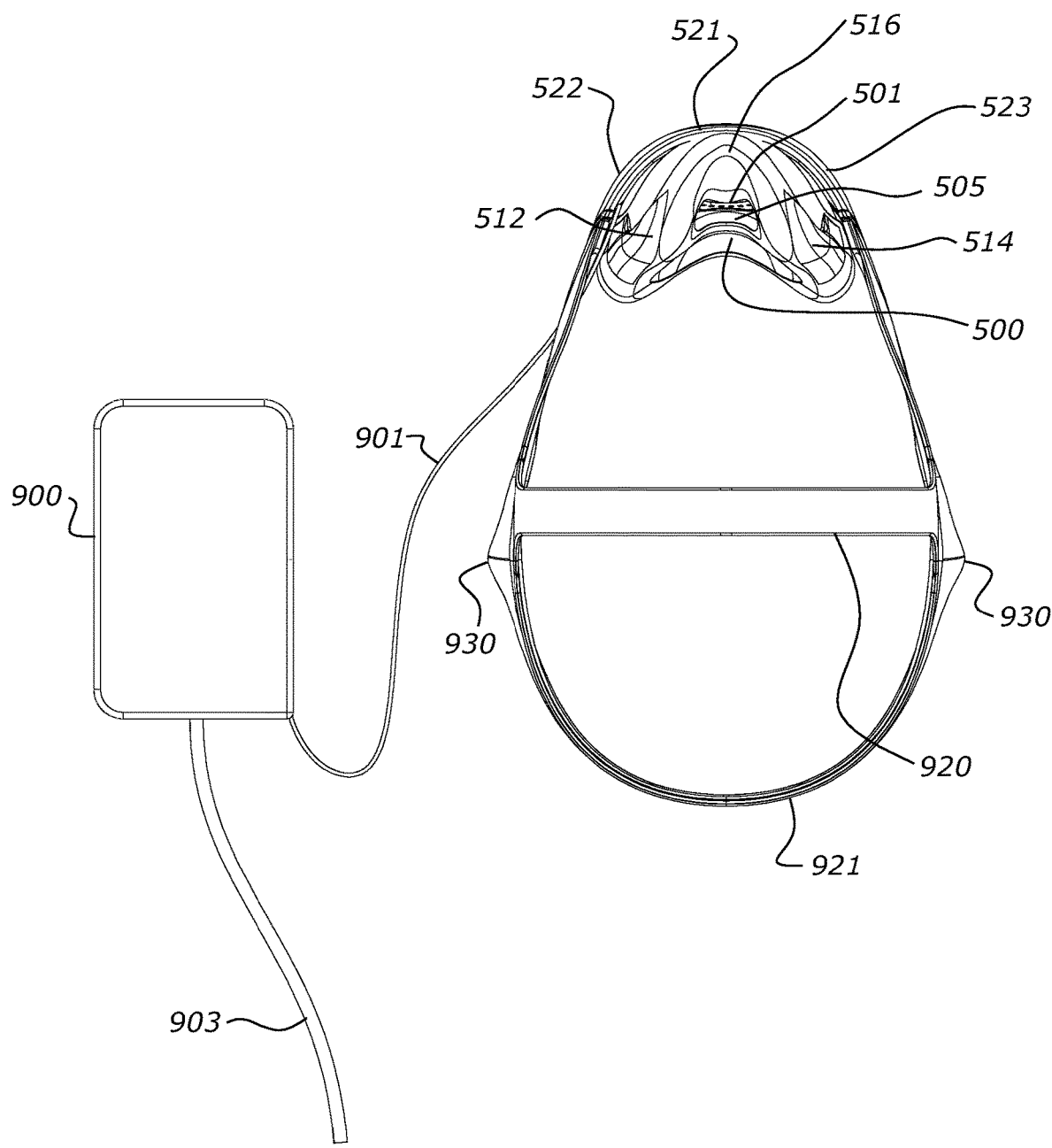
FIG. 9C is a view from above of the patient interface of FIGS. 9A and 9B.
Figure 9D:
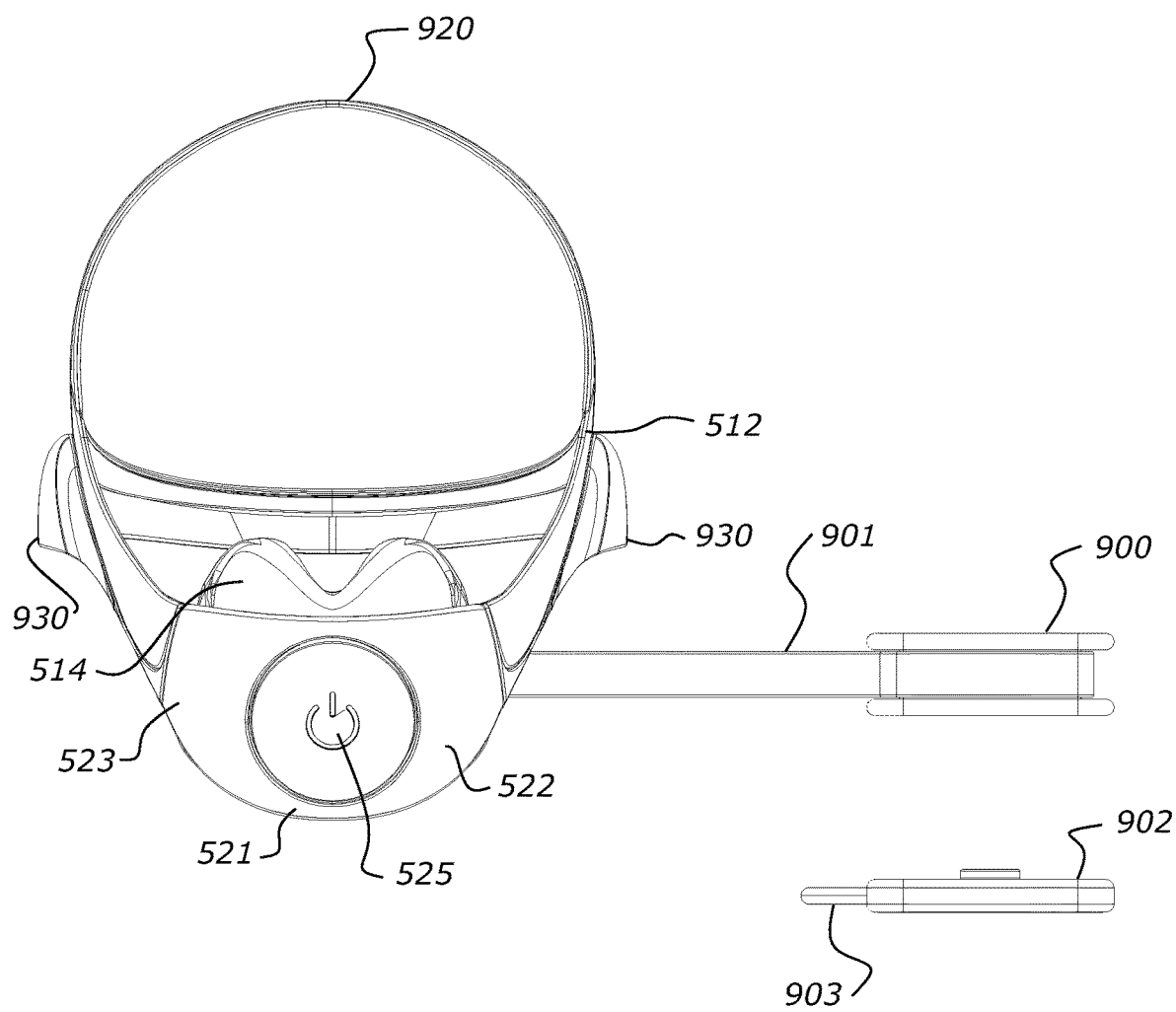
FIG. 9D is a front view of the patient interface of FIGS. 9A to 9C.
Figure 9E:
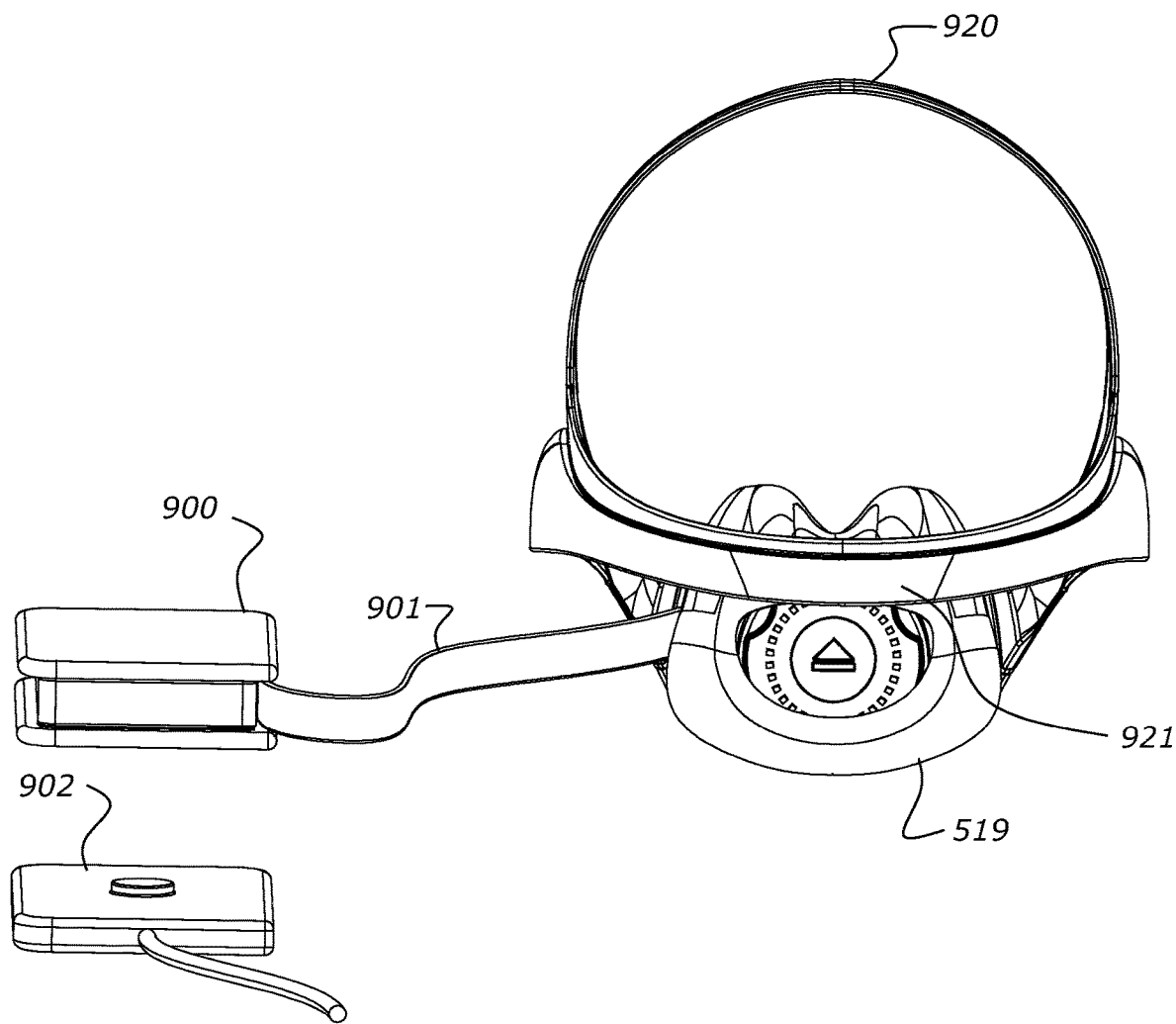
FIG. 9E is a rear view of the patient interface of FIGS. 9A to 9D.

In some embodiments the mask cushion 110 is provided around a periphery of the mask body 120 to provide an effective seal onto the face of the user. The mask seal 110 may be shaped to approximately follow the contours of a patient's face. For example a full face seal may be configured to approximate the facial contours of the user's chin and wider cheek regions and over or adjacent the user's nasal bridge region. In a nasal mask a seal may be contoured to approximately match the facial contours of a user around the user's nose, from the bridge of the nose, continuing down the cheek regions adjacent each side of the user's nose and across the user's philtrum or upper lip area. The mask seal 110 is resilient to deform when pressure is applied by the headgear to adapt to the individual contours of many different users. In some embodiments the seal may be formed from a silicone material. In some embodiments, the seal may be overmoulded to a portion of the mask body. In the illustrated embodiments the seal 110 is overmoulded through holes 124 around a rear periphery of the mask body. In some embodiments the seal may be attached to a relatively rigid seal clip for clipping the resilient seal to the bask body. For example the interface may include a seal assembly, the seal assembly comprising the seal 110 and a relatively rigid seal clip (not shown). The seal clip may releasably attach the seal 110 to the mask body 120. The clip provides a releasable rigid or semi rigid interface, to allow the seal to be easily attached and detached from the mask body many times. In the embodiment of FIG. 2A the seal encloses the nose of the user. In other embodiments the seal may surround both the nose and mouth, or the mouth only, or may seal again the nares of the user. For example, in FIGS. 7A and 7B, a patient interface 300 is illustrated that comprises a seal that surrounds the user's mouth and seals around a lower portion of the user's nose. For example the seal 110 may seal against lateral sides of the user's nose and/or against bottom surfaces of the user's nose. In some embodiments the patient interface 300 may comprise wing portions that assist with sealing against the sides of the user's nose and/or allows the tip of the user's nose to be exposed. A patient interface 400 similar to the interface 300 is illustrated in FIGS. 8A and 8B. The patient interface of FIGS. 7A and 7B has an inlet 125 comprising a plurality of apertures on a front of a mask body of the interface. The patient interface of FIGS. 8A and 8B has an inlet 125 comprising a mesh or a filter material, or a Heat and Moisture Exchange (HME) material.

The patient interface comprises a flow generator (a blower) operable to generate a flow of gases to the user. In some embodiments, with the patient interface positioned on the user's face for use, the blower is located in front of or near the user's face. For example the blower may be positioned in front of a user's mouth and/or nose.

Figure 2C:
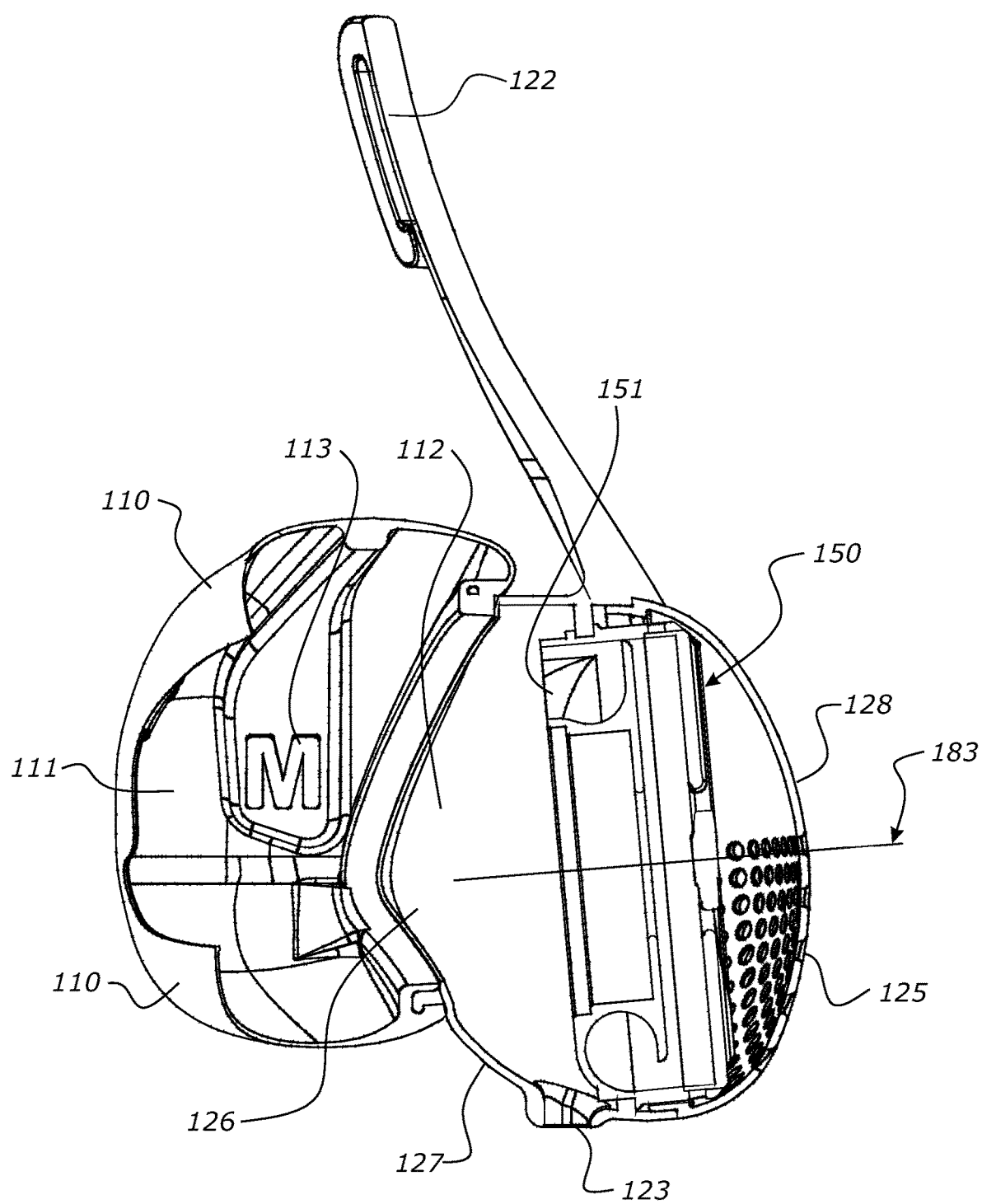
FIG. 2C is a cross sectional view on a centre line of the patient interface of FIG. 2A.
Figure 2D:
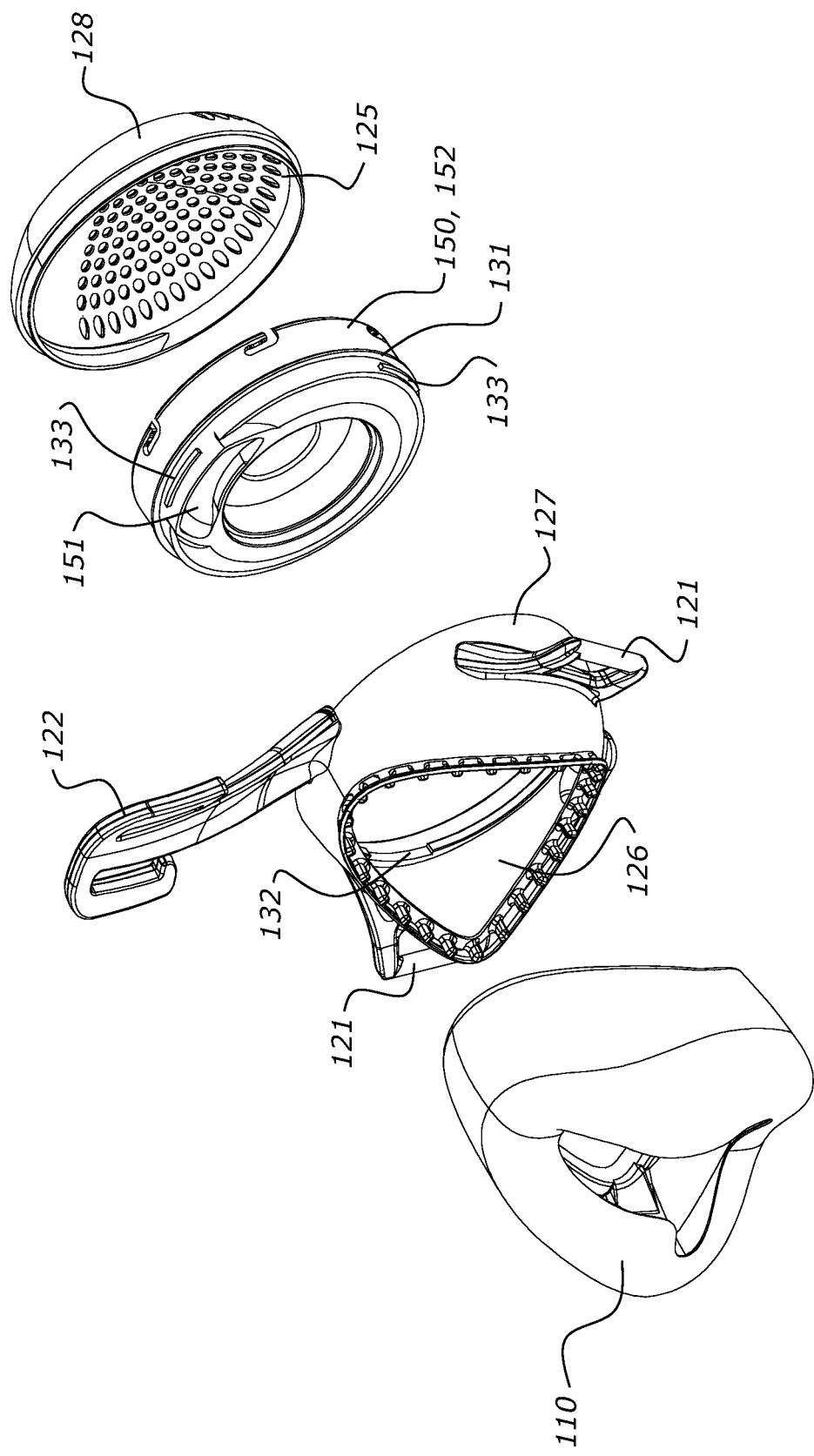
FIG. 2D is an exploded view, from the rear and from above, of the patient interface of FIG. 2A.
Figure 2E:
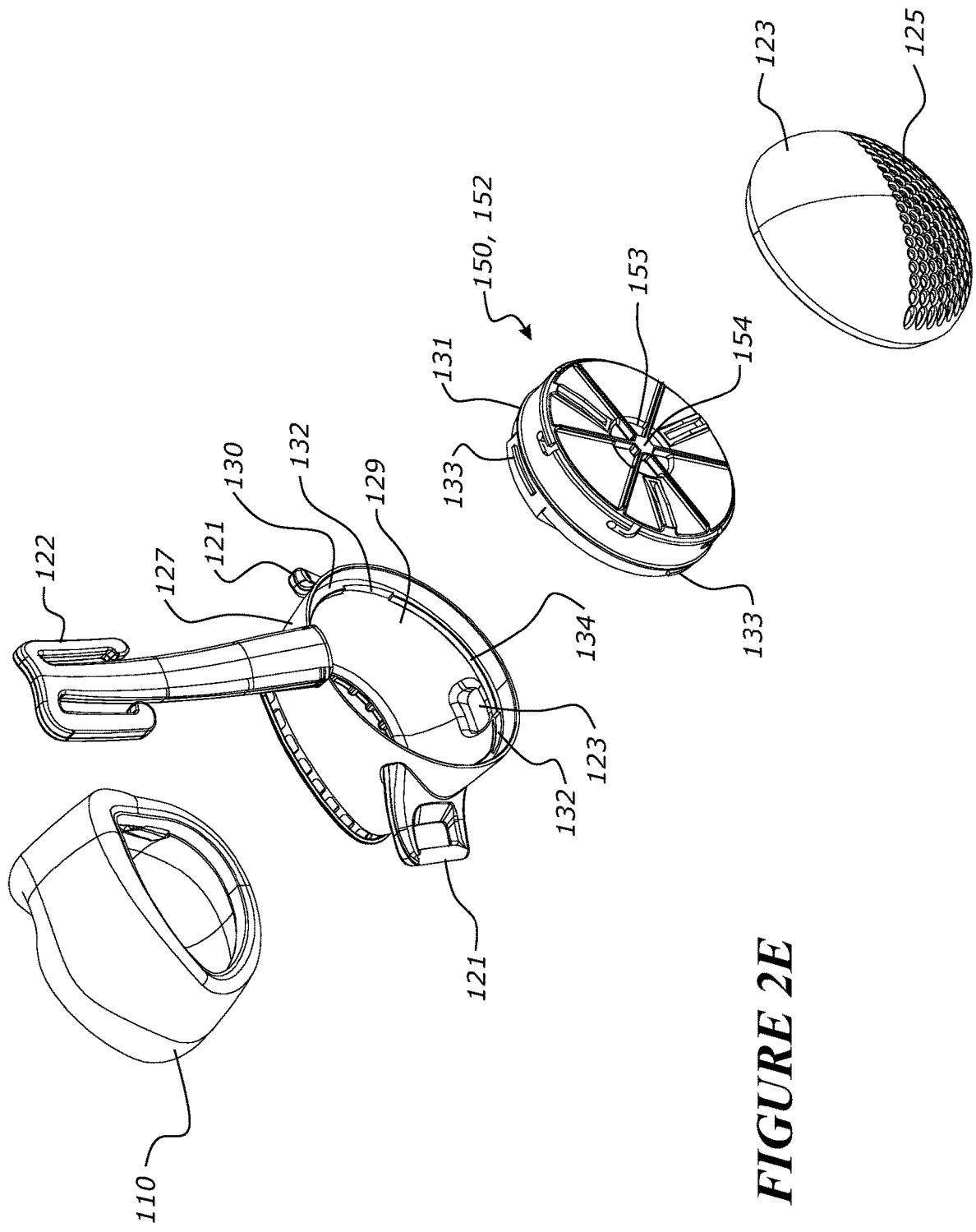
FIG. 2E is an exploded view, from the front and from above, of the patient interface of FIG. 2A.
Figure 2F:
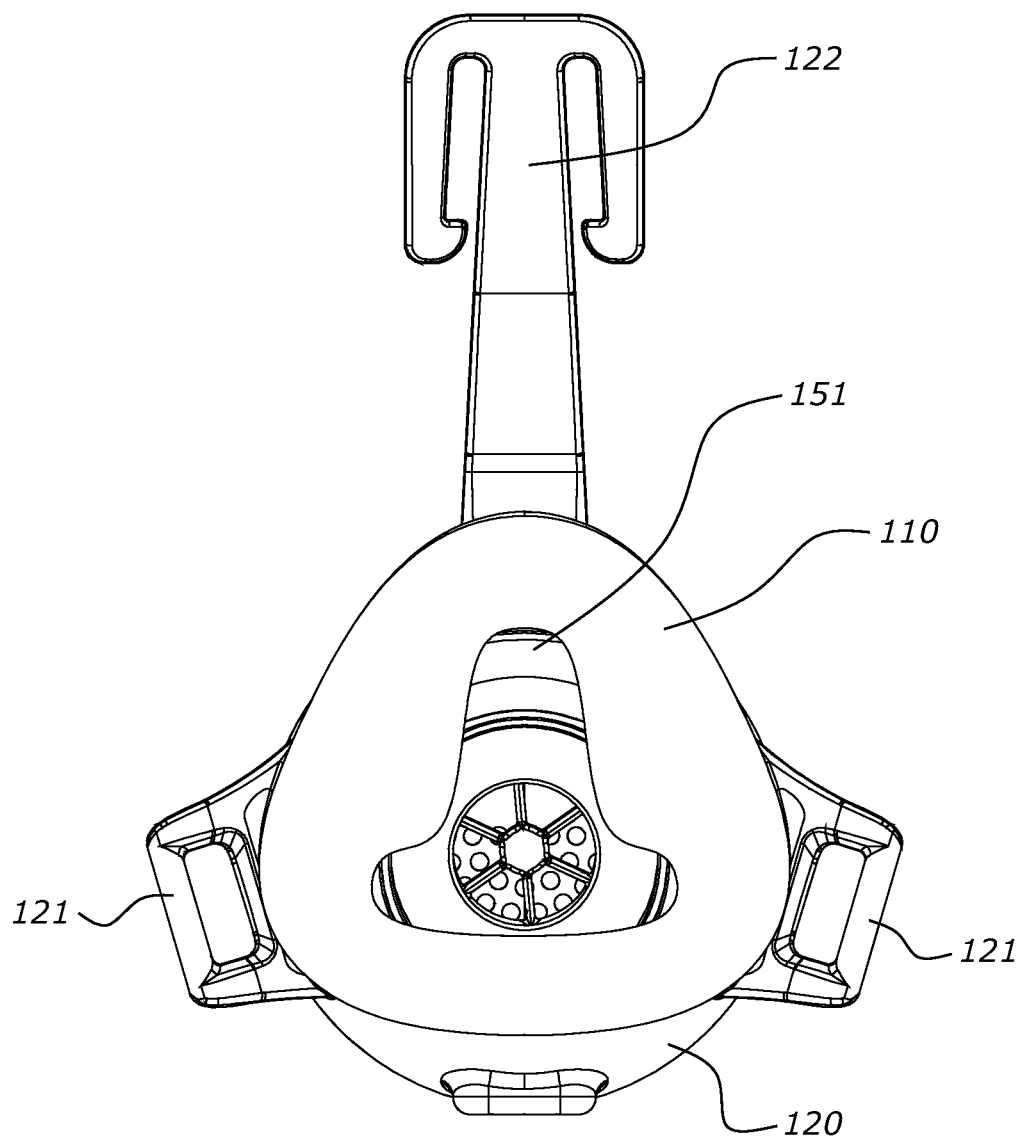
FIG. 2F is a rear view of the patient interface of FIG. 2A.
Figure 2G:
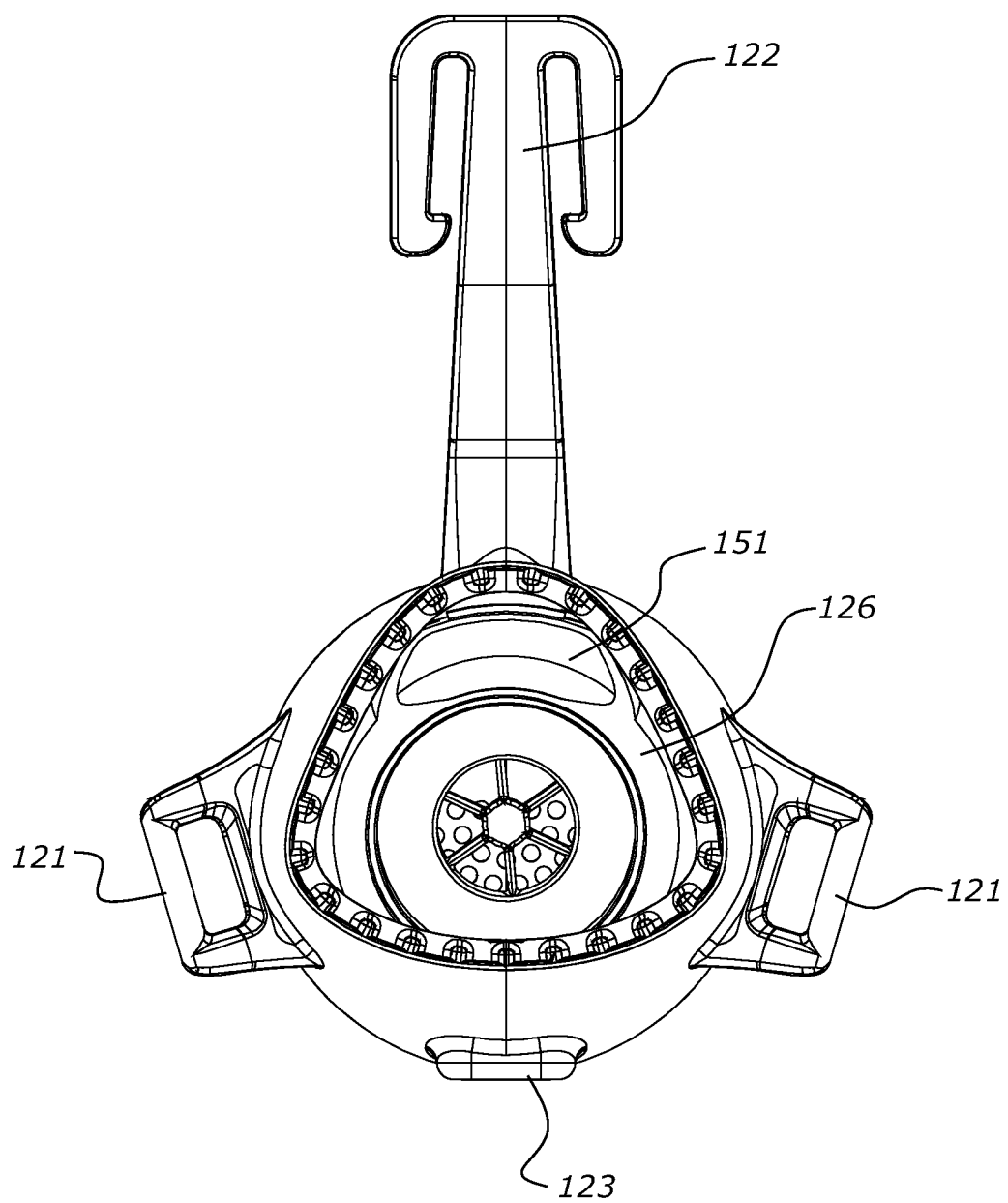
FIG. 2G is a rear view of the patient interface of FIG. 2A and with a cushion of the interface removed from the view.

In some embodiments, the blower 150 is mounted to the mask body 120. As shown in FIG. 2C, in some embodiments the blower is mounted within the mask body. The hollow mask body provides an inner cavity or volume in which the blower is positioned. In some embodiments the mask body together with the cushion provides an interior cavity or space 112 for receiving a flow of gases from an outlet 151 of the blower 150. The interior space may form a reservoir 112 in which pressurised air from the blower may accumulate for breathing by the user. Alternatively or additionally, the seal may provide an internal cavity or volume for receiving air from the blower. In some embodiments the mask body and/or the seal are designed to reduce the internal space or volume of the mask body and/or seal as much as possible, to reduce the 'dead space' within the mask. Reducing the dead space may be beneficial to reduce the amount of carbon dioxide building up in the mask from the user's breath being expelled into the mask. In preferred embodiments, the mask body 120 is without a wall between the interior space 112 and the blower. In some embodiments, the mask body may be without a wall between the blower and the interior space, and the patient interface may comprise a filter or diffuser medium or HME material between the blower or blower outlet and the interior space and/or the cushion. The filter or diffuser or HME material may substantially completely cover the blower such that the blower is not visible within the interior of the patient interface.

In some embodiments the mask body 120 comprises an inlet 125 through which the blower draws air, and an outlet 151 through which the pressurised air is provided to the patient via the seal 110. The seal is attached to or around an outlet of the mask body. In some embodiments, the inlet 125 is located on or at a front portion of the mask body. In some embodiments as shown, the inlet may comprise a plurality of apertures or openings, such as a plurality of apertures arranged in an array. The blower may be assembled to the mask body from a rear side of the mask body, e.g. prior to fitting the cushion to the mask body, or through the cushion.

In some embodiments the mask body comprises a base 127 and a separate cover 128. The mask seal 110 is attached to the base 127. The blower is mounted to the base, and the cover is attached to the base to cover the blower to house the blower within the mask body. In other words, the mask body may be in two parts 127, 128 that are assembled together to secure the blower within the mask body. The seal is preferably attached to a rear periphery of the base and the blower is mounted to the base from a front side 129 of the base. In some embodiments the base 127 together with the cushion provides an interior cavity or space for receiving a flow of gases from an outlet 151 of the blower 150. The space may form a reservoir in which pressurised air from the blower may accumulate for breathing by the user. In some embodiments the cover 128 attaches to the front side 129 of the base to cover the blower. The blower may clip into the mask body or be held by a retaining part or clip. In some embodiments, the blower is held in place against the base by the cover. For example in some embodiments the blower may be sandwiched between the base and the cover to hold the blower in place within the mask body. Alternatively, in some embodiments the blower is mounted to the cover from a rear side of the cover and the cover and base are assembled together to house the blower.

In some embodiments the blower is releasable from the mask body. To remove the blower from the mask body the cover is removed from the base to expose the blower for removal. In some embodiments the mask body may be integrally formed with a housing of the blower.

As shown in FIGS. 2A to 2I, in some embodiments the attachment details or points 121 for attaching a headgear are provided on the base 127 of the mask body. Thus the base supports the seal and the blower and is attached to the user's head by the headgear. However, in some embodiments the attachment details or points 121 may be provided on the cover 128, for example as shown in the embodiment 200 of FIGS. 5A to 5H. In some embodiments the inlet 125 through which the blower draws air is located in the cover 128.

In some embodiments, the cover may not form part of the mask body. For example, the blower may include a cover that is separate from the mask body, or the housing of the blower may be open to the front of the patient interface. In this embodiment, the base 127 described above may be referred to as the mask body. In some embodiments the blower is mounted to the mask body 127 from a front side of the mask body. For example the blower may clip to the mask body 127 via a front side of the mask body. The cover 128 may be part of the blower assembly attached to a housing of the blower. In the illustrated embodiment, the mask body 127 is without a wall between the interior space 112 and the blower. The mask body 127 comprises an open front through which the blower is mounted to the mask body. The blower may be received in and surrounded by a perimeter of the open front of the mask body 127. The blower may be completely bounded by the perimeter of the open front of the mask body. The cover may attached to the perimeter of the open front of the mask body. In some embodiments, mask body is without a wall and the patient interface may comprise a filter or diffuser medium between the blower or blower outlet and the interior space and/or the cushion. The filter or diffuser medium may substantially completely cover the blower such that the blower is not visible within the interior of the patient interface.

In the above described embodiments, the blower 150 is mounted to the mask body 120, 127 by a portion of the blower housing that is radially outside of and/or surrounding an impeller and impeller space of the blower, so that the blower is substantially open to the interior space of the patient interface. In some embodiments, the blower is mounted to the mask body via an outer perimeter or circumferential portion of the blower housing. Therefore there is substantially no wall between the blower and the cushion, or between the blower and the interior space provided by the mask body 120, 127 and/or the cushion 110. Such an arrangement allows for the blower to be provided in the patient interface without ducting or plumbing from the outlet of the blower to the interior space of the patient interface. The blower is mounted to the mask body to substantially separate a high pressure side of the mask body 120, 127, to which the blower delivers a flow of gases, from a low pressure side of the mask body, e.g. an outside of the mask body 120, 127 or a side of the mask body in which an inlet of the blower is arranged, e.g. a side of the mask body to which the cover 128 or a mask body inlet 125 is arranged. In some embodiments the high pressure side of the mask body 120, 127 is the side of the mask body facing or bounding the interior space 112 and the low pressure side of the mask body is an outer side of the mask body.

Figure 2H:
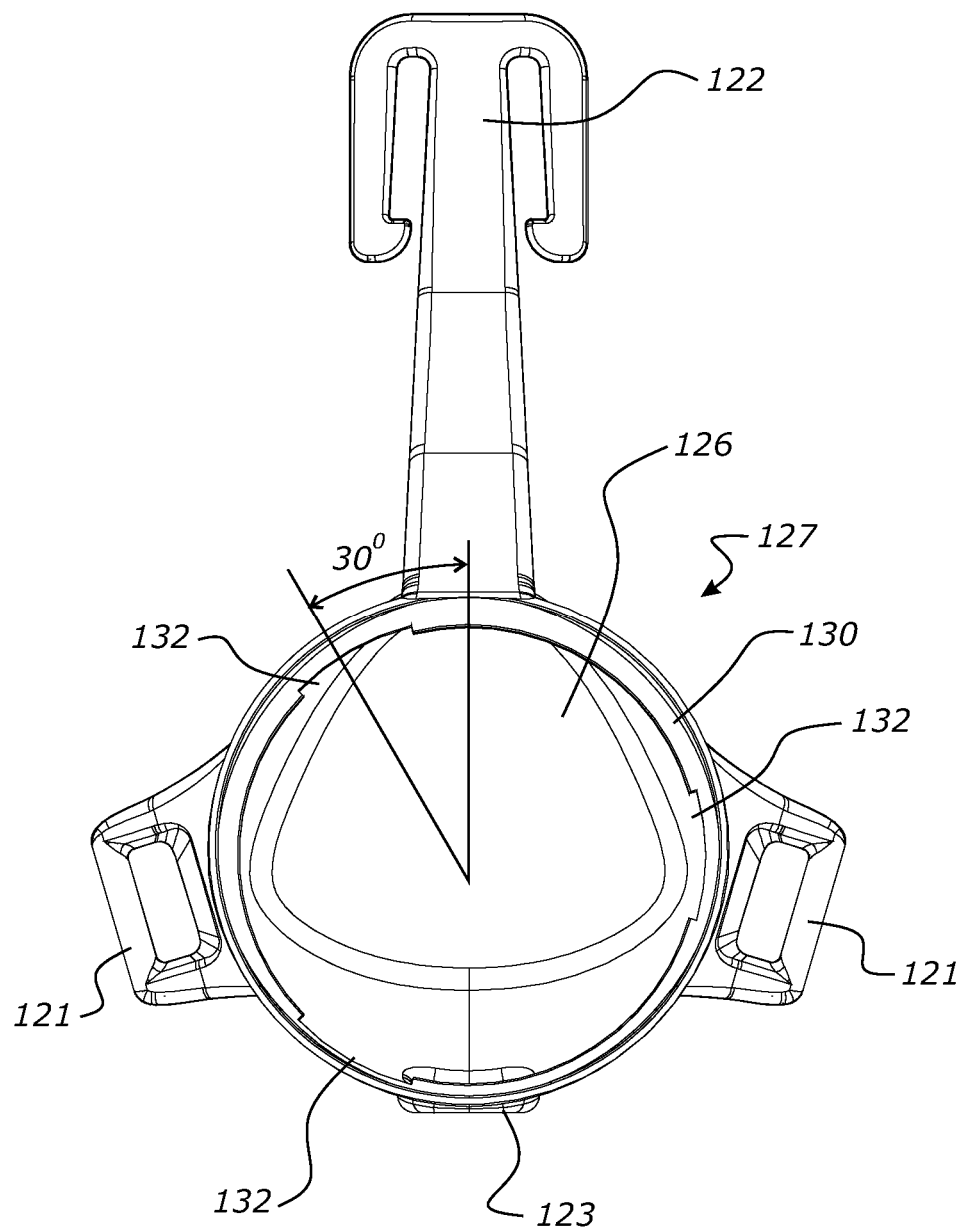
FIG. 2H is a rear view of a mask body of the patient interface of FIG. 2A.

In some embodiments the blower is attached to the mask body 120, 127 (e.g. to the base of the mask body) by a screw or rotational engagement. For example the blower may comprise a threaded outer circumferential surface and the mask body or base of the mask body may comprise a complementary threaded inner circumferential surface to receive the outer surface of the blower in a threaded engagement. Alternatively the blower may attach to the body by a push fit or snap fit engagement for example. In some embodiments the blower and the mask body have a complementary keyed relationship so that the blower is fitted or attached to the body in a correct orientation. In the embodiment illustrated in FIGS. 2A to 2I, the blower is attached to the mask body via a limited rotation such as a 30 degree rotation. The mask body 120, 127 comprises a shoulder or forward facing surface 130 and the blower comprises a corresponding shoulder or rearward facing surface 131. When the blower is attached to the body the surfaces 130, 131 are in contact. The blower also comprises one or more projections 133 and the body 120, 127 comprises a corresponding number of recesses 132 to receive the projections. The blower is fitted to the body 120, 127 with the projections 133 aligned with the recesses 132. Once the surfaces 130, 131 are in contact the blower may be rotated relative to the body 120, 127 so that the projections seat behind a circumferentially extending ridge 134, to hold the blower axially to the mask body. As shown in FIG. 2H, in some embodiments the body comprises three recesses and the blower three projections. In the illustrated embodiment the blower is rotated by 30 degrees to lock or attach the blower to the mask body. The illustrated attachment mechanism may be referred to as a bayonet attachment. Other rotational fitting arrangements are possible, for example the blower may comprise a groove with openings to allow projections on the mask body to enter the groove with subsequent rotation of the blower to the mask base securing the blower in place within the patient interface. Rotational engagement of the blower to the mask body may be a preferred engagement, as a preferred blower configuration is a blower with a circular housing to accommodate a rotating impeller. So a rotational engagement between the blower and the mask base may be preferred. The above described arrangements may be suitable for releaseably engaging the blower with the mask body or a frame of the patient interface. However, in some embodiments, the blower may be permanently attached to the mask body or frame, so that a user cannot remove the blower from the mask body or frame easily, or without tools, or without damaging or destroying the patient interface.

In some embodiments the blower may be mounted to the mask body from a rear side of the mask body. In some embodiments, the seal may be removable from the rear of the mask body, and the blower may be installed into the mask body when the seal is removed. Once the blower is mounted to the mask body, the seal may be attached to the rear of the mask body. The blower may clip into the mask body or be held by a retaining part or clip. In some embodiments, where the interface comprises a seal assembly comprising the face seal 110 and a clip for clipping the face seal to the mask body, the clip of the seal assembly may also function to retain the blower within or to the mask body. For example, the blower may be assembled to the mask body from a rear side of the mask body, and then the seal assembly comprising the seal and seal clip is attached to the rear side of the mask body. The clip of the seal assembly may hold the blower in place within or on the mask body. For example the blower may be sandwiched between the seal clip and the mask body. The blower may be assembled to the mask body via an outlet of the mask body.

A blower that may be assembled into the patient interface of FIGS. 2A to 2I is described with reference to FIGS. 3A to 3D. A blower suitable for attachment to the mask body comprises a blower housing or casing 152. In some embodiments the blower housing includes details for attaching the blower housing to the mask body. For example, as described above the blower housing may comprise one or more projections 133, to be received in a corresponding number of recesses 132 of the mask body. In some embodiments the blower housing may attach directly to the mask body. As described above, the blower 150 may be mounted to the mask body 120, 127 by a portion of the blower housing that is radially outside of and/or surrounding an impeller and impeller space of the blower. In some embodiments, the blower is mounted to the mask body via an outer perimeter or circumferential portion of the blower housing.

In some embodiments a pneumatic seal is created between the blower and the mask body. The mask body may have a low pressure side on an inlet side of the blower and a high pressure side on an outlet side of the blower. The inlet and outlet sides of the blower may be separated by a seal between the blower and the mask body, so that the only or predominant pneumatic connection between the low pressure side and the high pressure side of the mask body is via a flow path through the blower (described below). In some embodiments a resilient material may be provided on the blower housing. For example a resilient material may be over-moulded to the housing 152. The resilient material of the blower housing may form a seal against the mask body. Alternatively, the mask body may comprise a resilient material, for example over moulded to a surface of the mask body, to contact the blower housing to form a seal. The material of the seal may be integrally formed with the material of the cushion, in a single member over moulded to the mask body. In some embodiments a separate sealing member may be provided between the mask body and the blower, to form a seal between the body and the blower. In some embodiments an o-ring seal may be fitted to the blower or the mask body, to seal between the body and the blower. In some embodiments a pneumatic seal may be created between the blower and the mask body without a resilient material. For example, the blower housing and the mask body may be complementarily adapted to form a labyrinth type seal or tortuous path between the blower housing and the mask body.

In some embodiments a vibration isolation member may be provided between the blower and the mask body. In some embodiments the vibration isolation member may also form a pneumatic seal between the blower and the mask body. The vibration isolation member may be formed with the blower, the mask body, or may be a separately assembled part.

In some embodiments the mask body comprises one or more bias flow apertures to allow for bias flow venting of expelled breath. The bias flow apertures may be provided on the mask body on the outlet side of the blower. For example, bias flow holes may be provided in the area of the mask body identified by reference number 119 in FIG. 2A. In some embodiments the mask body is without bias flow apertures. In such an embodiment, the user may breath out into the mask and through the passageway of the blower, e.g. into the blower outlet 151 and out of the blower inlet 153, to vent from the mask, for example via the mask inlet 125. Such an arrangement may reduce a level of noise from the blower located within the mask body from reaching the user. In such an arrangement it is preferred that the interior space 112 is minimised.

Figure 3A:
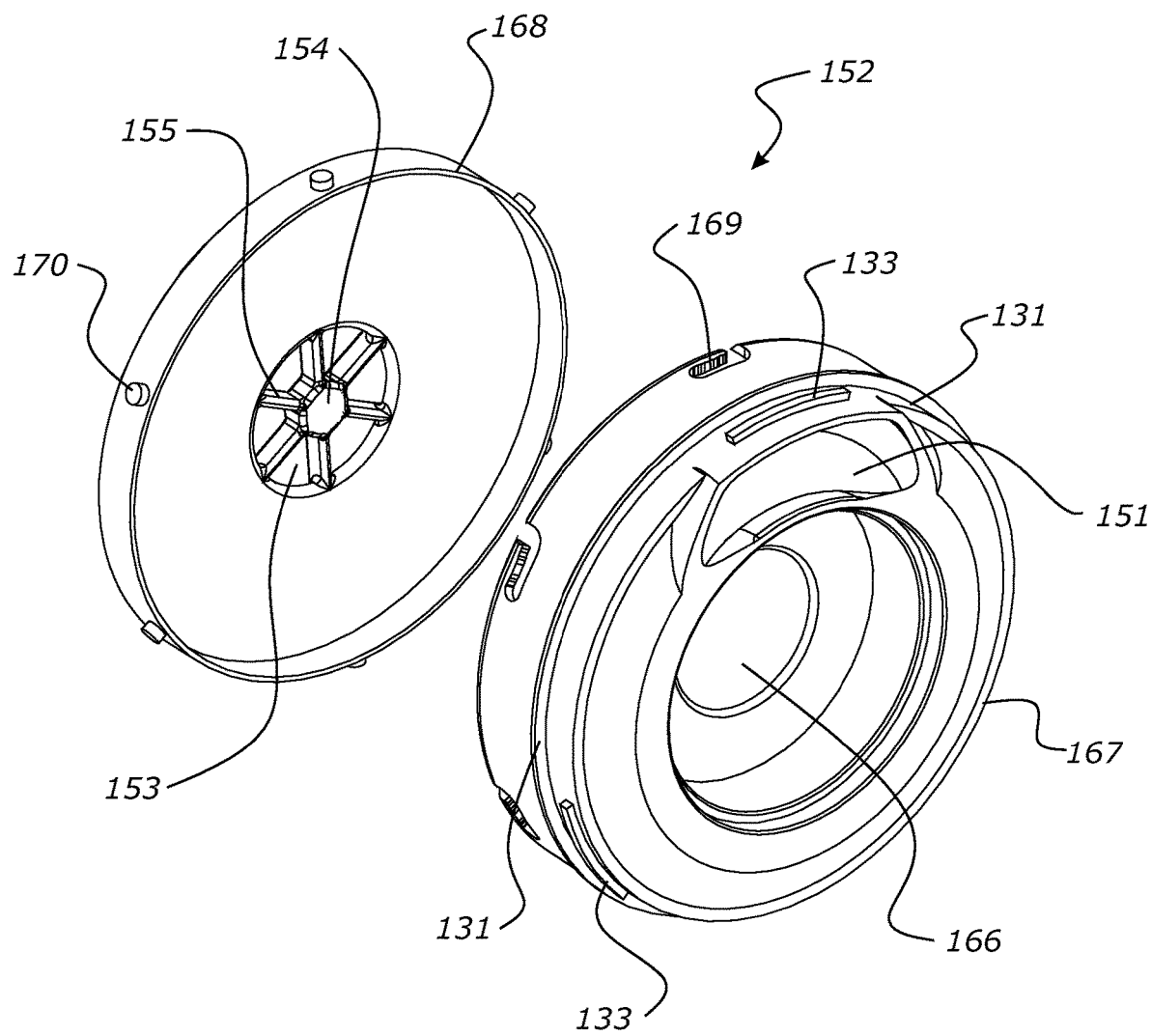
FIG. 3A is an exploded view of a housing of a blower of the patient interface of FIG. 2A, viewed from the rear and from above.
Figure 3B:
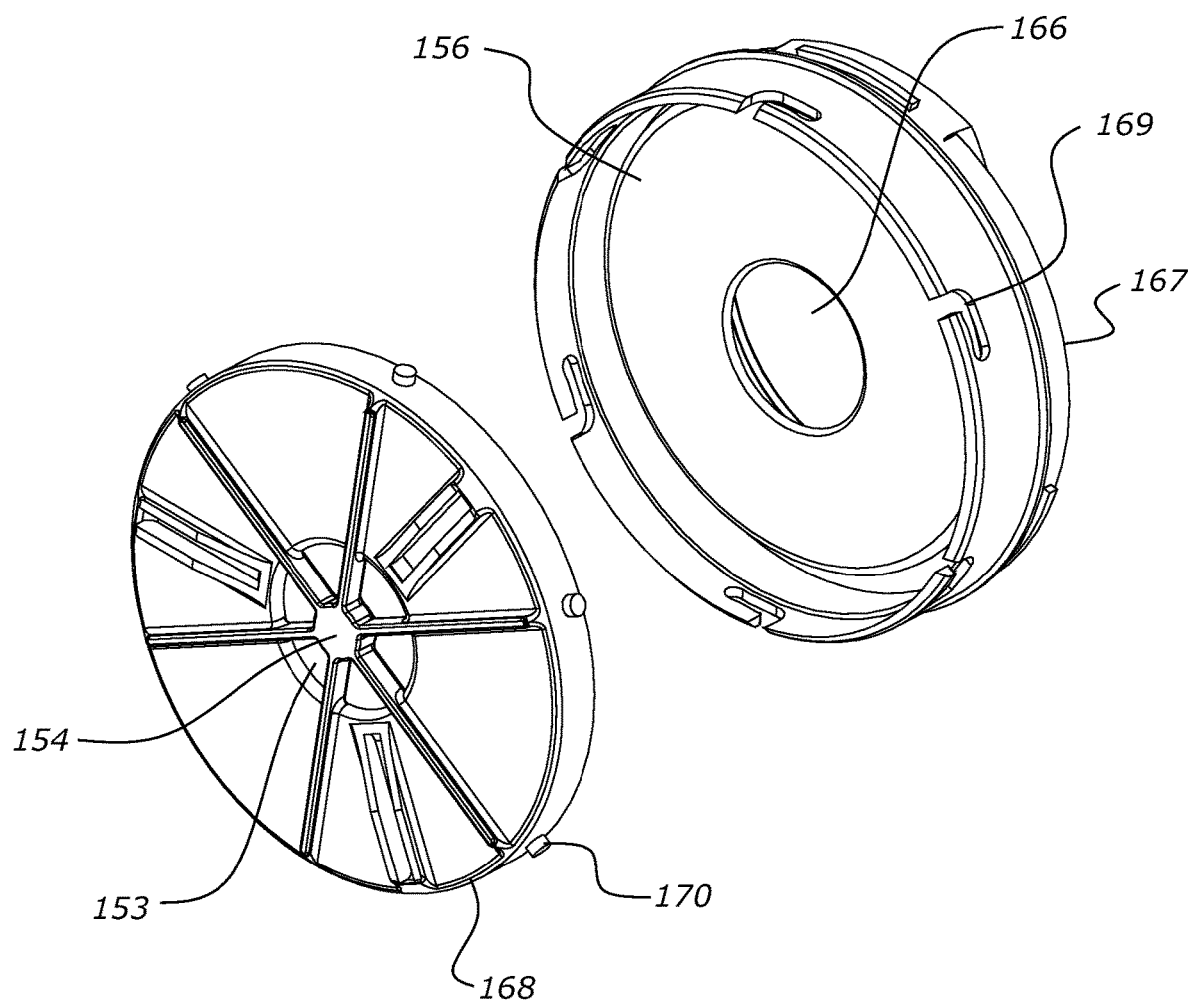
FIG. 3B is an exploded view of the housing of FIG. 3A, viewed from the front and from above.
Figure 3C:
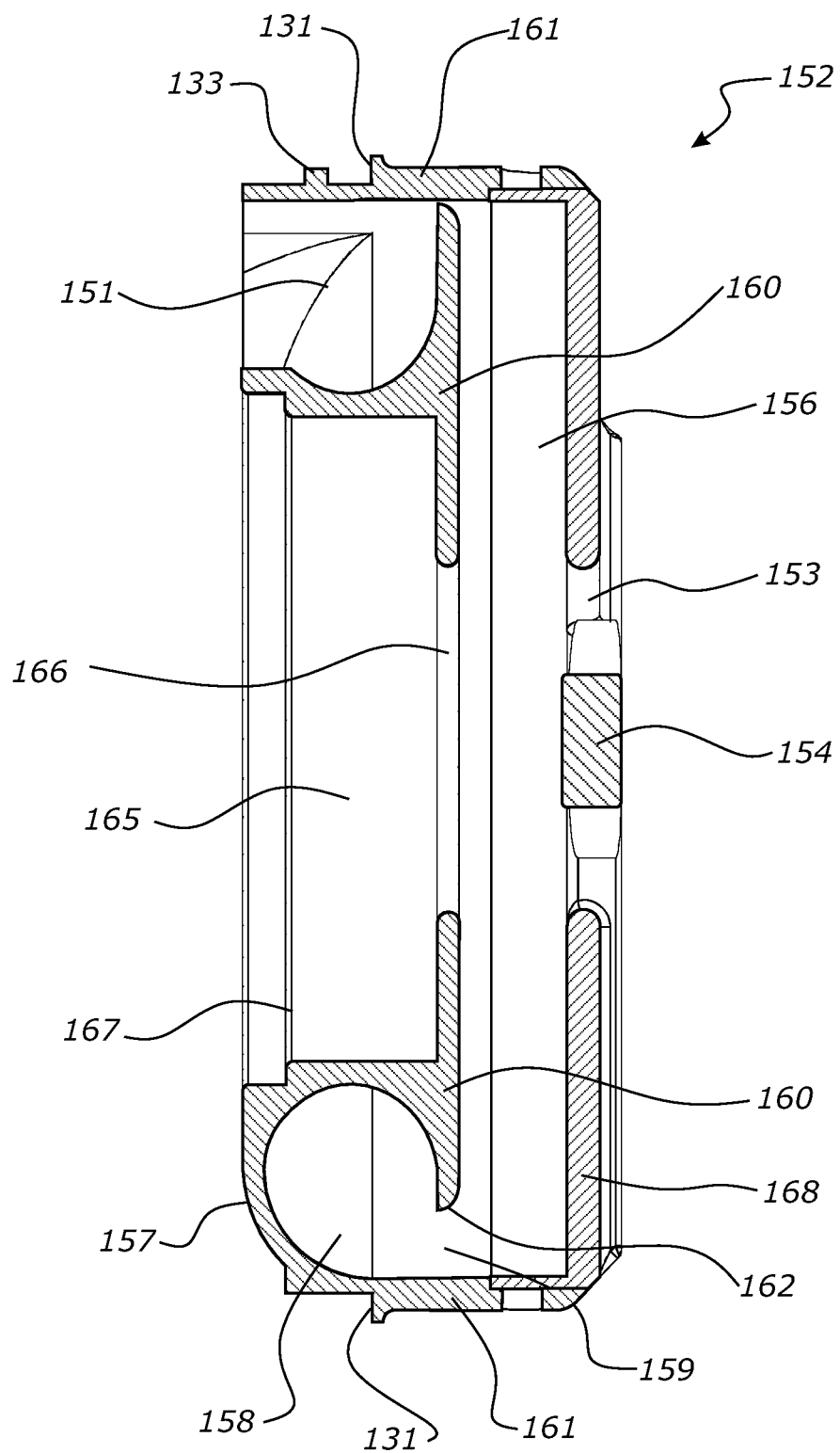
FIG. 3C is a cross sectional view on a centre line of the housing of FIG. 3A.

The housing is shown in exploded views in FIGS. 3A and 3B and in cross section in FIG. 3C. In some embodiments the blower housing 152 is circular to assist with a rotational engagement with the mask body, as described above. The blower housing has an inlet 153 through which an impeller of the blower draws air into the blower. In some embodiments the inlet is arranged approximately centrally at one end (an inlet end) of the housing. For example, in the illustrated embodiment the inlet is arranged centrally and comprises a number of apertures arranged around a central hub 154, the apertures separated by radial ribs or spokes 155. In the illustrated embodiment the apertures are segment shaped. In other embodiments the inlet may be a circular aperture, preferably located centrally on the housing.

The blower comprises an impeller housing providing an impeller space 156 for an impeller of the blower. Rotation of the impeller is driven by a motor of the blower. Rotation of the impeller within the impeller space draws air into the impeller space 156 via the inlet 153 of the blower. In some embodiments the blower housing 152 comprises the impeller housing. The inlet 153 is preferably located centrally with respect to a rotational axis 183 of the impeller.

The blower comprises a volute housing 157 providing a volute space 158. Typically a 'volute' in a pump is a curved funnel that increases in area towards an outlet of the pump. However, in this specification and claims, the term 'volute' should be interpreted broadly to mean a housing that receives air pumped by the impeller from the impeller space and in which the velocity of the air decreases to cause a high pressure. Thus the volute 157 is not necessarily volute-shaped.

In some embodiments the blower housing 152 comprises the volute housing 157. As illustrated by the example housing of FIGS. 3A to 3D, in some embodiments the volute space is annular. As the impeller rotates in the impeller space 156, the impeller draws air into the impeller space from the inlet 153 and forces air from the impeller space 156 into the volute space 158 via a passage 159 between the impeller space 156 and the volute space 158. The air collecting in the volute space passes from the volute housing via a blower outlet 151 and into the mask body or seal, for breathing by the user or patient.

In some embodiments, as illustrated in FIGS. 3A to 3D, the blower 150 has an axial outlet 151 located at an outlet end of the blower housing. The axial outlet is also visible in the end view of the patient interface with the seal removed, FIG. 2G. In some embodiments, the axial outlet directs air from the blower axially into the mask body and/or interior 112 of the seal, towards the user's face. In some embodiments the blower outlet is axial and located at a radial position that is radially outwards of the blower inlet. As illustrated in FIGS. 2C to 2G, in some embodiments the blower axial outlet is positioned at an upper or '12 o'clock' position within the mask body. Alternatively, in some embodiments the blower axial outlet 151 is positioned at a lower or '6 o'clock' position within the mask body, or may be at other circumferential positions, for example located towards a left or right hand side of the mask body. In some embodiments the outlet spans a circumferential angle of 10 to 90 degrees, or 20 to 80 degrees.

Figure 3D:
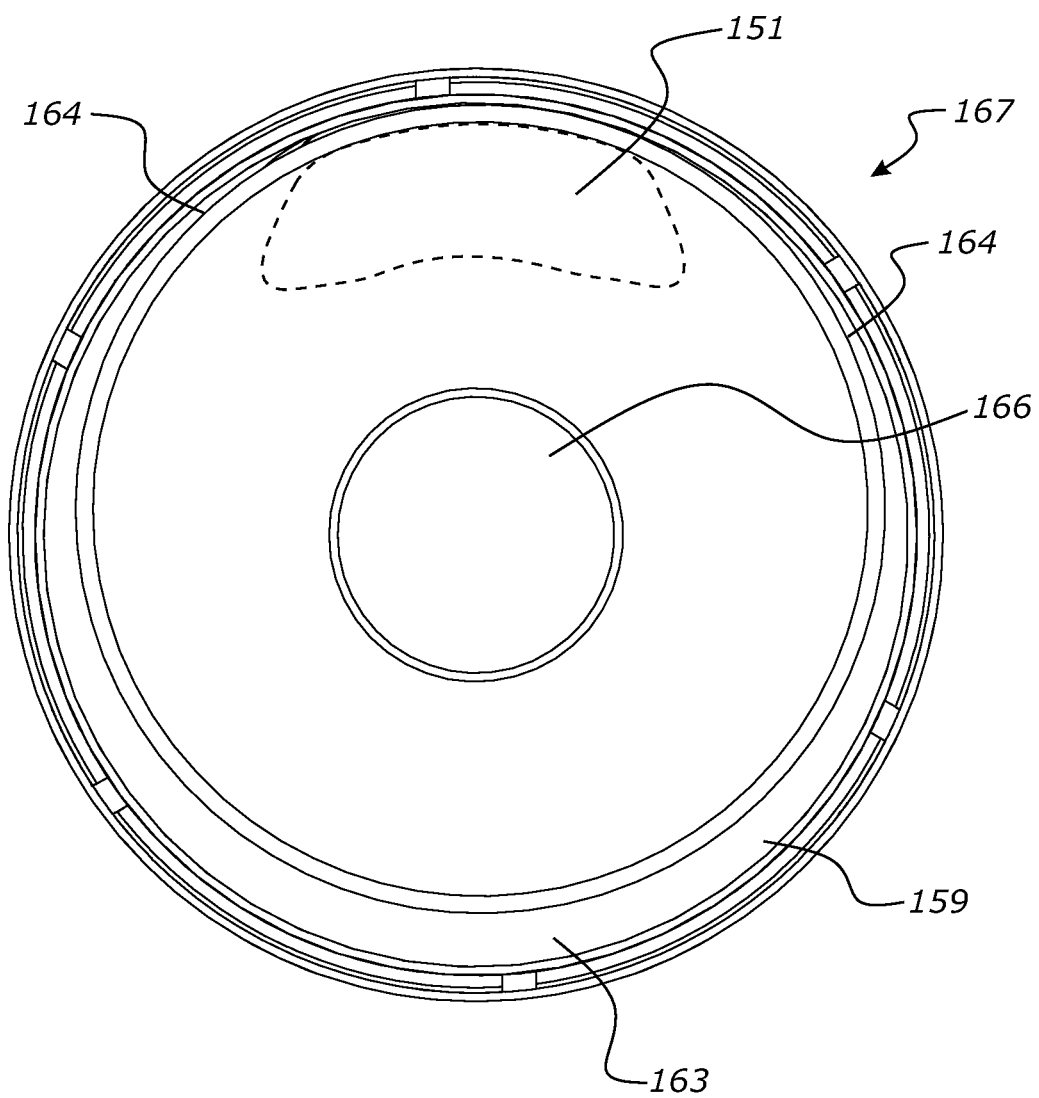
FIG. 3D is a front view of a housing part of the housing of FIG. 3A.

In some embodiments the impeller space 156 and the volute space 158 are separated by a dividing wall. In some embodiments the impeller space is separated from the volute space by a dividing wall 160 of the housing. In some embodiments the passage 159 between the impeller space 156 and the volute space 158 is an aperture in the dividing wall. As shown, in some embodiments the dividing wall does not extend fully to a side wall 161 of the volute housing, and the passage is a gap 159 between an edge 162 of the dividing wall 160 and the side wall 161. The side wall may be a circumferential side wall of the blower housing. In some embodiments the passage 159 is crescent shaped. In some embodiments, the gap 159 between the dividing wall and the side wall is crescent shaped. For example, as best shown in FIG. 3D, the gap 159 is crescent shaped, tapering on either side of a widest point 163 of the passage to a narrow point or narrow points 164 either side of the widest point. Preferably the widest point 163 is diametrically opposite the outlet 151 of the blower, as shown in FIG. 3D (outlet shown in dashed lines, being hidden from view). The passage 159 between the impeller space and the volute space is radially outside the blower inlet 153. In some embodiments the blower inlet may be the patient interface inlet, for example where the mask body does not comprise a cover.

The blower comprises a motor for driving rotation of the impeller. In some embodiments the housing provides a motor space 165, for housing the motor within the housing of the blower. In some embodiments the volute space 158 extends around the motor space 165. In other words, the motor is located radially inside of the annular volute space 157. In some embodiments the motor is located radially inside of the annular volute space. An aperture 166 is provided between the motor space and the impeller space so that a shaft of the motor or impeller can extend between the impeller and the motor to couple the impeller to the motor. Positioning the motor radially inside of the annular volute space achieves a flat (small axial length) blower configuration.

In some embodiments the patient interface may comprise one or more electronic circuit boards, for example the blower may include motor control electronics. In some embodiments, the electronics may be provided remotely from the patient interface. In such an embodiment, a cable 60 to the patient interface may provide communications and motor control current and/or voltage from the remote motor controller to the motor.

In some embodiments the blower housing 152 comprises two parts, a housing 167 and a cap 168, wherein the volute housing 157 is formed in the housing 167 and the cap 168 attaches to an end of the housing 167 to define the impeller space 156 together with the housing 167. In some embodiments the inlet 153 is formed in the cap. The cap may be fitted to the housing by a screw thread or any other suitable fitment arrangement. For example, in the illustrated embodiment the housing comprises circumferentially extending recesses 169 each with a longitudinally extending portion, for receiving radial pins 170 on the cap, so that the cap may be fitted to the housing in a push and turn movement (a bayonet fitting). The illustrated example comprises 6 pins 170 and corresponding recesses 169, however, more or less recesses and pins may be provided. In the example the cap requires approximately a 10 degree turn to fit the cap to the housing. In some embodiments the cap may be removed from the housing so that a user can access the inside of the housing, for example for cleaning. In some embodiments the cap may be fixed to the housing against removal by a user. For example the cover may be welded to the housing. Other attachment methods may be used, for example screw fasteners may attach the cap to the housing. The cap 168 may form a cover of the patient interface, for example in an embodiment comprising a mask body without a cover for covering the inlet side of the blower.

A further embodiment for a patient interface 200 with blower is illustrated in FIGS. 5A to 5H, with a corresponding blower housing 252 illustrated in FIGS. 6A to 6D. Parts that are similar or the same as parts described with reference to FIGS. 2A to 3D are referenced by the same referenced numerals.

The embodiment of FIGS. 5A to 5H comprises a mask body 120, similar to the mask body described above with reference to the embodiment of FIGS. 2A to 2I. The embodiment of FIGS. 5A to 5H further comprises a cushion frame 137. In the illustrated embodiment, the cushion frame 137 is integrally formed with the cushion 110 in a cushion module 138. The cushion frame 137 is preferably relatively rigid and supports the relatively soft and compliant cushion 110, and attaches the cushion 110 to the mask body 120. The cushion module 138 releasably attaches to the mask body 120. In some embodiments, as illustrated, the mask body 120 and cushion frame 137 are both without a vent path, e.g. bias vent apertures, such that the user must exhale through the blower 250. The mask body 120 comprises an open rear through which the blower 250 is mounted to the mask body 120. The blower may be received in and surrounded by a perimeter of the open rear of the mask body 120. The blower may be completely bounded by the perimeter of the open rear of the mask body. The cushion module may attached to the perimeter of the open rear of the mask.

In the embodiment of FIGS. 5A to 5H the blower 250 comprises a radial outlet. Comparison of FIGS. 3A to 3D with FIGS. 6A to 6D illustrating blower housing 252 of blower 250 shows that the blower inlets 153, impeller spaces 156, volute spaces 158, passages between the impeller space and volute space, and motor spaces of the two blowers 150, 250 are of the same configuration. A difference in flow path through the blower 250 of patient interface 200 and the flow path through the blower 150 of patient interface 100, is that the blower 250 of patient interface 200 has a radial blower outlet 251, whereas the blower 150 of patient interface 100 has an axial blower outlet 151 as described above. The blowers 150, 250 may be used interchangeably e.g. swapped between the two illustrated embodiments of FIGS. 2A to 2I and 5A to 5H.

Figure 5A:
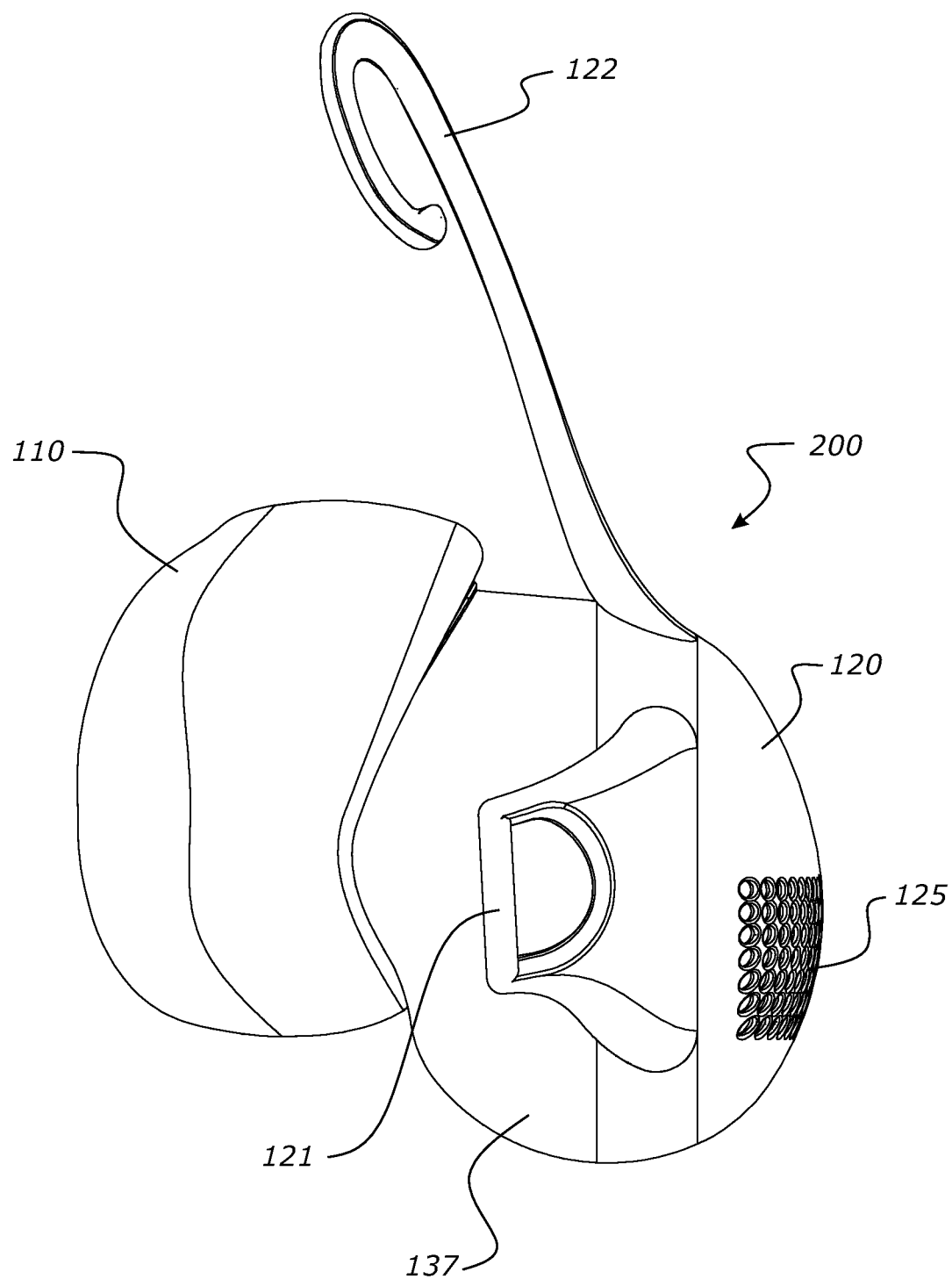
FIG. 5A side view of another patient interface.
Figure 5B:
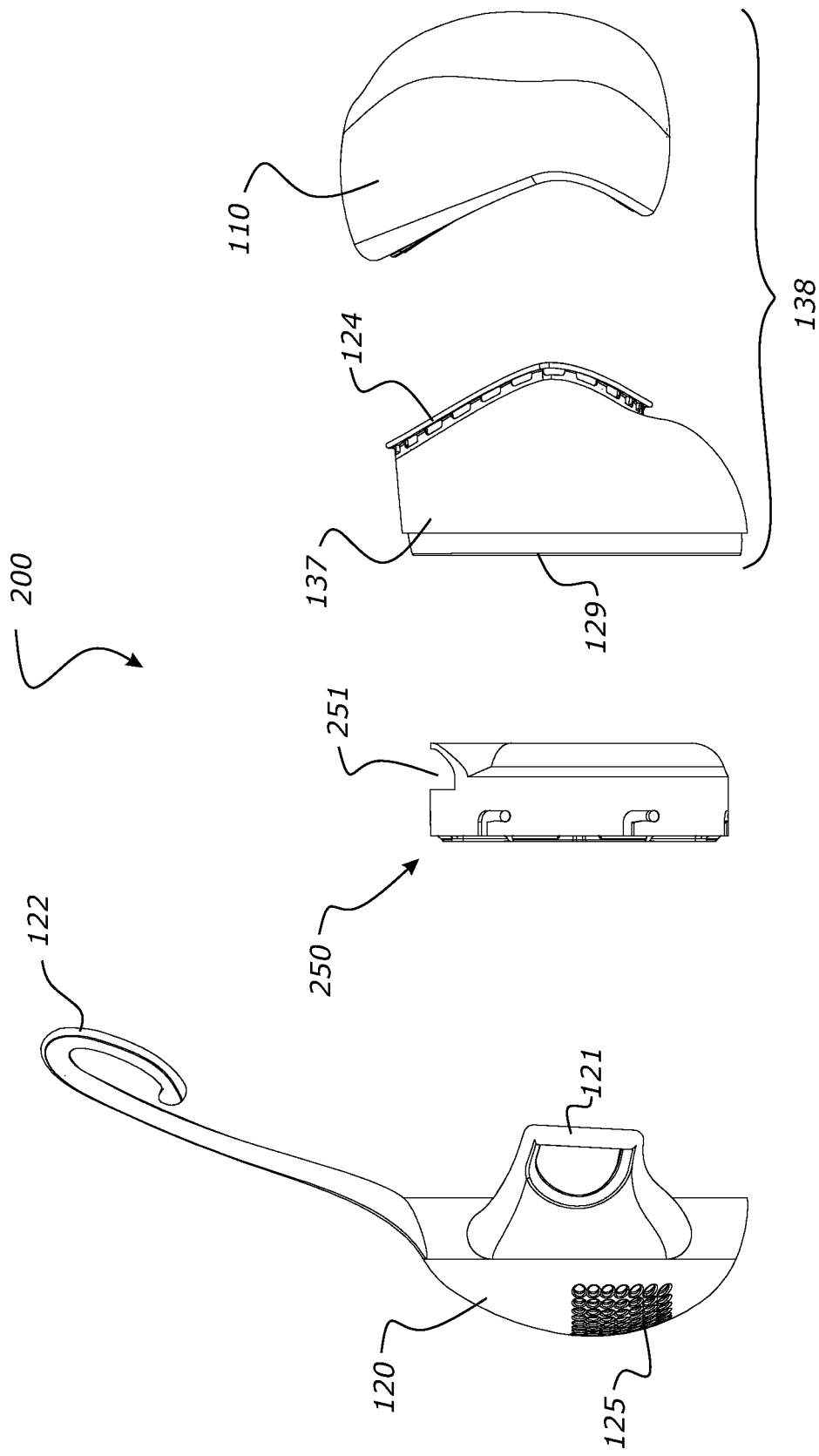
FIG. 5B is an exploded side view of the patient interface of FIG. 5A.
Figure 5C:
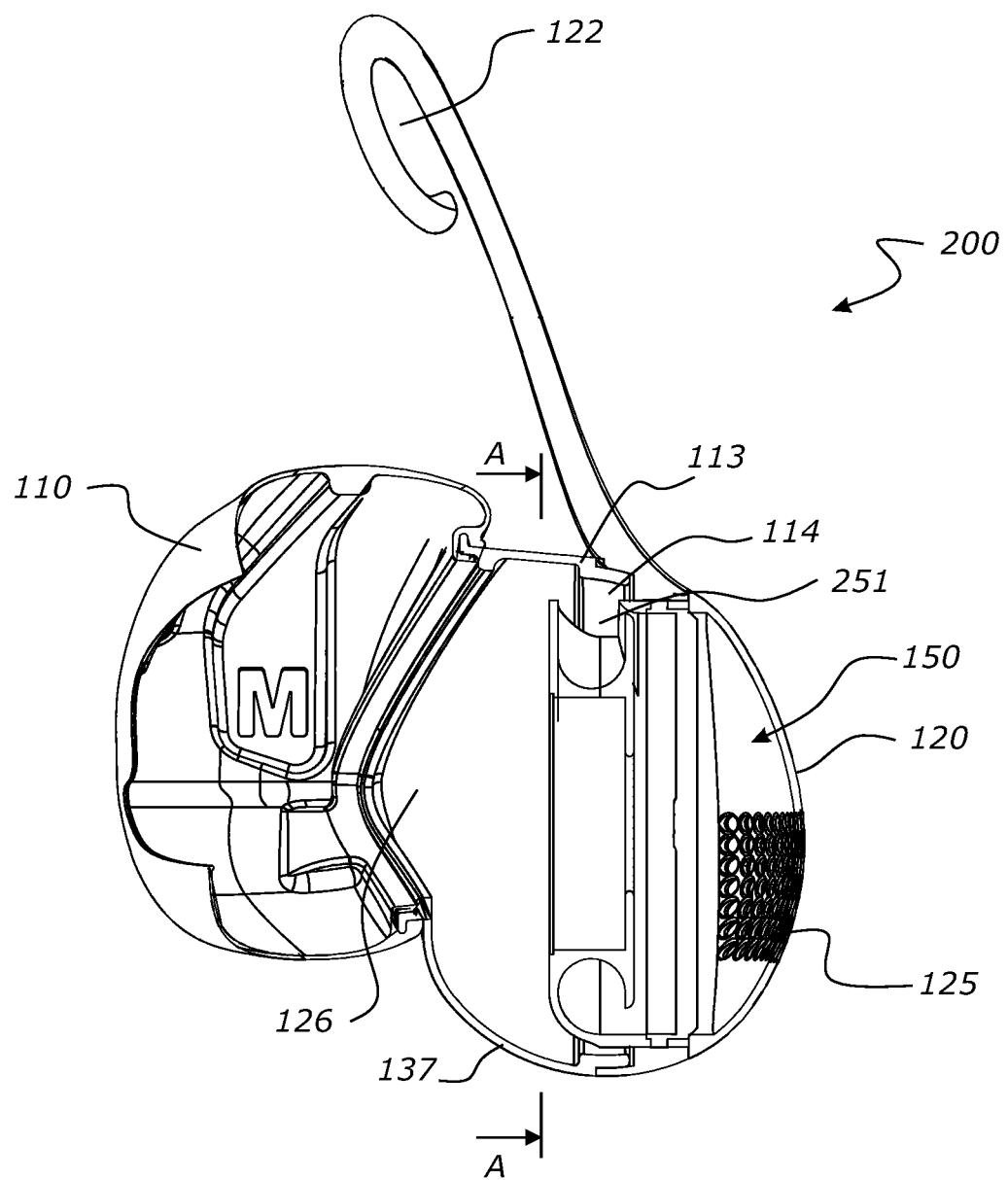
FIG. 5C is a cross sectional view on a centre line of the patient interface of FIG. 5A.
Figure 5D:
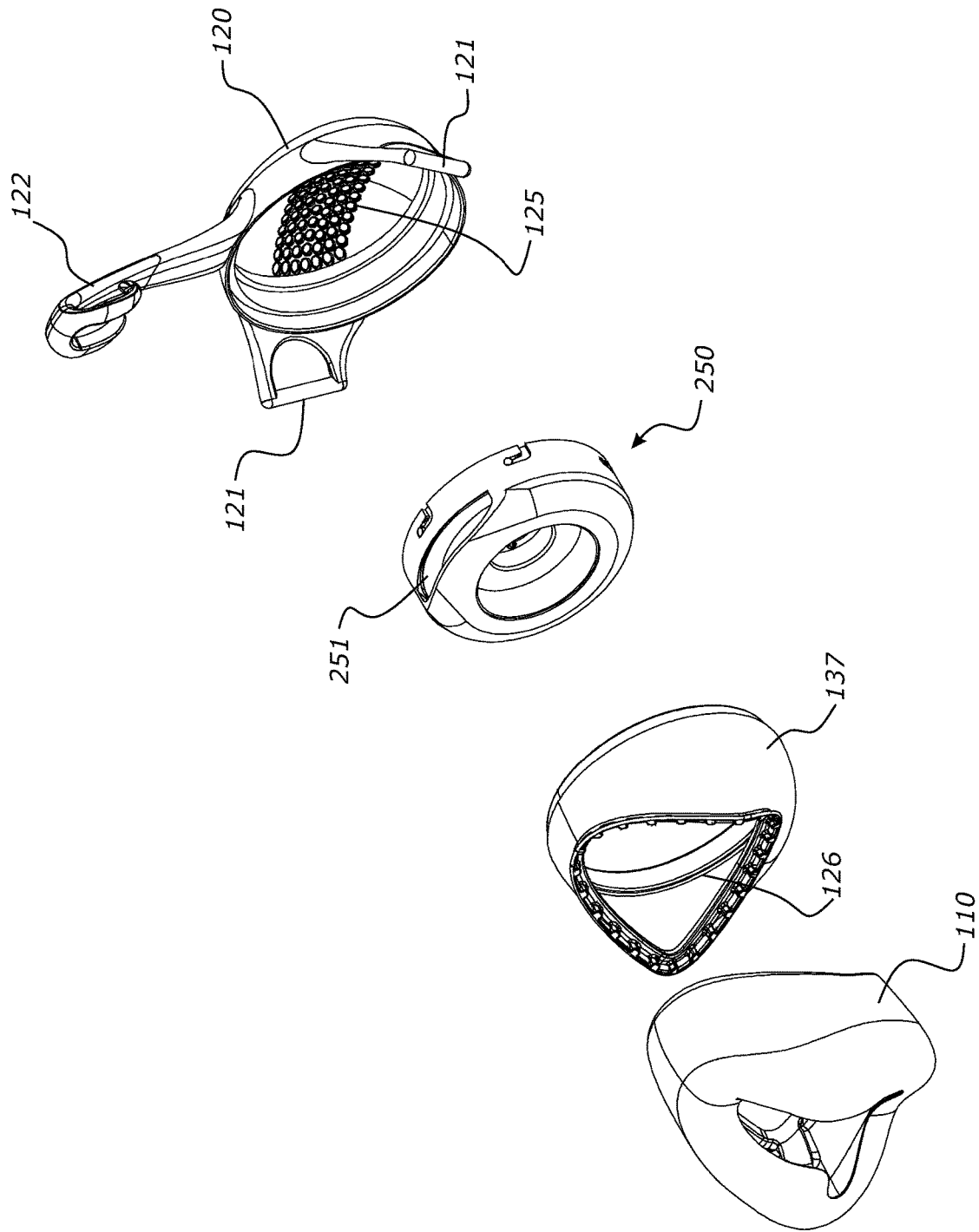
FIG. 5D is an exploded view, from the rear and from above, of the patient interface of FIG. 5A.
Figure 5E:
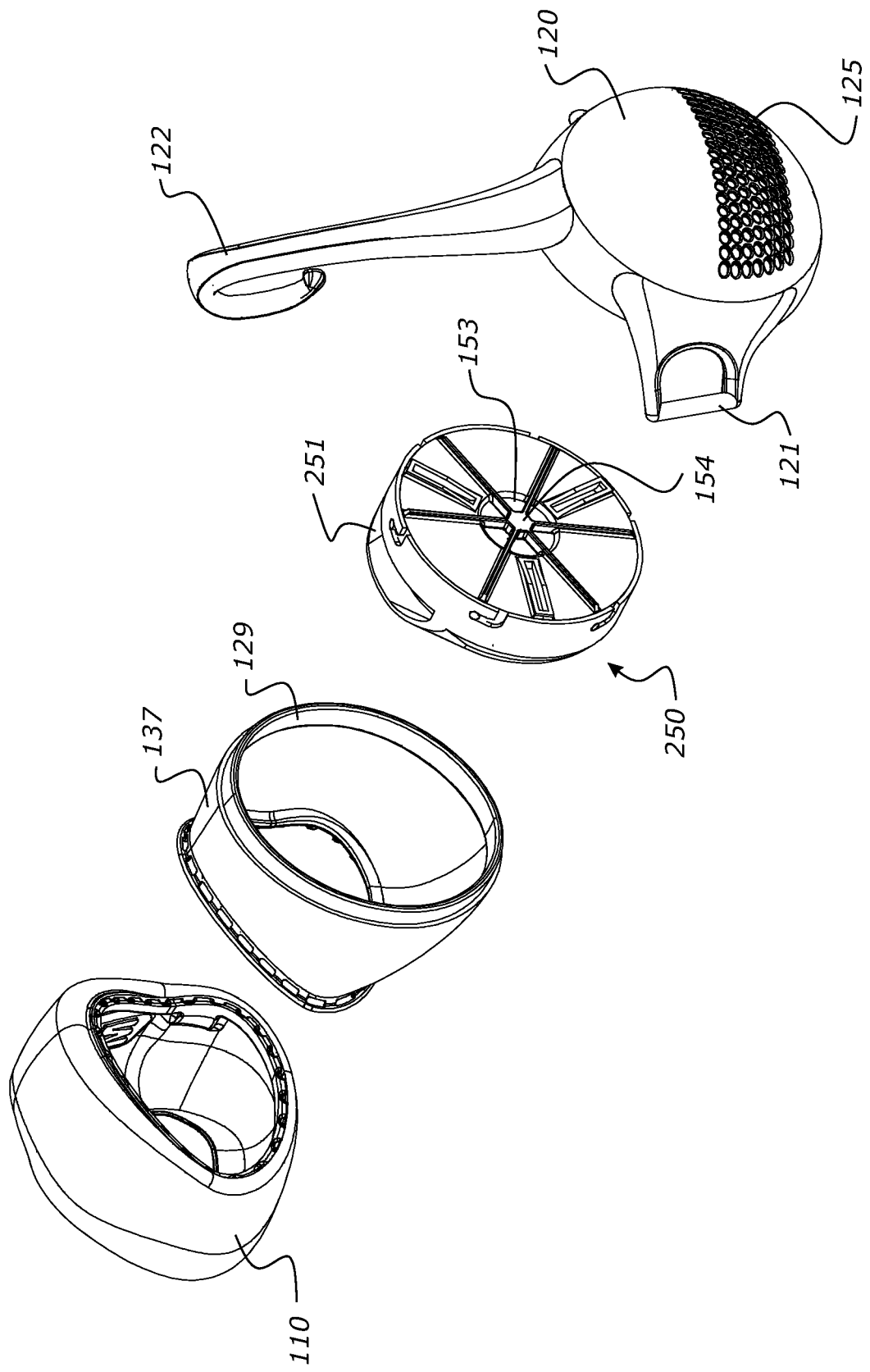
FIG. 5E is an exploded view, from the front and from above, of the patient interface of FIG. 5A.
Figure 5F:
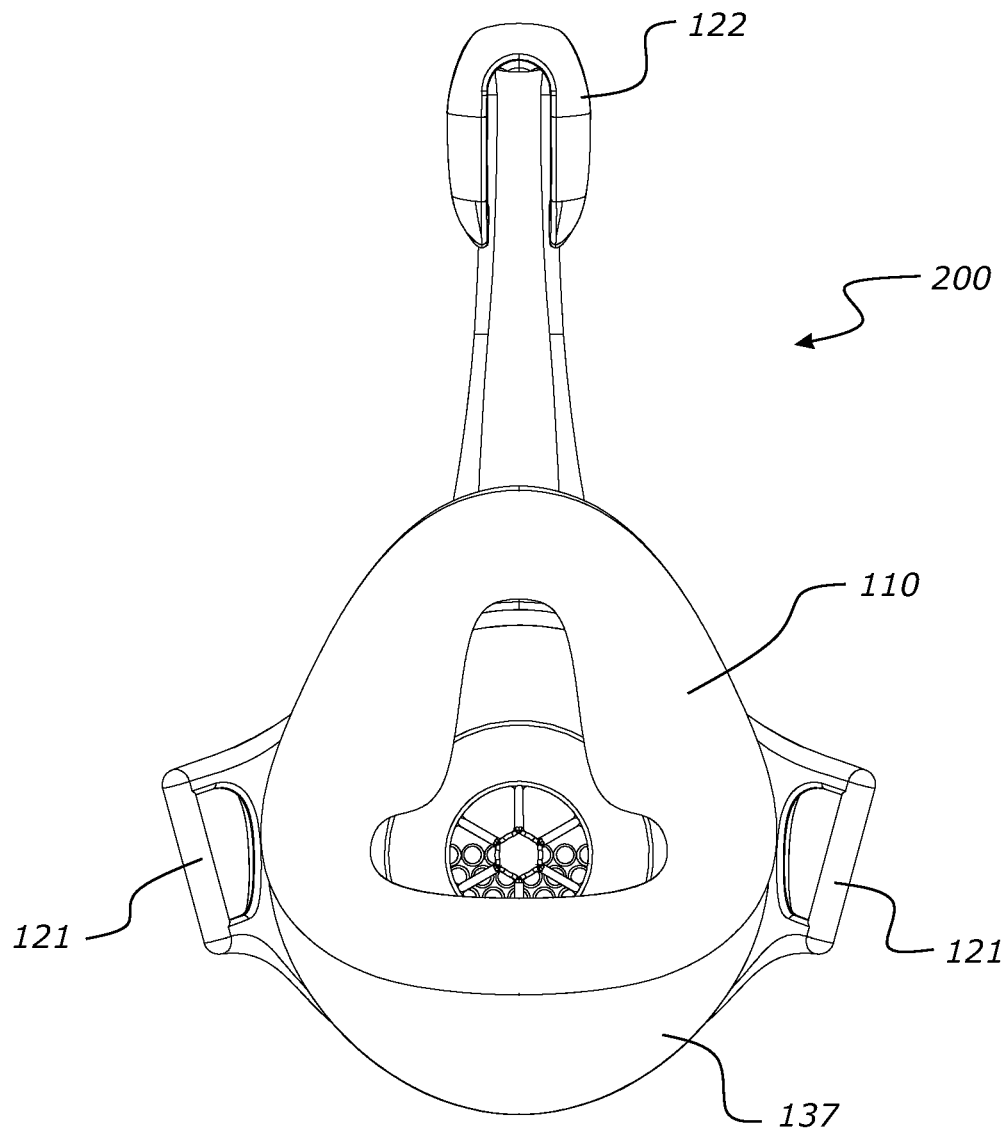
FIG. 5F is a rear view of the patient interface of FIG. 5A.
Figure 5G:
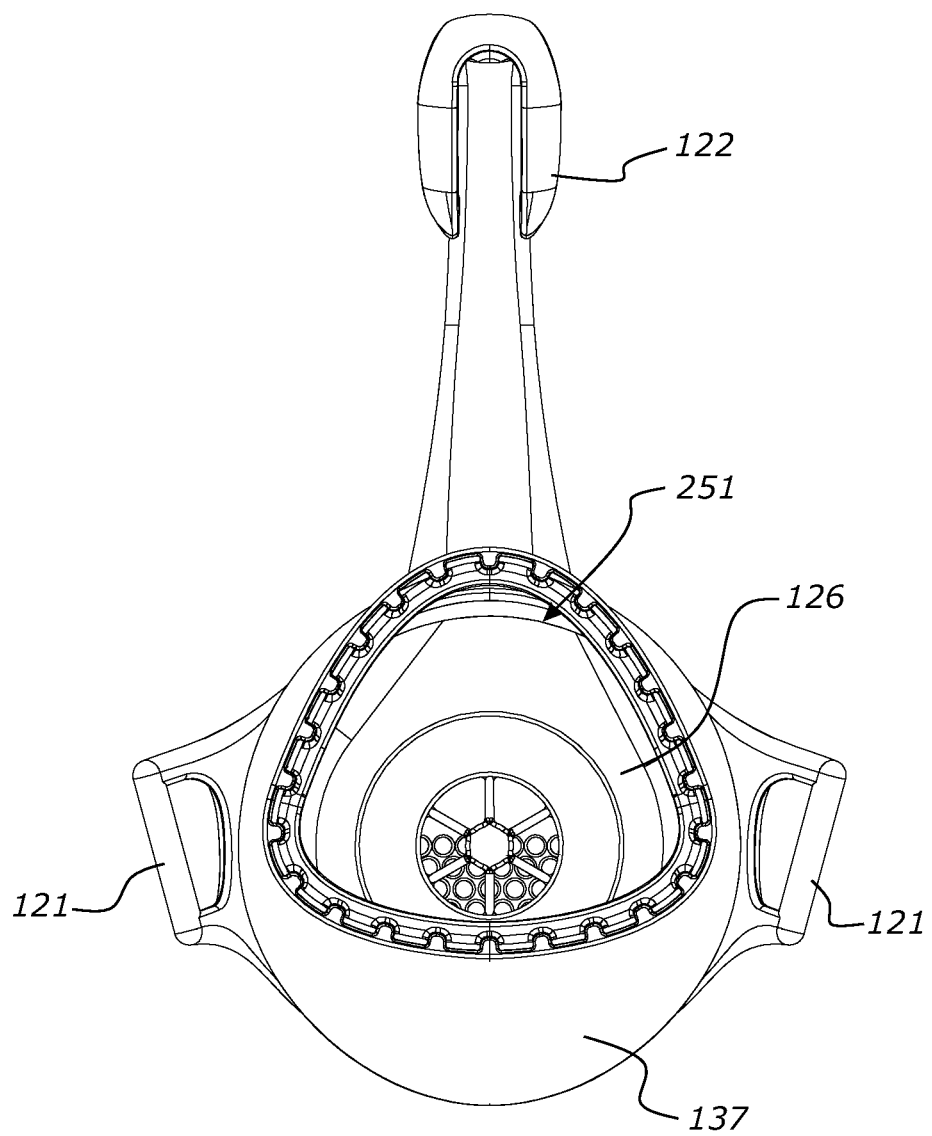
FIG. 5G is a rear view of the patient interface of FIG. 5A and with a seal of the interface removed from the view.
Figure 5H:
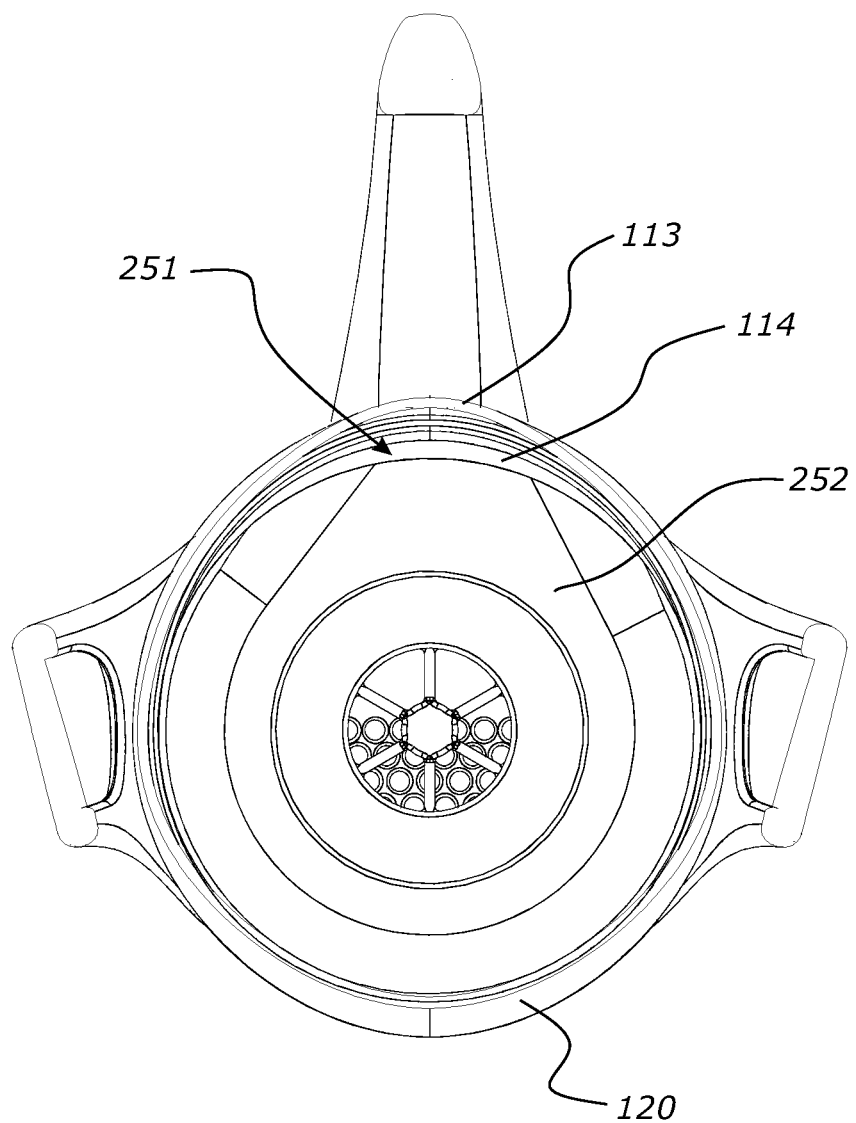
FIG. 5H is a sectional view of the patient interface of FIG. 5A on line A-A in FIG. 5C.
Figure 6A:
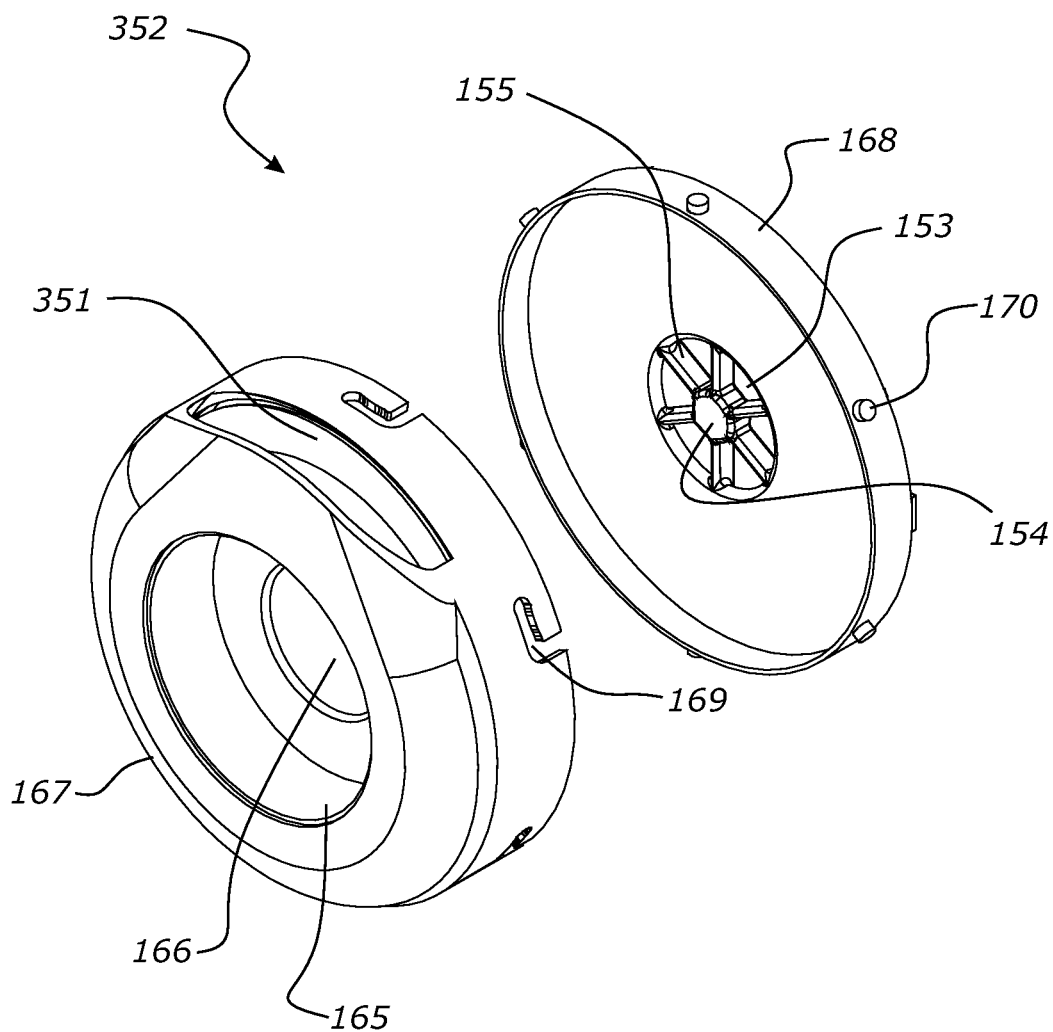
FIG. 6A is an exploded view of a housing of a blower of the patient interface of FIG. 5A, viewed from the rear and from above.
Figure 6B:
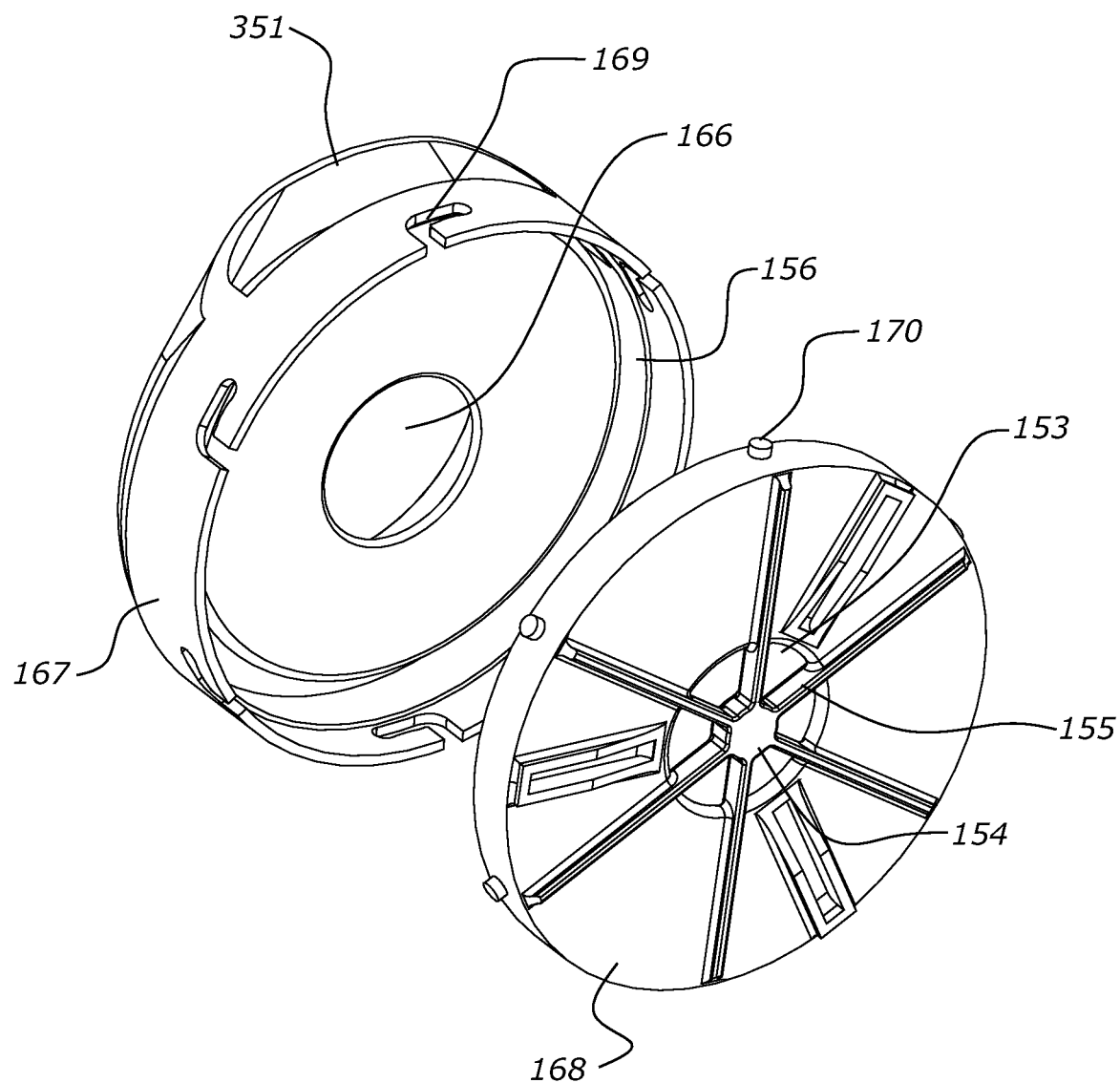
FIG. 6B is an exploded view of the housing of FIG. 5A, viewed from the front and from above.
Figure 6C:
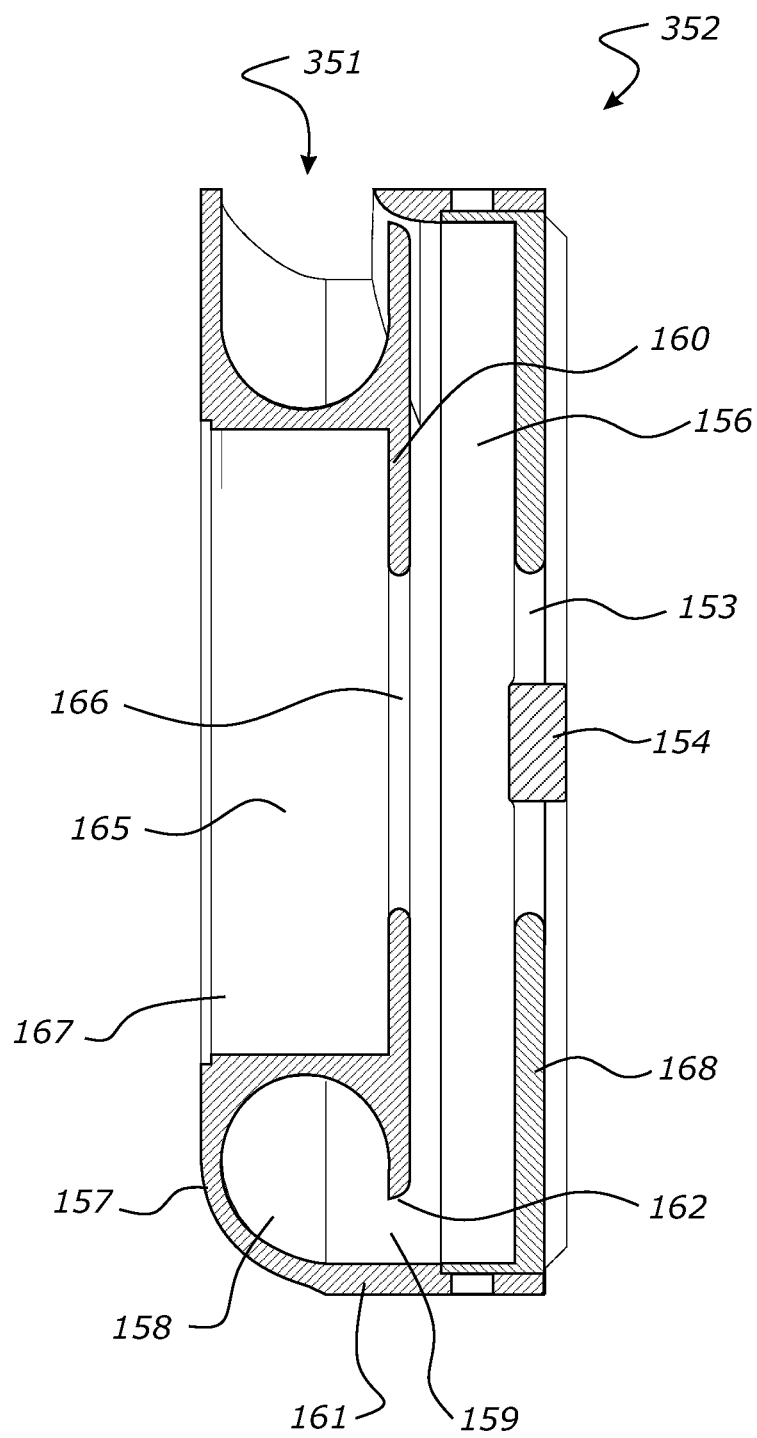
FIG. 6C is a cross sectional view on a centre line of the housing of FIG. 5A.
Figure 6D:
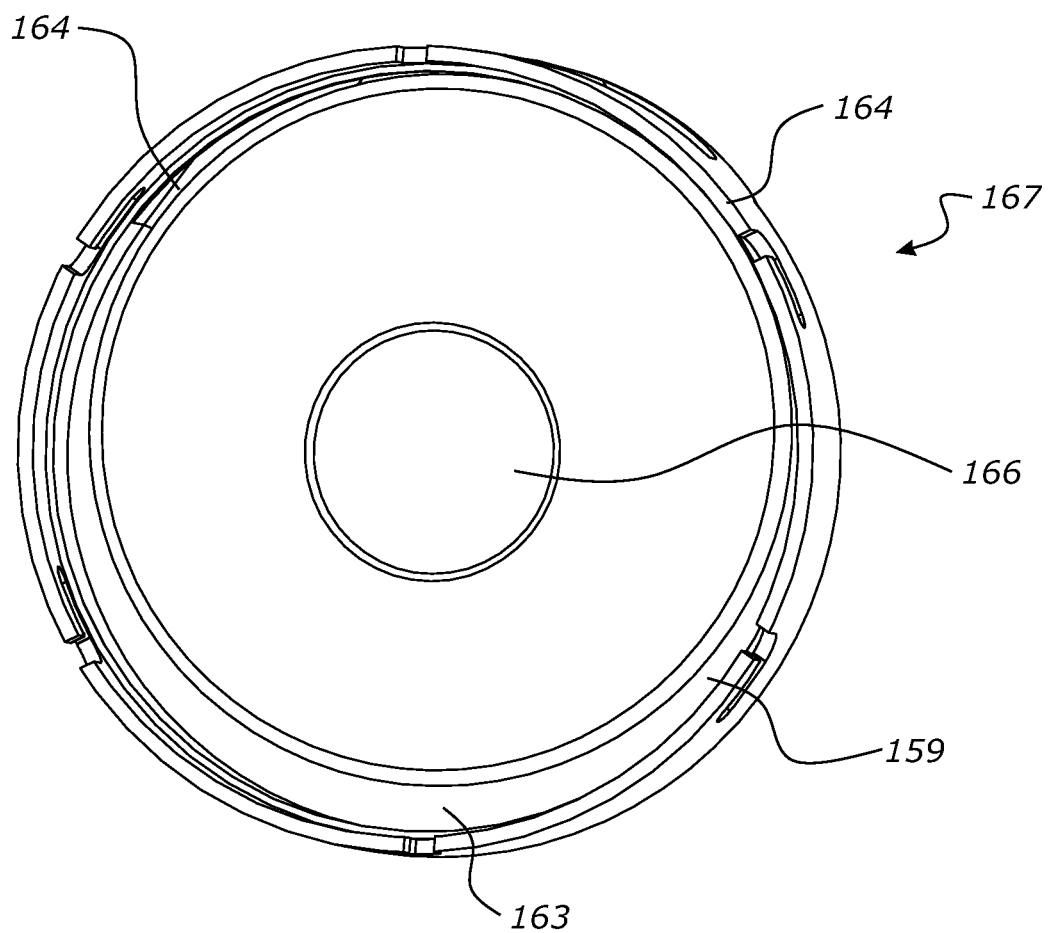
FIG. 6D is a front view of a housing part of the housing of FIG. 5A.
Figure 7A:
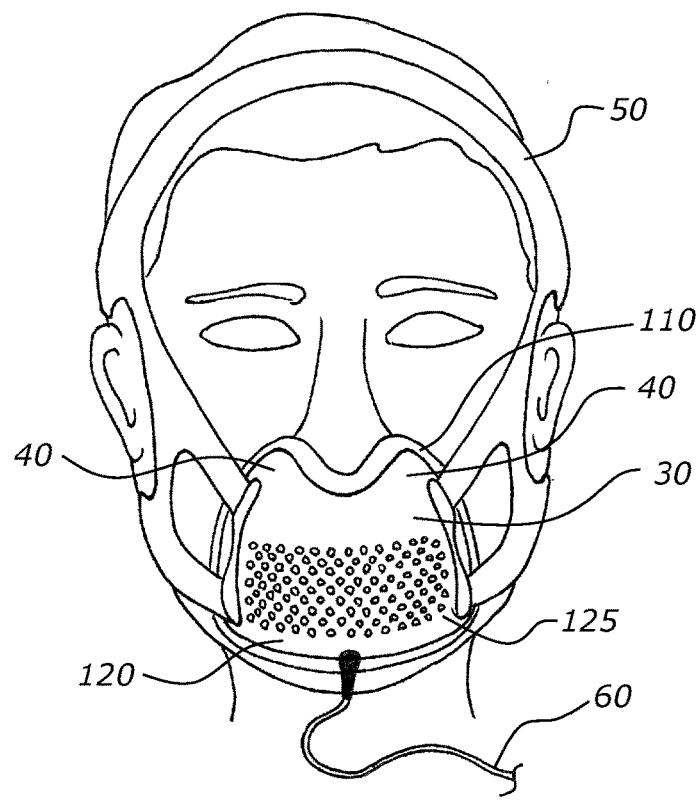
FIGS. 7A and 7B are front and side views of a user wearing a patient interface comprising a blower.
Figure 7B:
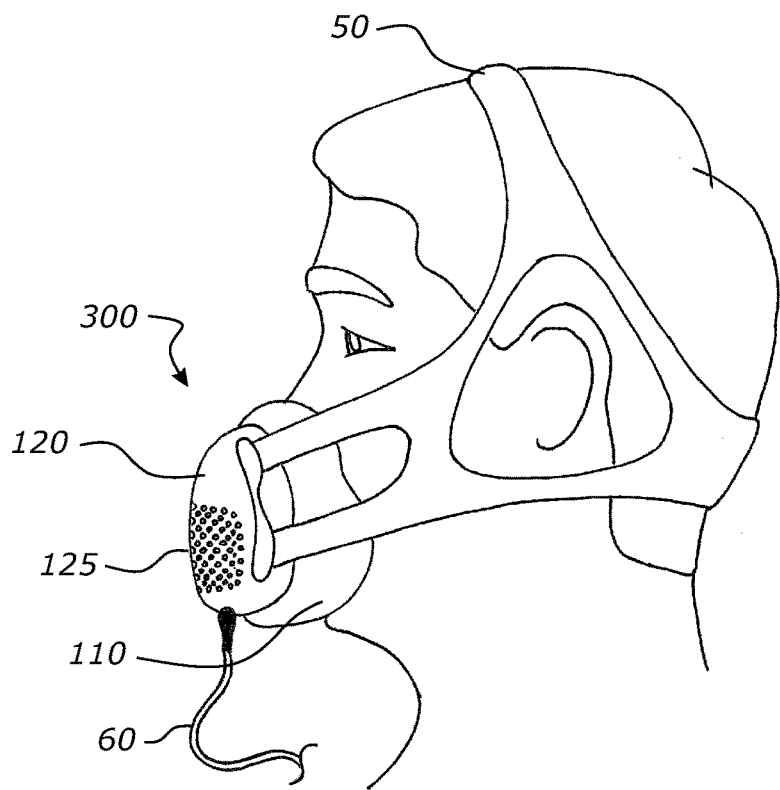

As best shown in FIG. 5C, in some embodiments, the radial outlet 251 directs the blower output laterally with respect to the user's face, towards a side wall 113 of the mask body 120 or the cushion frame 137. As shown in FIGS. 5C and 5H, in some embodiments the cushion frame is shaped so that the radial outlet is positioned radially inwards from the side wall 113 of the mask body 120 or frame 137 so that there is a gap 114 between the radial outlet 251 and the side wall 113. By directing the flow from the blower from a radial oriented outlet 251 laterally to the user's face into the inside of the mask base or mask seal, flow from the blower may be diffused, or flow speed into the patient's airways may be reduced. In some embodiments, blower radial outlet is positioned at an upper or '12 o'clock' position within the mask body, for example as shown in FIGS. 5B to 5H. Alternatively, in some embodiments the blower radial outlet 151 is positioned at a lower or '6 o'clock' position within the mask body, or may be at other circumferential positions, for example located towards a left or right hand side of the mask body. In some embodiments the radial outlet spans a circumferential angle of 10 to 90 degrees, or 20 to 80 degrees.

Figure 4:
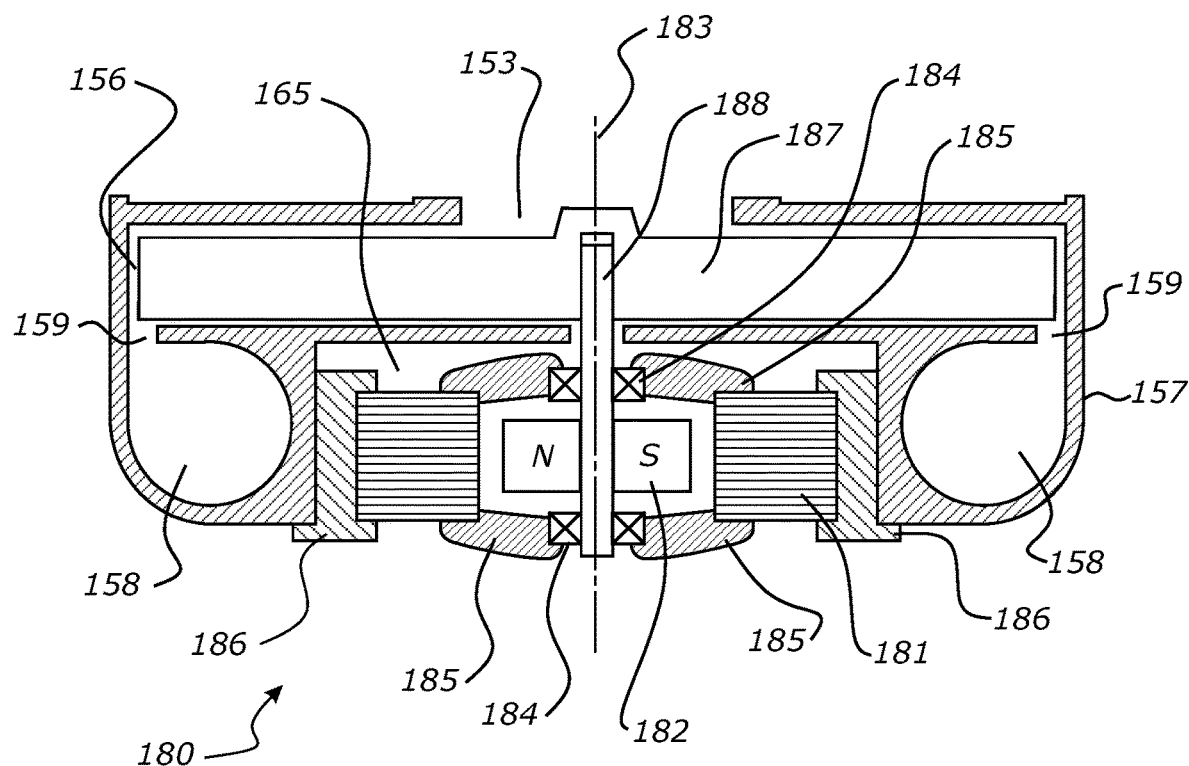
FIG. 4 is a cross section of a blower illustrating a possible motor configuration.

The motor and impeller is omitted from FIGS. 2A to 3D and FIGS. 5A to 6D. However, a possible motor configuration for blowers 150, 250 is illustrated in FIG. 4. The motor 180 comprises a stator 181 and a rotor 182. Preferable the stator is fixed to the housing against rotation. In some embodiments the rotor is located inside the stator. Alternatively an inside stator outside rotor configuration may be used. The rotor may comprise permanent magnets to form rotor poles and the stator wire windings to form stator poles. The rotor is rotationally supported for rotation about an axis 183 on bearing elements 184, which may comprise an inner and outer race with ball or roller elements in between, or plain bearings or other suitable bearing arrangement. In some embodiments, as shown, the bearing elements may be supported by the stator 181, for example via soft mounts 185. In some embodiments the stator is supported by the housing via a soft mount 186 or mounts. The impeller 187 is coupled to the rotor, for example via a shaft 188, for rotation on the rotational axis 183 of the rotor and impeller. Preferably the inlet is concentric with the rotational axis. The impeller may be rotationally supported at an inlet end, for example by a bearing element located at a hub of the housing (e.g. hub 154 shown in FIG. 3A to 3C). The bearing element at the hub may support the impeller both rotationally and axially. In the embodiment of FIGS. 2A to 2I, the blower is arranged so that the motor 180 is positioned (in the motor space 165) at an outlet end of the blower, opposite an inlet end of the blower. The blower outlet 151 is radially outside the motor 180.

The soft or compliant mounts 185 are vibration isolation members to isolate vibration of the rotating impeller and impeller shaft from the stator 181. The soft or compliant stator mount or mounts 186 isolate vibration of the stator from the blower housing or stator support caused by rotation of the impeller. In some embodiments the motor may comprise the soft mounts for the bearings and without a soft mount or mounts between the stator and the blower housing, or the motor may comprise the soft stator mounts 186 and without soft mounts 185 for the bearings. In some embodiments the blower may also comprise a soft mount or vibration isolating means between the blower housing and the mask body 120, 127 or the cushion frame 137. However, in some embodiments, the vibration isolation members 185 and/or 186 are adapted to reduce vibration to satisfactory levels such that no vibration isolation member is required between the blower 150, 250 and the mask body 120, 127 or cushion frame 137.

Figure 2I:
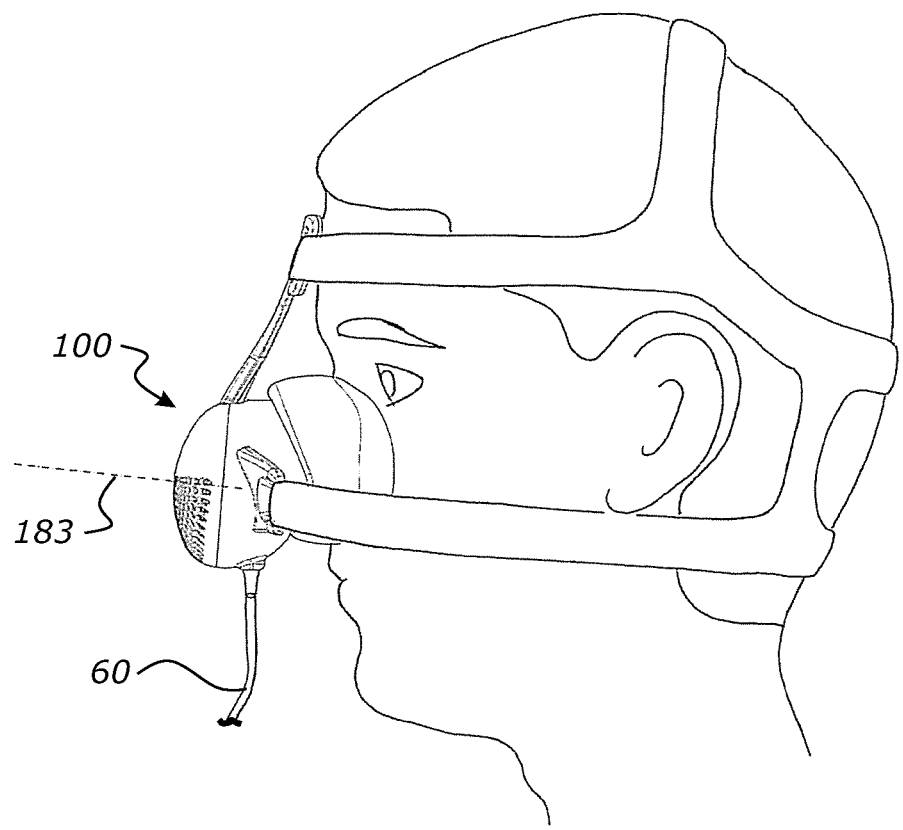
FIG. 2I is a side view of a user wearing the patient interface of FIG. 2A. The interface positions a blower in front of the user's face and with a rotational axis of an impeller of the blower arranged approximately perpendicular to the user's face.

As shown in FIG. 2C and in FIG. 2I, in some embodiments the blower is arranged within the patient interface with the rotational axis 183 of the motor and impeller approximately perpendicular to the user's face or user's coronal plane or extends into the user's face. In some embodiments, the diameter or overall lateral dimension of the blower is substantially larger than an axial length of the blower. For example, the blower housing of FIGS. 3A to 3D has an outer diameter of about 55 mm and an axial length of about 20 mm Thus the axial length is about one third of the outer diameter of the blower. Preferably the blower is configured to be flat against the user's face, or to not extend far from the user's face. By arranging the rotational axis to be approximately perpendicular to the user's face, the blower is arranged in a substantially flat configuration near to the user's face. With the patient interface 100, 200, 300, 400 positioned for use on the user's face and with the user in a standing position, the axis 183 is approximately horizontal, as shown in FIG. 2I. In some embodiments, the rotational axis 183 extends through the user's nose or mouth, or a region in between the user's nose or mouth, as shown in FIG. 2I. In some embodiments a general plane of the impeller is approximately parallel to a general plane of the user's face or to the user's coronal place. Preferably the blower is configured to have a minimum axial length (in the direction of the rotational axis), from the blower inlet to the blower outlet, so that the patent interface has a low profile on the user's face. In a preferred embodiment, the diameter of the impeller is significantly larger than the axial length of the impeller. The diameter of the impeller largely determines the overall size of the blower housing. By having the impeller rotational axis pointing towards the users face, the impeller diameter is arranged alongside (approximately parallel to) the user's face, which gives the blower and therefore patient interface a low profile configuration on the user's face. Ideally the distance the patient interface extends from the user's face is a small as possible. The patient interface should be as flat as possible against the user's face. Preferably the centre of mass of the blower is as close to the user's face as possible.

FIGS. 9 to 12 show further embodiments in which the seal is detachable from the frame body. For example the seal may be detached for cleaning or to enable different sizes of seal to be tried when initially fitting a patient with the interface for example (and the interface may be provided with different sizes of seal). In some embodiments the seal may be formed entirely from a soft material such as a silicone material, which is thickened where the seal attaches to the body of the interface. In other embodiments the seal or seal module may comprise a relatively rigid seal clip or clips or other parts for releasably attaching the seal to the mask body, for example in a snap fit.

Also the interface shown in these embodiments as well as the embodiments of FIGS. 7 and 8 is a hybrid full face interface which covers the mouth and contacts the underside of the nose having an outlet which is positioned beneath the nares, of the type described in our international patent application publication WO2014/062070 the entire content of which is incorporated herein by reference. Also incorporated herein by reference are our international patent application publications WO2014/175753, WO2015/020535, WO2015/193821, and WO2016/075658. Alternatively the interface may be a full face interface which covers both the nose and mouth, a hybrid full face interface which covers the mouth and comprises nasal nozzles or pillows or similar which enter into the nares, an indirect or direct nasal interface which covers the patient's nose or comprises nasal nozzles or pillows or similar which enter into and seal against or within the nares of the wearer or cannula which non-sealingly enter the nares, or an oral (only) interface.

Specifically, in the embodiments of FIGS. 9 to 12 the seal surrounds the user's mouth and has an oral aperture 500 for gases flow to the wearer's mouth, and has a nasal outlet or outlets 501 beneath the nose. The seal preferably also comprises left and right paddle or wing 512 and 514 portions in the upper nasal part of the seal which may seal against lateral sides of the nose and/or at least allow the tip of the nose to be exposed. The nasal outlet or outlets 501 beneath the nose are in the bottom of a valley defined between the paddles 512 and 514 which accommodates at least a tip of a nose of the user such that the upper surface 516 underlies the nose. A band 505 of the seal is disposed between the oral opening 500 and the nasal opening 501, but may be omitted so that the oral opening and nasal opening merge into a combined oral nasal opening. Preferably, the paddles 512 and 514 are hollow and in fluid communication with the wearer side interior of the seal so that pressure within the seal tends to inflate the paddles 512 and 514.

Figure 13:
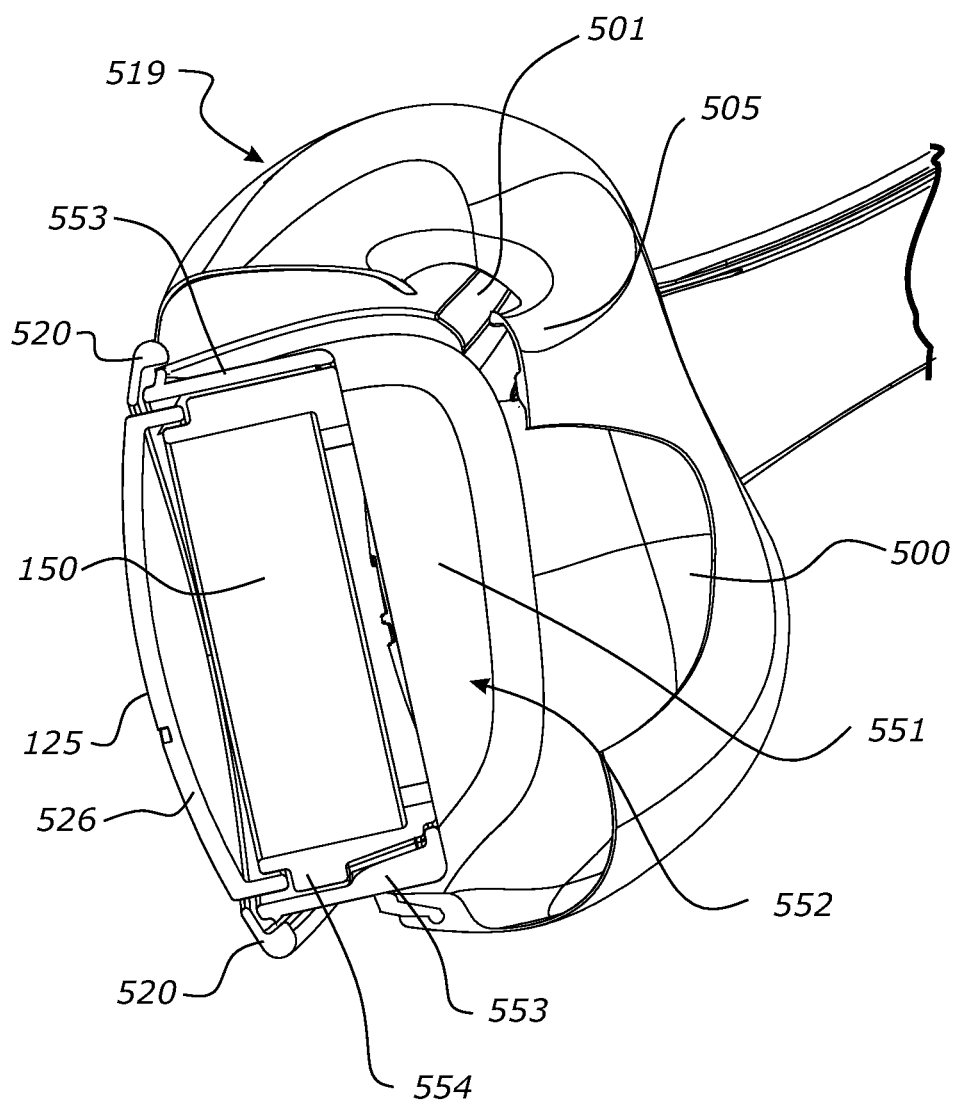
FIG. 13 is a sectioned view of a cushion module attached to an interface body of the patient interfaces of FIGS. 9A-11E.
Figure 14A:
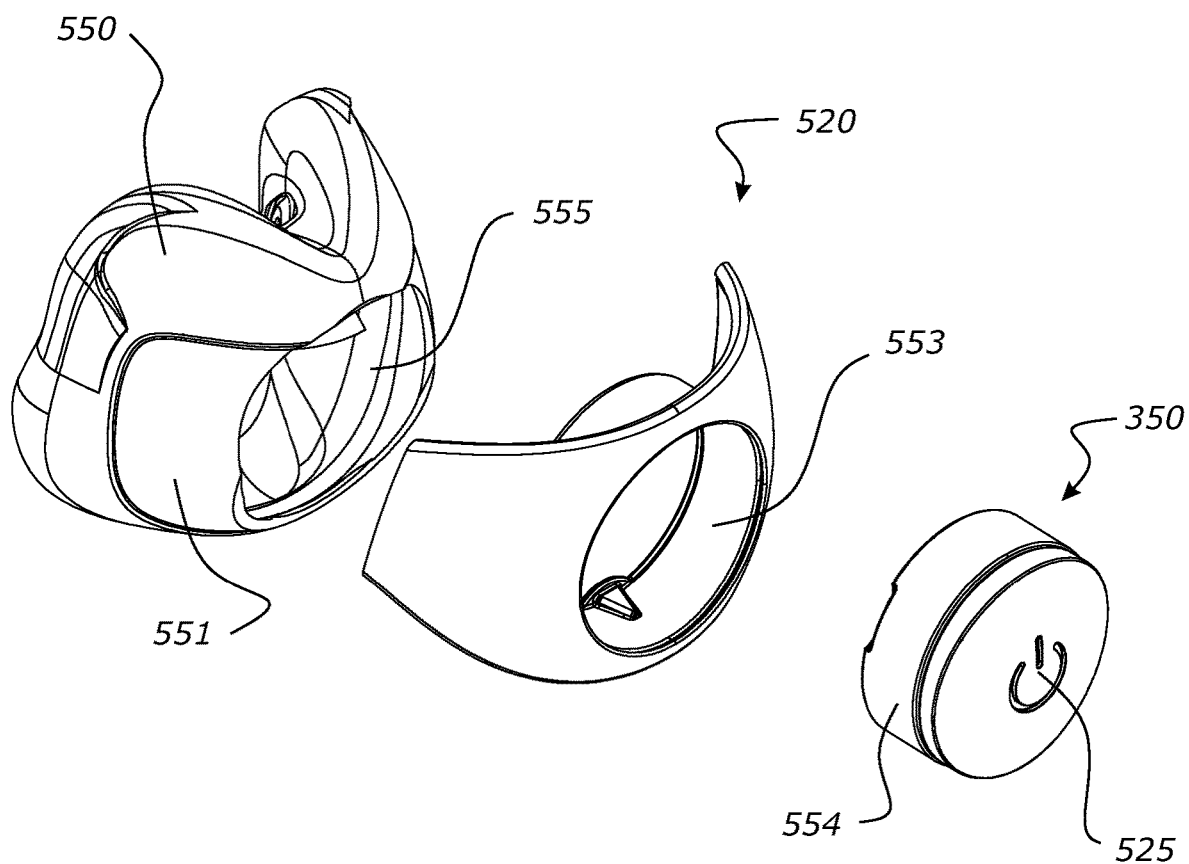
FIGS. 14A and 14B are exploded perspective views of the cushion module, mask body and blower of the patient interfaces of FIGS. 9A to 11E.
Figure 14B:
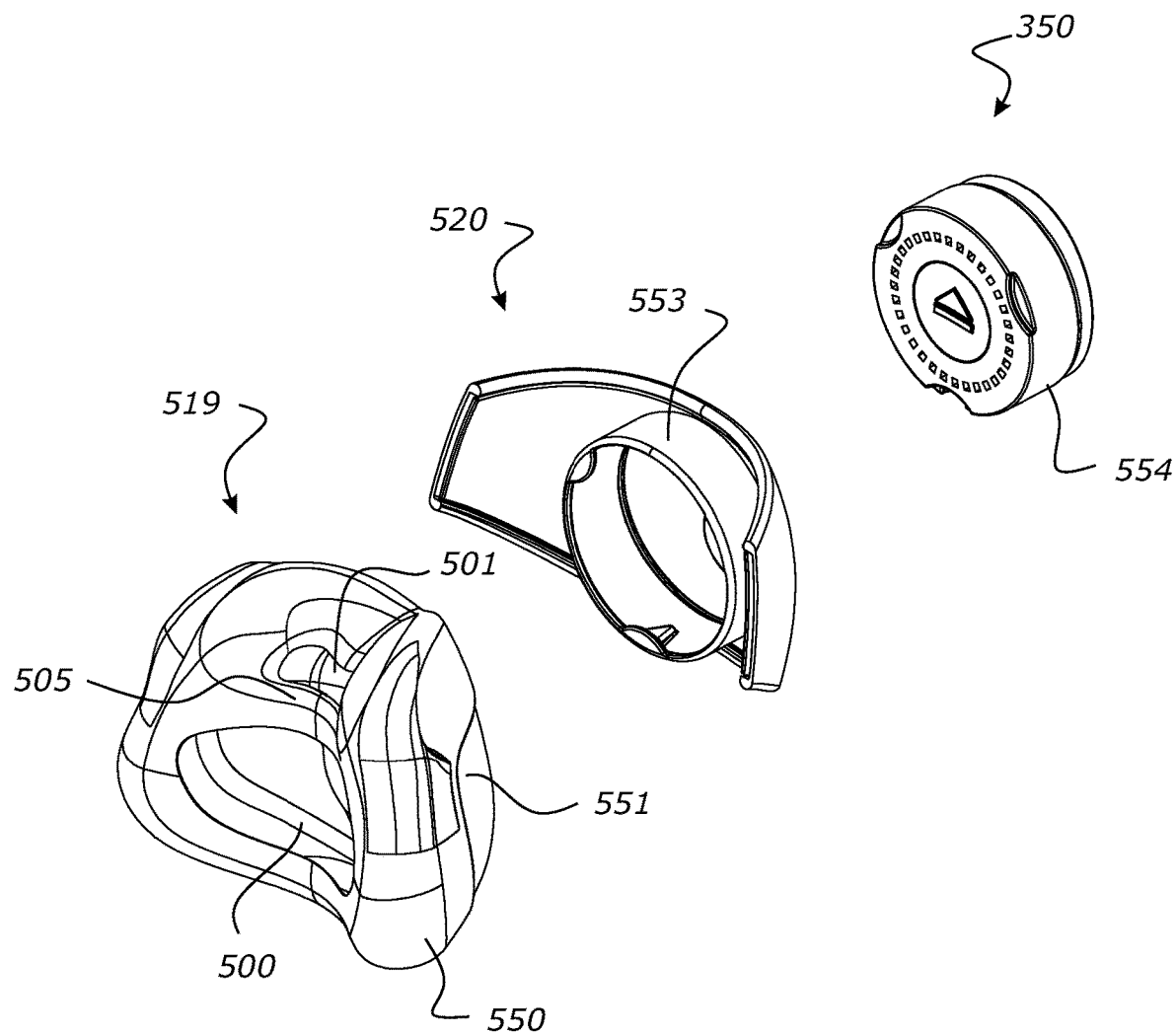

As stated above, in some embodiments the seal or cushion may be overmolded to the mask body or the seal may be attached to a relatively rigid seal clip for detachably clipping the cushion to the bask body. Referring to FIGS. 13 to 14B, and in particular FIG. 13 which is a cross-section through the seal module 519 attached to the mask body 520, of the embodiment of FIGS. 9 to 11E, the seal 550 of a relatively soft compliant material such as a silicone material as referred to above, is attached for example by overmolding, to a more rigid seal frame part 551, of for example a polycarbonate. The two parts seal 550 and seal frame 551 form the seal or cushion module 519, e.g. like the cushion module 138 of the embodiment of FIGS. 5A to 5H described above. As shown the more rigid seal frame part 551 has a depth in the front-back direction such that it defines a hollow interior 552, and it comprises an aperture 555 for gasses entry into the cushion module. The cushion module provides an interior space or volume for receiving a flow of gases (e.g. air) from the blower. In some embodiments the cushion module is attached to the interface body 520 by the aperture 550. In the illustrated embodiment the mask body 520 comprises an inlet 553 to the interior space of the cushion module, and the inlet receives the blower. In the illustrated embodiment the inlet receives the blower so that the blower is received at least partly within the cushion module. The inlet 553 surrounds the blower such that the impeller and impeller space of the blower is located within the inlet, at least when viewed from a front of the patient interface. In the illustrated embodiment, the blower is located substantially wholly within the inlet, such that the impeller and motor of the blower are positioned within the inlet, e.g. radially within the inlet. Such an arrangement provides for a compact design. In the illustrated embodiment, the inlet comprises a ring 553 which receives the blower housing 554. The ring may be a tubular ring, for example comprising a cylindrical or tubular wall. The cushion module may attach to the mask body or frame 520 of the patient interface by the aperture fitting over or receiving the inlet, e.g. the ring 553, so that gas flow exits from the blower 350 rearwardly into the interior of the seal module 519. Alternatively the mask body ring 553 may fit within an annular flange or rear facing tabs on the blower housing, or any other form of interference/friction or clipping formations such as locking tabs on the mask frame which insert into recesses in the blower housing, may be provided adjacent or around the ring and/or blower housing, or on other parts of the seal module seal frame part and/or mask body or frame. Preferably the blower is mounted to the mask body or the cushion module frame by a portion of the blower housing that is radially outside of the impeller and/or a portion of the blower housing that surrounds the impeller and impeller space. This configuration positions the impeller in line with a direct (e.g. straight) flow path from outside of the patient interface to the interior space of the patient interface. In some embodiments, such as that shown in FIG. 13, the blower is located substantially within the mask body, and is preferably located substantially within the mask body 520 and/or the frame 551. In the illustrated embodiment, the mask body 520 and frame 551 are arranged so that the blower is located within the patient interface substantially without a wall of the mask body or frame between the blower and the interior space of the patient interface. Such an arrangement allows for the blower to be provided in the patient interface without ducting or plumbing from the outlet of the blower to the interior space of the patient interface. The blower is provided with the outlet of the blower opening directly into the interior space. In some embodiments the blower is mounted to the mask body 520 or the frame 551 by an outer perimeter or circumferential portion of the blower housing. In some embodiments, the blower is mounted to the mask body or frame so that the blower substantially separates a high pressure side of the mask body or frame from a low pressure side of the mask body or frame. As described earlier, the high pressure side is a side of the mask body or frame to which the blower delivers a flow of gases, and a low pressure side is a side of the mask body or frame from which the blower draws a flow of gases and corresponds with the inlet of the blower, e.g. an outside of the mask body or frame. In some embodiments the high pressure side of the mask body or frame is the side of the mask body facing or bounding the interior space. In some embodiments, as illustrated, the mask body 520 and the cushion frame 551 is without a vent path, such that the user must exhale through the blower from the blower outlet to the blower inlet. In some embodiments, the blower is located within the patient interface substantially without a wall of the mask body or frame between the blower and the interior space of the patient interface, and the patient interface may comprise a filter or diffuser medium or HME material between the blower or blower outlet and the interior space and/or the cushion. The filter or diffuser or HME material may substantially completely cover the blower such that the blower is not visible within the interior of the patient interface.

The embodiment illustrated in FIG. 13 may comprise either of the blowers 150, 250 described above. The ring 553 may comprise a cut out or aperture to correspond with the radial outlet 253 of the blower 250 for gases to pass from the blower and into the interior space of the cushion module 519.

In the illustrated embodiment as described above, the mask body comprises the ring 553, however, in an alternative embodiment the cushion frame 551 may comprise the ring 553, forming an inlet to the interior space of the patient interface. In such an embodiment, the mask body may attach to an outside of the cushion frame. The mask body may comprise an aperture or open front through which the blower drawings air into the inlet of the blower, and the mask body may clip or attach over a forward end of the ring 553 of the cushion frame 551.

In the embodiments shown the mask frame or body 520 has depth in the front-back direction such that the mask frame wraps around the front of the cushion module. Specifically the mask frame 520 comprises a center portion 521 and left and right side portions 522 and 523 which extend rearwardly and/or over the left and right sides of the user's mouth or cheeks when the interface is worn, and couple to or are integral with headgear as will be further described. The mask frame 520 also has height, such that the mask frame 520 covers in part or shrouds the front of the seal module.

The interface may be provided with a cover, for example cover 526. In the illustrated embodiment the cover 526 attaches to the blower and may form part of the blower housing. Alternatively the cover may attach to the mask body 520 or to the cushion frame 551. The cover may include apertures (not shown) to provide an inlet (like inlet 125 in FIG. 2A). An on-off switch for the blower may be provided on the interface, such as a large easily operated button or touch pad 525 on or at the front of the interface as shown. The button may be a depressible part of cover 526 allowing access to a button on the blower behind the cover. The button or touch pad and associated control circuit(s) of the blower motor may be arranged such that pressing or touching the button or pad turns the blower on then off then on etc with each operation. Alternatively or additionally sequential button or pad operations may increase or decrease the blower speed to suit the user where this is user adjustable.

Power Sources

In the embodiment of FIG. 9 the blower in the mask is powered from a battery pack 900 which is connected to the mask via cable 901. The battery pack 900 may be rechargeable by plugging the battery pack into a recharger or may incorporate a recharger so that the battery pack is recharged by plugging it into a mains power supply. The battery pack may be connected to a recharging power supply by coupling it to a recharging base 902 or cradle connected to mains power via cable 903. Placing the battery pack 900 on or in the recharging base 902 may mechanically connect contacts of the battery pack 900 to contacts of the recharging base 902 or may inductively connect circuits in the battery pack 900 and recharging base 902 to recharge the battery pack 900 from the recharging base 902 by inductive power transfer for example. The length of cable 901 may be sufficient to enable the battery pack to be located in a pocket of clothing or nightwear of the user or under a pillow e.g. length in the range 0.5 to 1 meter for example, or may be sufficient to enable the battery pack to be placed on a nightstand or bedside table adjacent the patient's bed e.g. 1 to 2 meters for example. The cable may include a clip for attaching the cable to the user's clothing or nightwear or pillow or bedding part way along its length.

Figure 10:
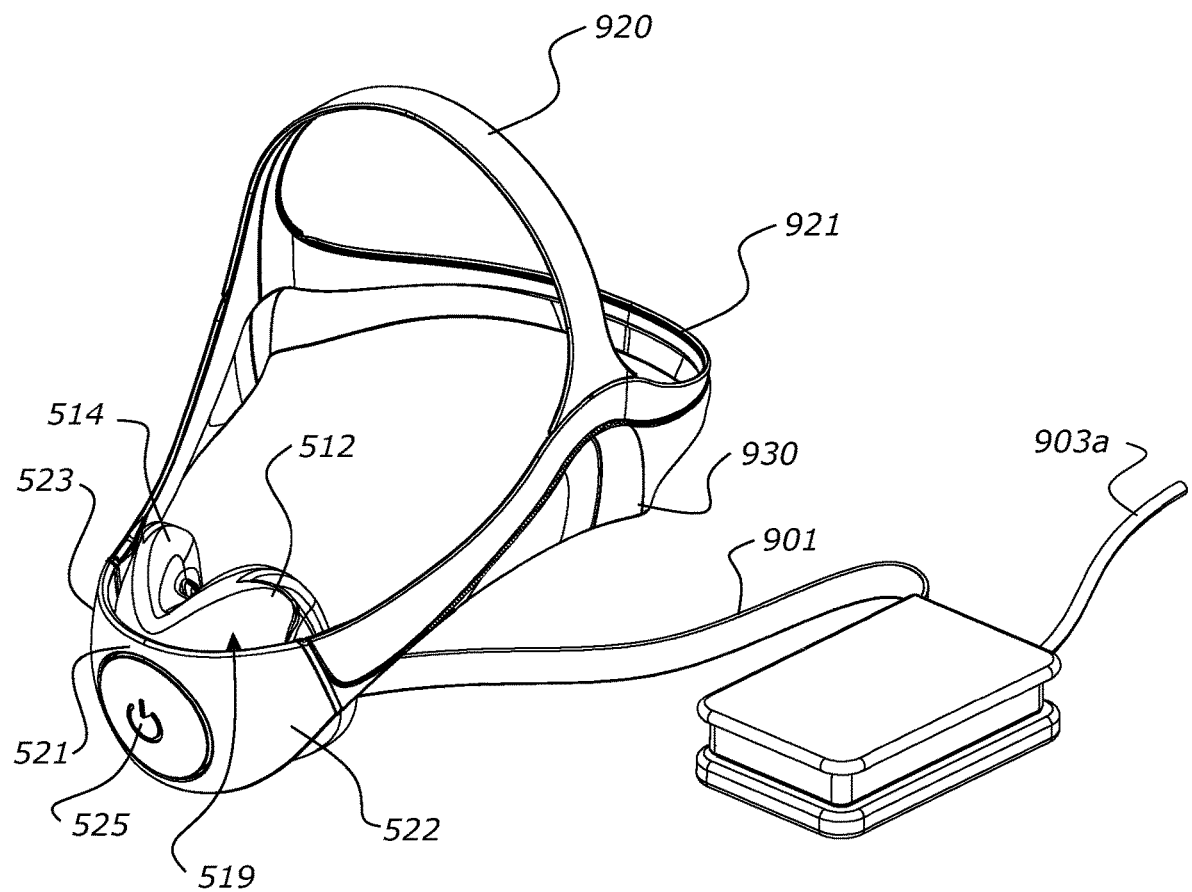
FIG. 10 is a perspective view of another embodiment of a patient interface, similar to that of FIG. 9.
Figure 11A:
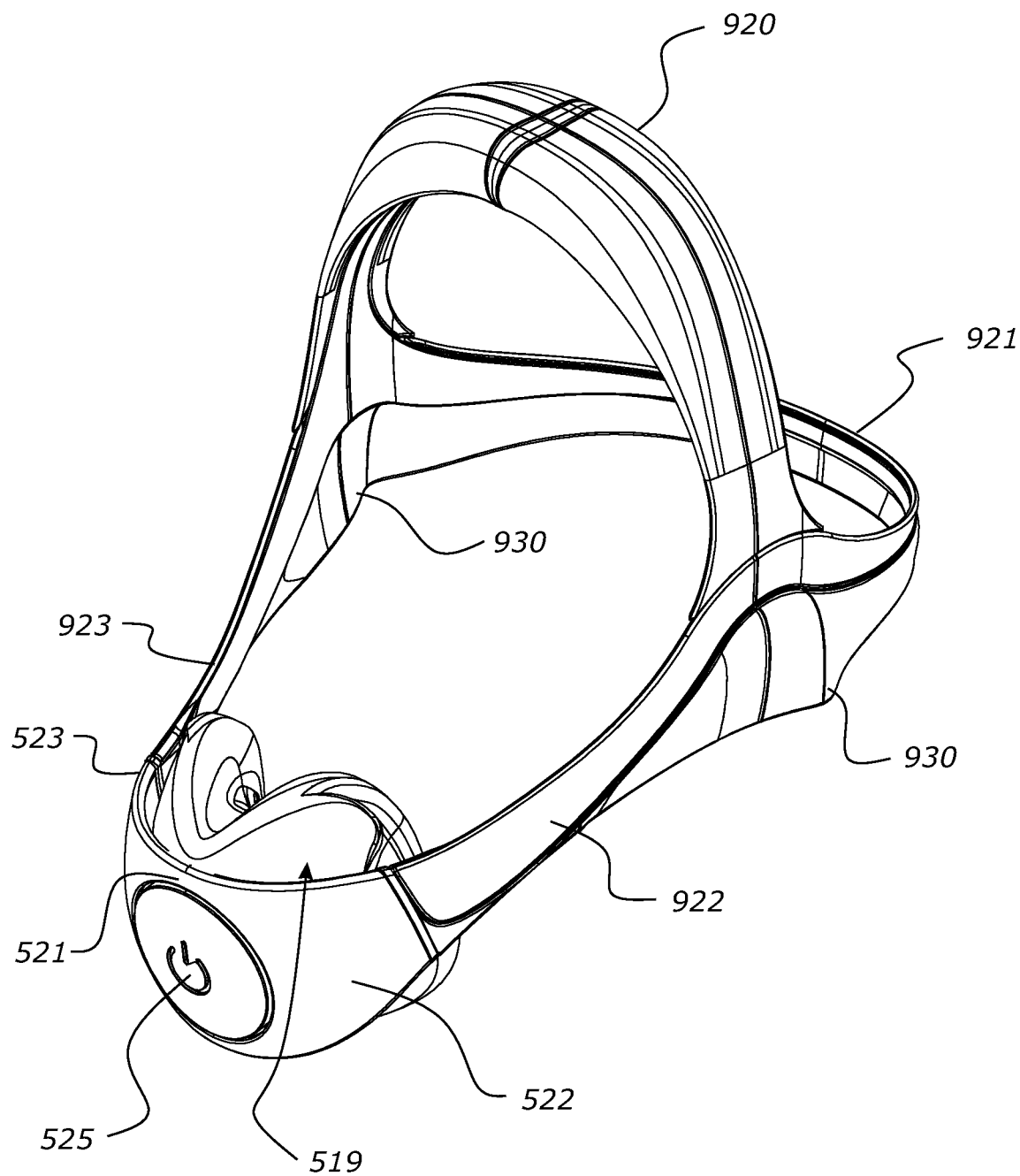
FIG. 11A is a perspective view of another embodiment of a patient interface.
Figure 11B:
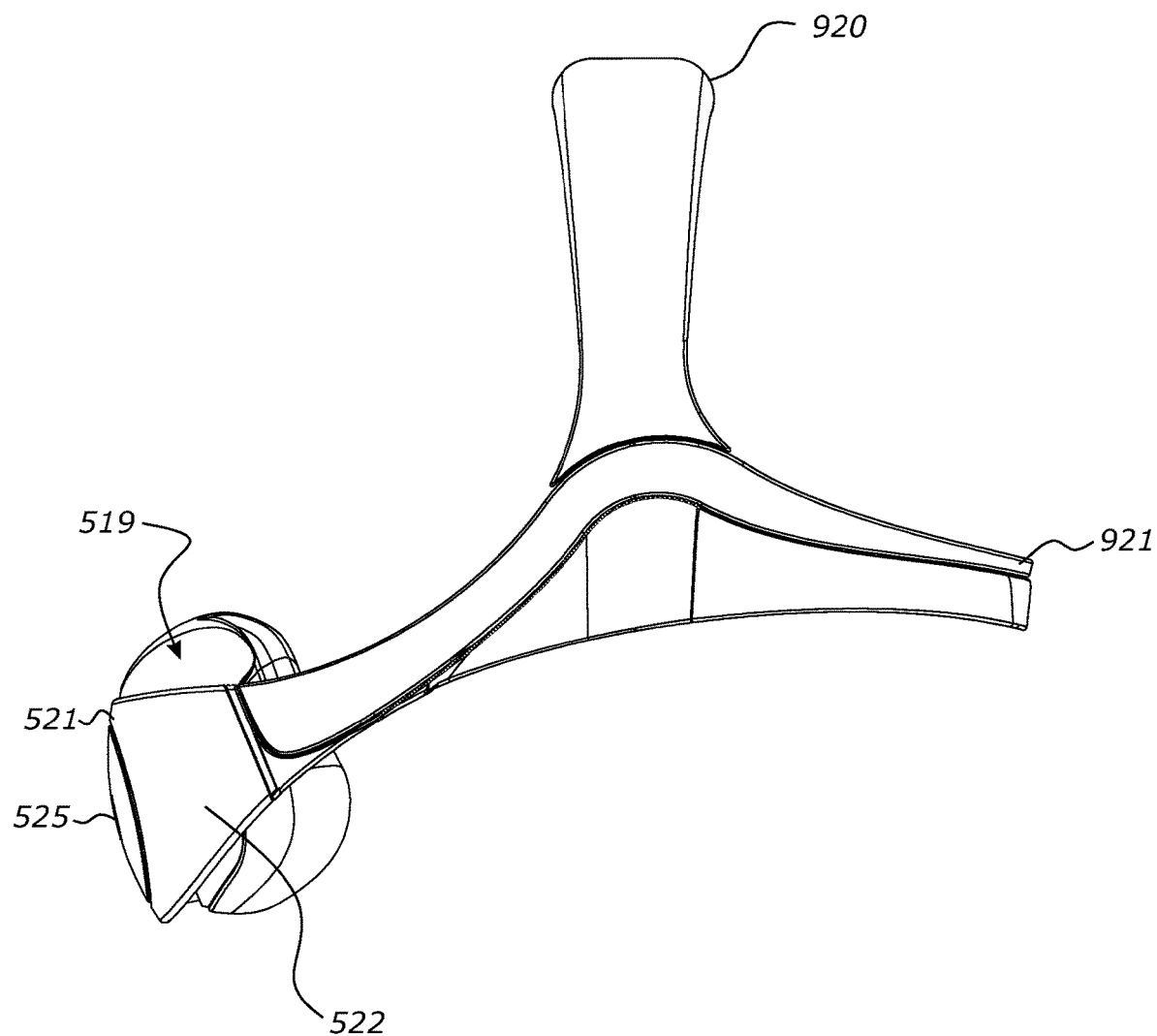
FIG. 11B is a side view of the patient interface of FIG. 11A.
Figure 11C:
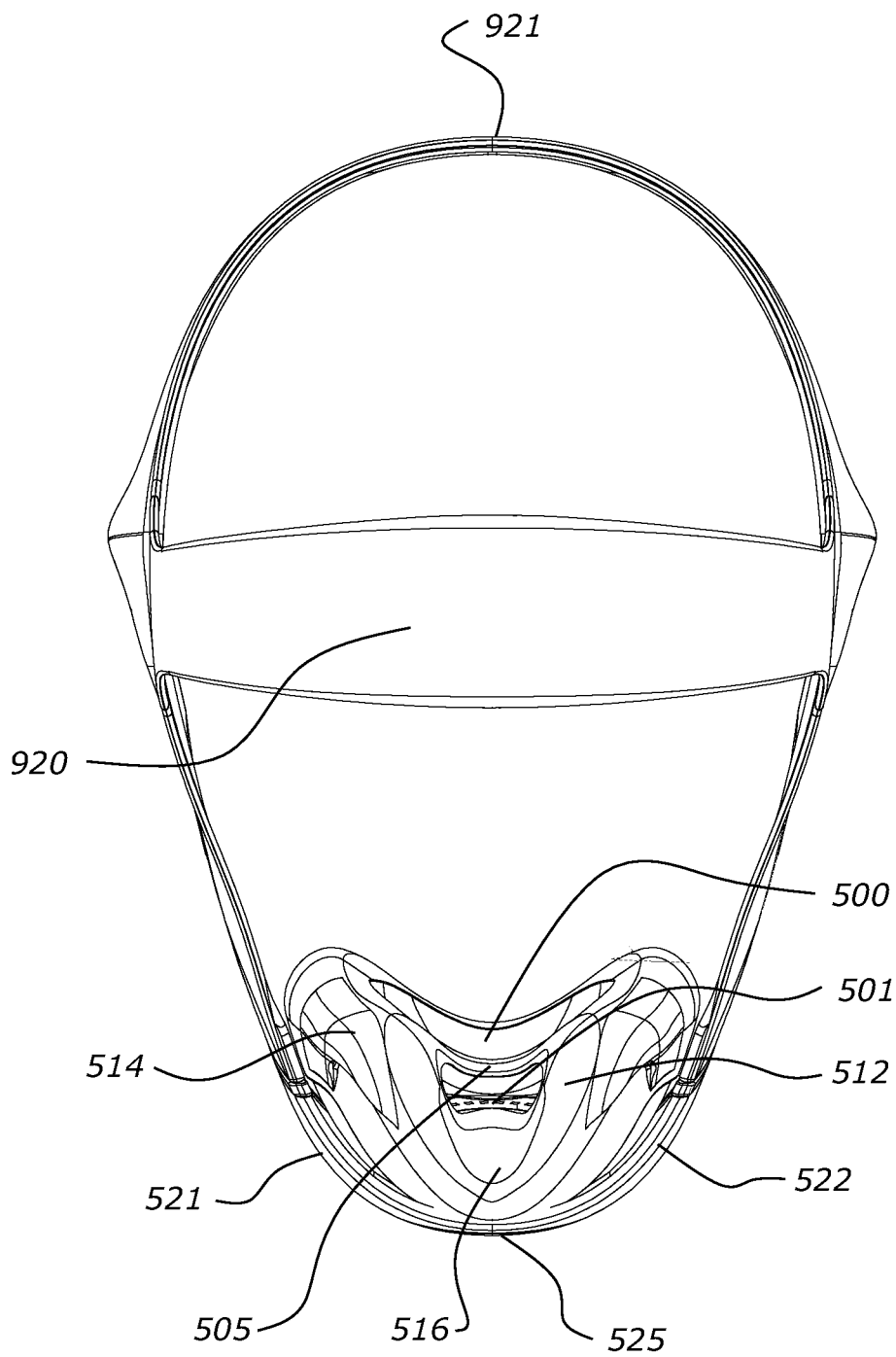
FIG. 11C is a view from above of the patient interface of FIGS. 11A and 11B.
Figure 11D:
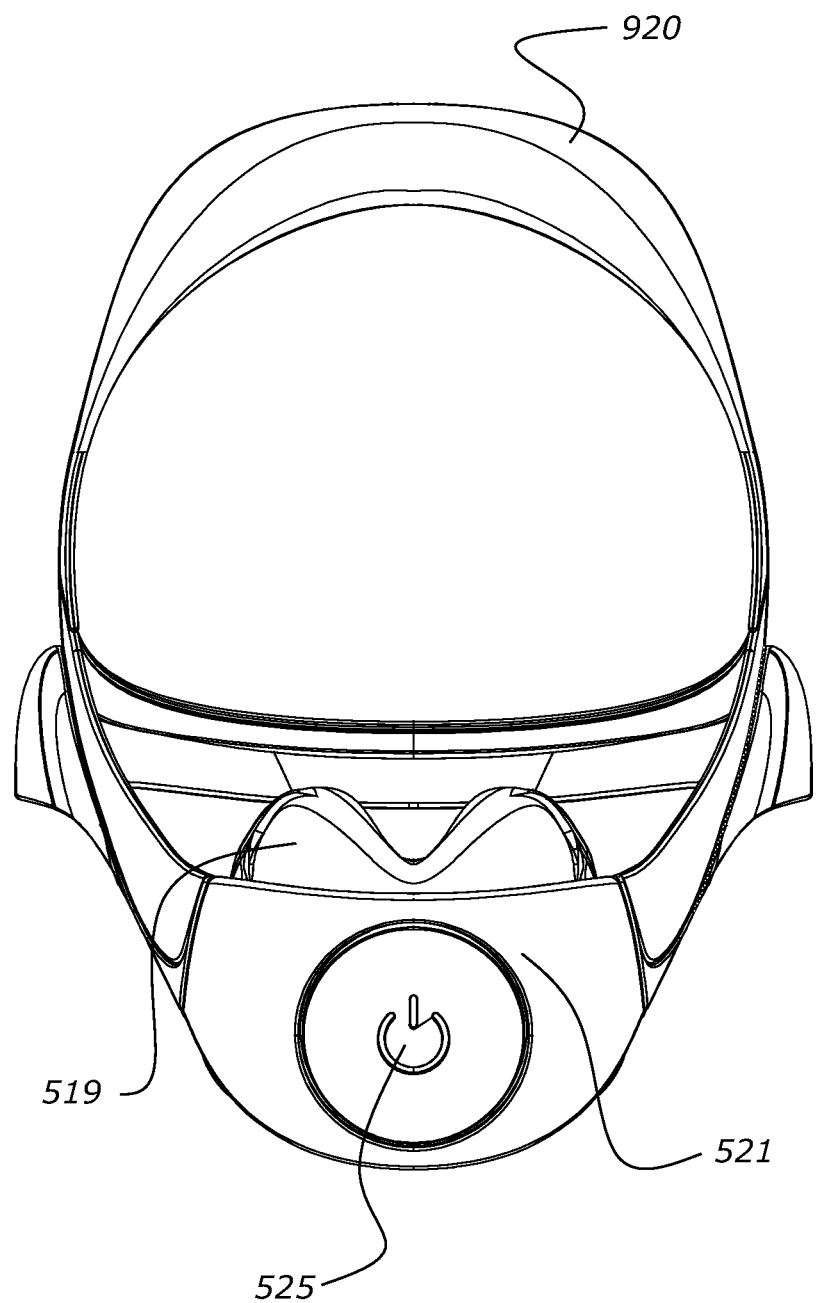
FIG. 11D is a front view of the patient interface of FIGS. 11A to 11C.
Figure 11E:
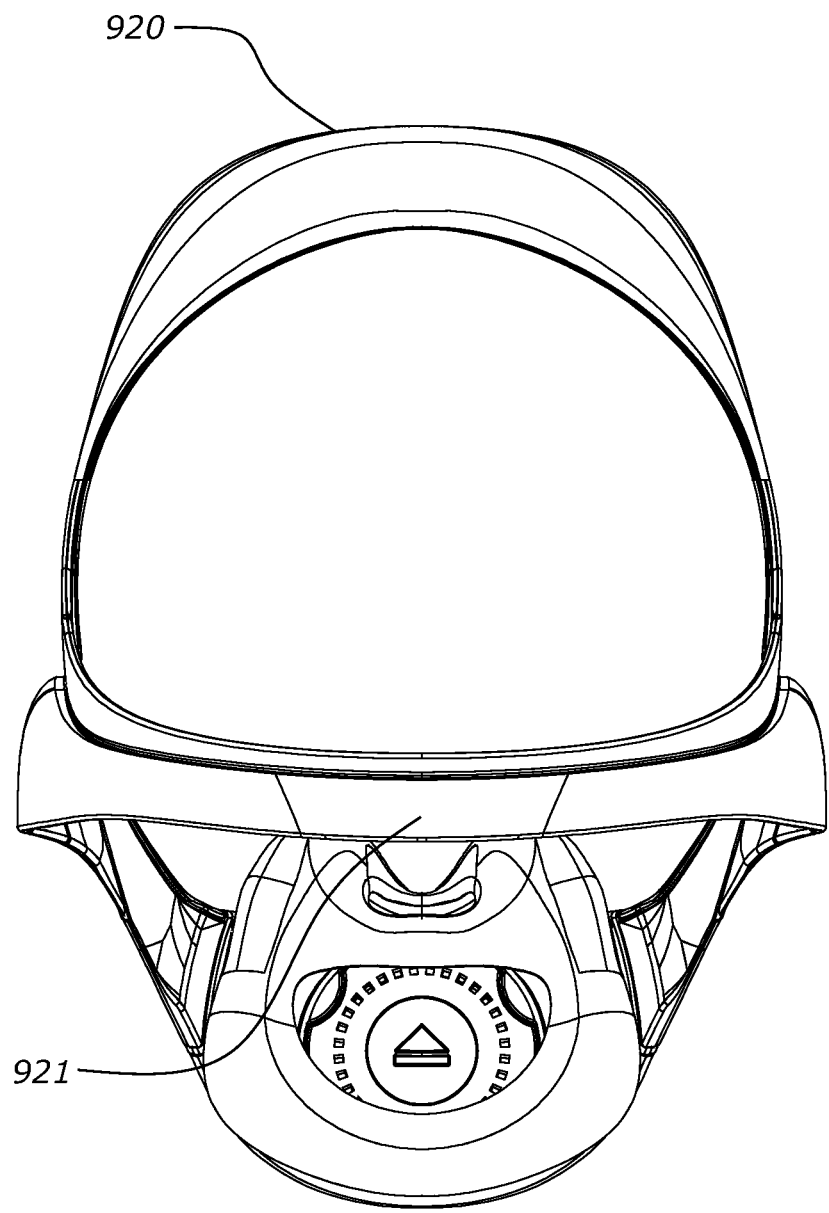
FIG. 11E is a rear view of the patient interface of FIGS. 11A to 11D.

In the embodiment of FIG. 10 the blower in the mask is powered directly from the mains power via cable 903*a*. Otherwise the embodiment of FIG. 10 is similar to the embodiment of FIG. 9 as described above and the same reference numerals indicate the same components.

In the embodiment of FIGS. 11A to 11E the blower in the mask is powered from a battery or batteries incorporated in a top strap or crown strap 920 of the headgear. Alternatively the battery or batteries may be incorporated in another part of the headgear such as a back or side strap or the body of the interface. The battery or batteries may comprise a removable battery pack for replacement for example. The battery may be housed within a cavity within the headgear strap or form a structural part of the headgear strap. In the embodiment shown the top headgear strap has a substantially flat wearer side which contacts the user's head, and an outer side wall which is arcuate such as approximately semicircle in cross-section shape, to define a battery cavity within and along the length of the headgear strap. The wearer side of the strap may be provided with a soft or compliant surface for wearer comfort. Batteries may be incorporated in more than one headgear strap such as a top and back headgear straps or left and right side headgear straps for example. The battery is connected to the blower via wires incorporated in preferably internally in, the headgear of the interface. A recharging port may be provided on the interface or headgear enabling a cable from a recharger to be connected to the interface for recharging the interface may incorporate a recharger so that the battery pack is recharged by plugging it into a mains power supply. The interface may be supplied with a purpose designed recharging cradle which may be placed on a nightstand or bedside table adjacent the patient's bed and carries the interface when not in use, and is connected to mains power, on which the interface sits during the day to recharge. Placing the battery pack 900 on or in a recharging base 902 may mechanically connect contacts of the battery pack 900 to contacts of the recharging base 902 or may inductively connect circuits in the battery pack 900 and recharging base 902 to recharge the battery pack 900 from the recharging base 902 by inductive power transfer.

Figure 12:
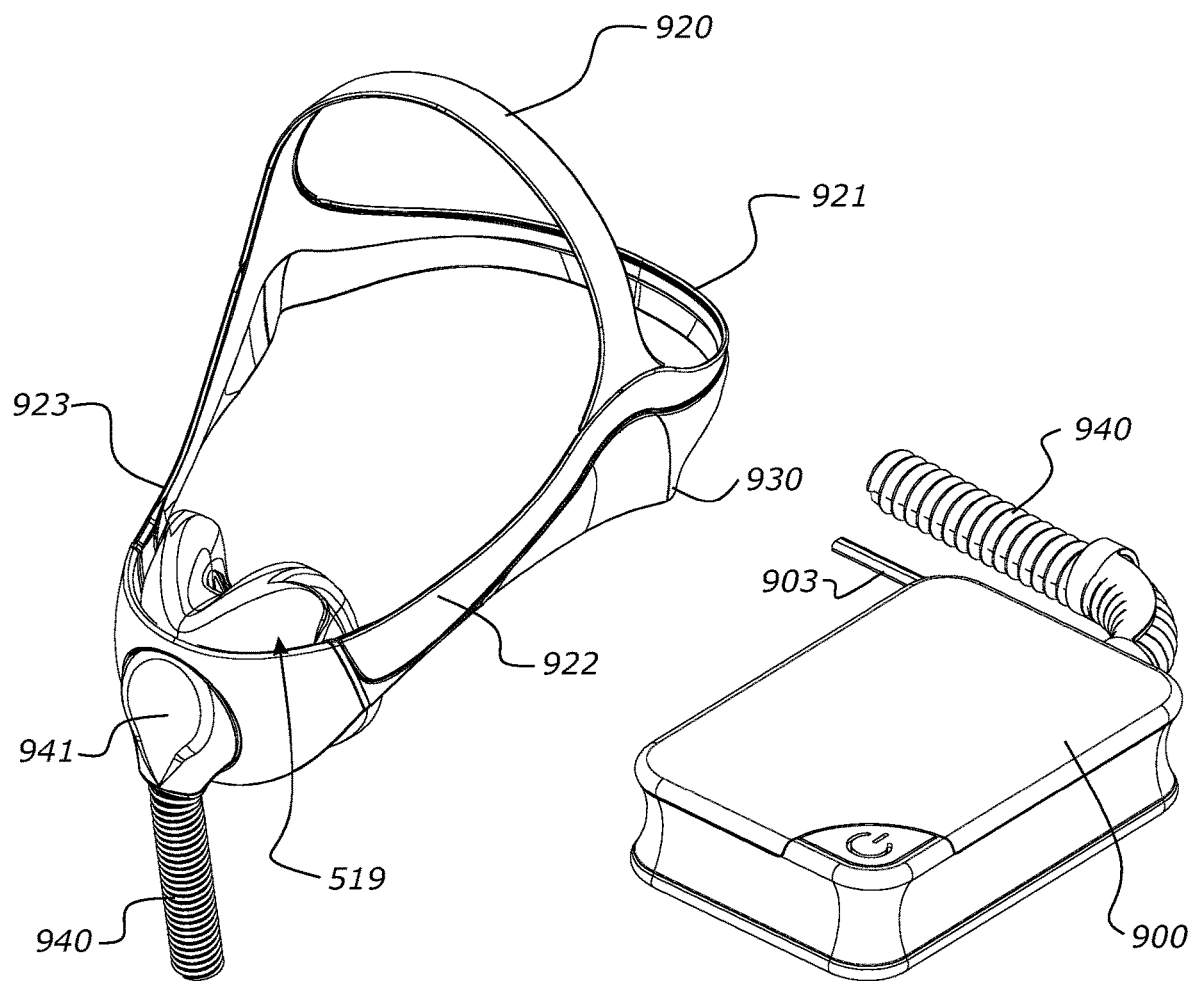
FIG. 12 is a perspective view of another embodiment of a patient interface.

The embodiment of FIG. 12 is similar to the embodiment of FIGS. 9 and 10 and the same reference numerals indicate the same components, except that the blower is incorporated in the battery pack 900 and an outlet of the blower is connected to the interface via a conduit 940 which connects to the interface body or frame 920 via a connector 941, which can be a swivel elbow.

The interface comprises headgear or a headgear assembly holds the interface in position on the user's head when worn. In at least some embodiments such as those shown in FIGS. 9 to 12 a headgear assembly comprises a rear strap 921 to extend around a rear part of the head of a wearer and a top strap 920 to extend over the top of a head of a wearer, and left and right side straps which extend from a junction of the top and side straps on either side of the headgear, forward on left and right sides to connect to the mask frame 520. The rear strap 921 may extend around a lower rear part of the head of the wearer and in particular over a lower part of the occipital bone. The top strap 920 may be a crown strap or a forehead strap. The headgear may define an occipital loop, and the headgear may be in various other forms. For example headgear may comprise upper side straps which extend above the ears and lower side straps which extend below the ears. The rear part of headgear can comprise a generally annular component comprising a back strap, a top strap and a pair of upright straps.

Headgear of interfaces described herein may be as described in our international patent application publication WO2016/043603 the entire content of which is incorporated herein by reference. The headgear or at least headgear parts may be formed by applying molten plastic onto a textile component placed within a moulding tool, or injecting molten plastic into a hollow textile component, bonding the moulded plastic and the textile component. A hollow textile component may be knitted or woven to a complex final shape of the headgear or headgear part. Such methods can be utilized to create headgear assemblies or portions thereof that can be substantially inelastic in at least one direction, such as a lengthwise direction of a strap of the headgear, while having a softer material positioned on at least one surface of the headgear or headgear portion without requiring a post-forming step of attaching the softer material and without the need for adhesives, sleeves or other methods of attaching the softer material to the moulded material.

In the headgear embodiments of FIGS. 9 to 12 a soft section 930 bridges a junction between headgear straps above the wearer's ear on each side to cover the top of the wearer's ears on each side, and can be of very fine, lightweight, stretch fabric to maximise comfort for the wearer.

In at least some embodiments the length of one or more headgear straps is adjustable. For example a top strap may be formed in two parts one of which terminates in a loop and the other of which terminates in a tongue which can pass through the loop and be secured back upon the strap part to fix the length of the top strap, by a hook or loop fastener panel on or tab from the end of the tongue and a loop or hook panel on the strap or to a cloth covering of the tab (loop and tongue adjustment). The rear strap may have a buckle and tongue on left and right sides length adjustment or alternatively on one side or centrally.

In other embodiments headgear may be formed from parts attached together, using for example ultrasonic/RF welding, or may be a single unitary pieces (not formed from separate attached parts). The length of one or more of the headgear straps may be adjustable. Headgear is commonly formed at least in part from a soft flexible material such as a cloth covered foam material such as BREATHE-O-PRENE material for example, but may be formed from any other material suitable material, such as in whole or part from a semi-rigid plastics material for example which may optionally be covered with a softer material. The headgear may be formed from parts attached together for example as disclosed in our international patent application publication WO2015/151019 the entire content of which is incorporated herein by reference, using for example ultrasonic welding, or may be a single unitary piece (not formed from separate attached parts). The headgear may comprise one or more rounded edges, formed in any suitable manner, for example by applying heat and pressure to edges of the headgear. The headgear assembly can be configured to directly couple to the mask assembly without the use of clips. In some configurations, the pair of upper side straps and the pair of lower side straps can comprise ends with fasteners that loop through headgear attachments on the mask assembly and the fasteners can be configured to couple with complementary fasteners on the sides of the pair of upper side straps and the pair of lower side straps. Further disclosure regarding headgear is at the end of this description.

In some embodiments such as the embodiments of FIGS. 2 and 5, the patient interface comprises a forehead support 122. In some embodiments, as shown in FIG. 2C, the forehead support extends from the mask body from an axial position at which the blower is located within the mask body. The forehead support extends from the mask body from above the blower. In some embodiments the centre of mass of the blower is positioned at or behind an axial location on the mask body from where the forehead support extends from the mask body. In other embodiments such as the embodiments of FIGS. 7 to 12 the interface does not comprise a forehead support.

In some embodiments the patient interface may comprise a filter medium or other air treatment medium. In some embodiments a treatment medium is provided at an inlet side of the mask body. For example, in some embodiments a treatment medium may be provided at the inlet 125 of the patient interface, or at the blower inlet 153, or in between the interface inlet 125 and the blower inlet 153. In some embodiments, a treatment medium may be provided at an outlet side of the mask body, for example at the blower outlet 151. As shown in FIGS. 8A and 8B, patient interface 400 comprises a treatment medium 115 at the inlet 125. In some embodiments the treatment medium is a filter medium, or a Heat and Moisture Exchange medium that extracts moisture from a user's breath to humidify air provided by the blower. A suitable HME material is described in PCT application PCT/IB2014/065194 published as WO2015/052681.

Figure 1:
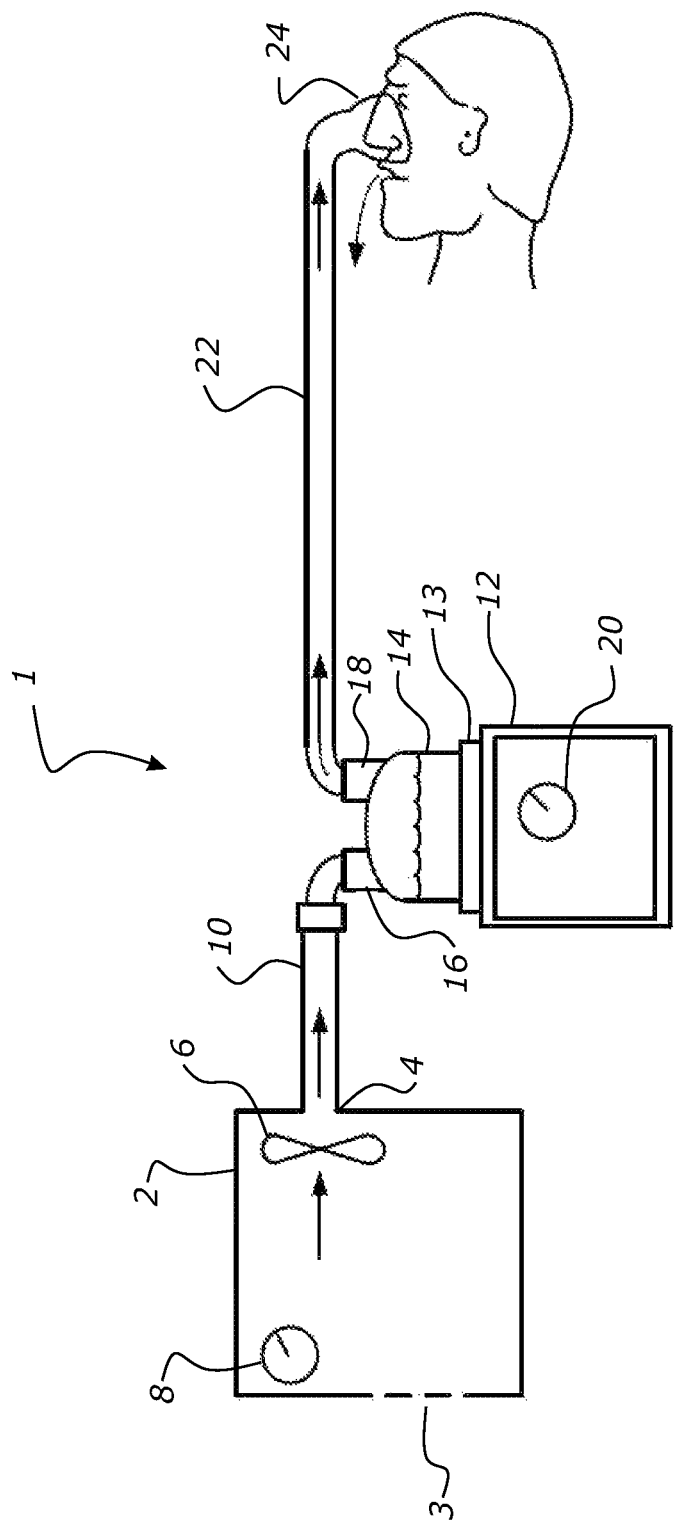
FIG. 1 illustrates a typical CPAP system.

In embodiments described herein, the blower is not remote from the patient interface like in a traditional system such as that indicated in FIG. 1. In the embodiments described, the patient interface comprises the blower, so that no hoses or respiratory conduits are required to extend from the patient interface.

Preferably the blower is lightweight. In some embodiments the blower has a total weight of about 25 grams to 100 grams, or about 25 grams to 35 grams, or about 35 grams to 60 grams, or about 60 grams to 100 grams. In some embodiments the blower has a total volume of about 40 cc to 80 cc, or about 40 cc, or about 55 cc or about 70 cc. The blower may be approximately circular with an outer diameter of about 50 mm to 70 mm, or about 50 mm to 60 mm. In some embodiments the blower may have an axial length of around 15 mm to 30 mm, or about 20 mm to 25 mm, or about 18 mm, or about 22 mm. Preferably the blower is quiet. In some embodiments the blower emits a noise level during operation of less than about 50 dBa, or less than about 40 dBa, or less than about 30 dBa, or about 30 to 40 dBa. In some embodiments the blower generates a pressure level at the mask cushion of about 0 to 30 cm H2O, or about 0 to 4 cm H2O, or about 4 to 10 cm H2O, or about 4 to 20 cm H2O, or about 4 to 30 cm H2O.

Where, in the foregoing description reference has been made to integers or components having known equivalents thereof, those integers are herein incorporated as if individually set forth.

The invention may also be said broadly to consist in the parts, elements and features referred to or indicated in the specification of the application, individually or collectively, in any or all combinations of two or more of said parts, elements or features.

Certain features, aspects and advantages of some configurations of the present disclosure have been described with reference to CPAP therapy. However, certain features, aspects and advantages of the configurations as described may advantageously be used in other respiratory care settings or for other purposes. For example, a patient interface comprising a blower may be useful together with a filter medium in hazardous environments, as the blower may assist the user to draw air through the filter medium.

The foregoing description of the invention includes preferred forms thereof. Modifications may be made thereto without departing from the scope of the invention.

The invention claimed is:

1. A patient interface comprising:
   a blower comprising an impeller, a motor for driving rotation of the impeller, a blower housing providing an impeller space for housing the impeller, a blower inlet and a blower outlet,
   a cushion for contacting a user's face,
   a mask body or frame for supporting the cushion on a user's face, the cushion and/or the mask body or frame defining an interior space for receiving a flow of gases from the blower,
   wherein the blower is mounted to an inlet to the mask body or frame so that the blower housing is coaxial with the inlet of the mask body or frame wherein the inlet to the mask body or frame comprises an inlet to the interior space, and
   wherein the blower substantially separates a high pressure side of the mask body or frame from a low pressure side of the mask body or frame.

2. The patient interface as claimed in claim 1, wherein the blower is mounted to the mask body or frame by a portion of the blower housing that is radially outside of and/or surrounding the impeller and the impeller space.

3. The patient interface as claimed in claim 1, wherein the blower is mounted to the mask body or frame by an outer periphery or circumferential portion of the blower housing.

4. The patient interface as claimed in claim 1, wherein the blower is located substantially wholly within the mask body and/or the frame.

5. The patient interface as claimed in claim 1, wherein the blower is bounded by a perimeter of the mask body around an open front or rear of the mask body.

6. The patient interface as claimed in claim 1, comprising the mask body and the frame, wherein the frame is a cushion frame integrated in a cushion module with the cushion, the cushion frame and/or cushion defining the interior space, and
   the mask body configured to attach headgear to and support the cushion module on a user's face.

7. The patient interface as claimed in claim 6, wherein the blower is mounted to the mask body or the cushion frame to be at least partly received within the cushion module.

8. The patient interface as claimed in claim 6, wherein the blower is received within the inlet to the mask body or frame, and wherein the inlet to the mask body or frame surrounds the impeller and the impeller space of the blower and/or the impeller and the impeller space are radially within the inlet to the mask body or frame.

9. The patient interface as claimed in claim 8, wherein the inlet to the mask body or frame surrounds the motor and/or the motor is located radially within the inlet to the mask body or frame.

10. The patient interface as claimed in claim 8, wherein the blower is located within the inlet to the mask body or frame.

11. The patient interface as claimed in claim 8, wherein the mask body comprises the inlet to the mask body or frame, and wherein the inlet to the mask body or frame extends into the cushion module so that the blower is at least partly within the cushion module.

12. The patient interface as claimed in claim 11, wherein the cushion frame comprises an aperture for gases entry into the interior space, and wherein the aperture receives the inlet to the mask body or frame to attach the cushion module to the mask body.

13. The patient interface as claimed in claim 8, wherein the inlet to the mask body or frame comprises a ring for receiving the blower.

14. The patient interface as claimed in claim 1, comprising a cover attached to the mask body or the frame or to the blower housing to cover the blower, the cover comprising a cover inlet to allow a flow of gases to the blower inlet.

15. The patient interface as claimed in claim 1, wherein a primary pneumatic connection between a low and high pressure sides of the patient interface is via a flow path through the blower from the blower inlet to the blower outlet.

16. The patient interface as claimed in claim 1, wherein the patient interface comprises a seal between the blower housing and the mask body or the frame.

17. The patient interface as claimed in claim 16, wherein the seal comprises a resilient and/or compliant sealing material provided to the blower housing or the mask body or the frame.

18. The patient interface as claimed in claim 17, wherein the sealing material is over moulded to the blower housing or to the mask body or to the frame.

19. The patient interface as claimed in claim 18, wherein a resilient material is over moulded to the frame and is of the same material as a cushion.

20. The patient interface as claimed in claim 17, wherein a seal material and a cushion are integrally formed as a unitary member over moulded to the mask body or the frame.

21. The patient interface as claimed in claim 1, wherein a diameter or an overall lateral dimension of the blower is substantially larger than an axial length of the blower.

22. The patient interface as claimed in claim 1, wherein the blower comprises an axial outlet, or an axial inlet and an axial outlet.

23. The patient interface as claimed in claim 1, wherein a first external surface of the blower is exposed to the high pressure side of the mask body and/or the frame, wherein a second external surface of the blower is exposed to the low pressure side of the mask body and/or the frame, and wherein a second surface is opposite a first surface.

24. The patient interface of claim 1, further comprising a filter or diffuser medium or HME material between the blower or the blower outlet and the interior space of the patient interface.

25. The patient interface of claim 1, wherein the cushion is directly attached to or formed with the mask body or frame.

26. The patient interface of claim 14, wherein the cover at least partially surrounds the blower.

27. The patient interface of claim 1, wherein the blower is releasably mounted or received within the inlet to the mask body or frame.

28. The patient interface of claim 1, wherein the blower is mounted to the inlet to the mask body or frame by at least one of a screw engagement, a rotational engagement, a push fit engagement, and a snap fit engagement.

* * * * *

UNITED STATES PATENT AND TRADEMARK OFFICE
CERTIFICATE OF CORRECTION

PATENT NO. : 11,813,400 B2
APPLICATION NO. : 15/769707
DATED : November 14, 2023
INVENTOR(S) : Donald Roy Kuriger It is certified that error appears in the above-identified patent and that said Letters Patent is hereby corrected as shown below:

In the Specification

In Column 2, Line 30, delete "and or" and insert --and/or--.

In Column 7, Line 13, delete "frame" and insert --frame.--.

In Column 8, Line 37, delete "noun" and insert --noun.--.

In Column 10, Line 2, delete "FIG." and insert --FIGS.--.

In Column 10, Line 26, delete "As" and insert --as--.

In Column 19, Line 9, delete "FIG." and insert --FIGS.--.

In Column 19, Line 43, delete "20 mm" and insert --20 mm.--.

In the Claims

In Column 26, Claim 1, Line 33, delete "frame" and insert --frame,--.

Signed and Sealed this
Fifth Day of March, 2024

*Katherine Kelly Vidal*

Katherine Kelly Vidal
*Director of the United States Patent and Trademark Office*